United States Patent
Alessi et al.

(10) Patent No.: US 10,527,170 B2
(45) Date of Patent: Jan. 7, 2020

(54) OSMOTIC DELIVERY SYSTEMS AND PISTON ASSEMBLIES FOR USE THEREIN

(71) Applicant: Intarcia Therapeutics, Inc., Hayward, CA (US)

(72) Inventors: Thomas R. Alessi, Hayward, CA (US); Michael A. DesJardin, Sunnyvale, CA (US); Stan Lam, Dublin, CA (US); Scott D. Lautenbach, San Mateo, CA (US); Pauline C. Zamora, Sausalito, CA (US)

(73) Assignee: INTARCIA THERAPEUTICS, INC., Boston, MA (US)

( * ) Notice: Subject to any disclaimer, the term of this patent is extended or adjusted under 35 U.S.C. 154(b) by 550 days.

(21) Appl. No.: 14/316,969

(22) Filed: Jun. 27, 2014

(65) Prior Publication Data

US 2014/0378900 A1 Dec. 25, 2014

Related U.S. Application Data

(63) Continuation of application No. 12/930,950, filed on Jan. 19, 2011, now Pat. No. 8,801,700, which is a
(Continued)

(51) Int. Cl.
*F16J 9/26* (2006.01)
*F16J 9/28* (2006.01)
(Continued)

(52) U.S. Cl.
CPC .............. *F16J 9/26* (2013.01); *A61K 9/0004* (2013.01); *A61K 9/0024* (2013.01);
(Continued)

(58) Field of Classification Search
CPC ........... A61M 2005/14513; A61M 2205/0216; A61M 5/14276; A61M 5/14526;
(Continued)

(56) References Cited

U.S. PATENT DOCUMENTS 2,110,208 A 3/1938 Eggert
2,168,437 A 8/1939 Buercklin
(Continued)

FOREIGN PATENT DOCUMENTS

CN 1671439 A 9/2005
EP 0052510 A2 5/1982
(Continued)

OTHER PUBLICATIONS

Adolf, "Human interferon omega—a review," Mult. Sclr. 1:S44-47 (1995).
(Continued)

*Primary Examiner* — Quynh-Nhu H. Vu
(74) *Attorney, Agent, or Firm* — Brian C. Trinque; Lathrop Gage LLP

(57) ABSTRACT

An osmotic delivery system is disclosed for delivering an active agent formulation to a fluid environment. The osmotic delivery system typically comprises a reservoir having a lumen that contains the active agent formulation and an osmotic agent formulation and a piston assembly positioned in the lumen to isolate the active agent formulation from the osmotic agent formulation. The piston assembly typically comprises a body constructed and arranged for positioning in the lumen. The body is typically made of a polymeric material that is, for example, resistant to leaching in an organic solvent. In one embodiment, the body is a columnar body having a rim at a distal end thereof for engaging and sealing against a wall of the reservoir and the piston assembly further comprises a spring retained at the distal end of the columnar body for biasing the rim of the columnar body against the wall of the reservoir.

12 Claims, 3 Drawing Sheets

Related U.S. Application Data continuation of application No. 12/658,570, filed on Feb. 9, 2010, now Pat. No. 7,879,028, which is a continuation of application No. 11/890,836, filed on Aug. 8, 2007, now Pat. No. 7,682,356.

(60) Provisional application No. 60/821,830, filed on Aug. 9, 2006, provisional application No. 60/930,205, filed on May 15, 2007.

(51) Int. Cl.
    *A61M 5/145* (2006.01)
    *A61K 9/00* (2006.01)
    *A61M 5/142* (2006.01)

(52) U.S. Cl.
    CPC .... *A61M 5/14276* (2013.01); *A61M 5/14526* (2013.01); *F16J 9/28* (2013.01); *A61M 2005/14513* (2013.01); *A61M 2205/0216* (2013.01); *Y10T 29/49826* (2015.01)

(58) Field of Classification Search
    CPC ........ A61K 9/0004; A61K 9/0024; F16J 9/26; F16J 9/28; Y10T 29/49826
    See application file for complete search history.

(56) References Cited

U.S. PATENT DOCUMENTS

| | | | |
|---|---|---|---|
| 3,025,991 | A | 3/1962 | Gillon |
| 3,122,162 | A | 2/1964 | Sands |
| 3,523,906 | A | 8/1970 | Vrancken et al. |
| 3,625,214 | A | 12/1971 | Higuchi |
| 3,632,768 | A | 1/1972 | Bergy et al. |
| 3,691,090 | A | 9/1972 | Kitajima et al. |
| D226,915 | S | 5/1973 | Huggins |
| 3,732,865 | A | 5/1973 | Higuchi et al. |
| 3,737,337 | A | 6/1973 | Schnoring et al. |
| 3,773,919 | A | 11/1973 | Boswell et al. |
| 3,797,492 | A | 3/1974 | Place |
| 3,869,549 | A | 3/1975 | Geller |
| 3,891,570 | A | 6/1975 | Fukushima et al. |
| D236,035 | S | 7/1975 | Ciencewicki |
| 3,960,757 | A | 6/1976 | Morishita et al. |
| 3,987,790 | A | 10/1976 | Eckenhoff et al. |
| 3,995,631 | A | 12/1976 | Higuchi et al. |
| 3,995,632 | A | 12/1976 | Nakano et al. |
| 4,008,719 | A | 2/1977 | Theeuwes et al. |
| 4,034,756 | A | 7/1977 | Higuchi et al. |
| 4,078,060 | A | 3/1978 | Benson et al. |
| 4,111,201 | A | 9/1978 | Theeuwes |
| 4,111,202 | A | 9/1978 | Theeuwes |
| 4,111,203 | A | 9/1978 | Theeuwes |
| 4,203,439 | A | 5/1980 | Theeuwes |
| 4,211,771 | A | 7/1980 | Witkowski et al. |
| 4,221,862 | A | 9/1980 | Naito et al. |
| 4,243,030 | A | 1/1981 | Lynch et al. |
| D258,837 | S | 4/1981 | Spranger et al. |
| 4,305,927 | A | 12/1981 | Theeuwes et al. |
| 4,310,516 | A | 1/1982 | Chang et al. |
| 4,340,054 | A | 7/1982 | Michaels |
| 4,350,271 | A | 9/1982 | Eckenhoff |
| 4,373,527 | A | 2/1983 | Fischell |
| 4,376,118 | A | 3/1983 | Daher |
| 4,384,975 | A | 5/1983 | Fong |
| 4,389,330 | A | 6/1983 | Tice et al. |
| 4,439,196 | A | 3/1984 | Higuchi |
| 4,455,143 | A | 6/1984 | Theeuwes et al. |
| 4,455,145 | A | 6/1984 | Theeuwes |
| 4,530,840 | A | 7/1985 | Tice et al. |
| 4,552,561 | A | 11/1985 | Eckenhoff et al. |
| 4,588,614 | A | 5/1986 | Lauchenauer |
| 4,594,108 | A | 6/1986 | Greminger, Jr. et al. |
| 4,609,374 | A | 9/1986 | Ayer |
| 4,639,244 | A | 1/1987 | Rizk et al. |
| 4,655,462 | A * | 4/1987 | Balsells .......... F16F 1/045 267/1.5 |
| 4,673,405 | A | 6/1987 | Guittard et al. |
| 4,675,184 | A | 6/1987 | Hasegawa et al. |
| 4,695,623 | A | 9/1987 | Stabinsky |
| 4,727,138 | A | 2/1988 | Goeddel et al. |
| 4,734,284 | A | 3/1988 | Terada et al. |
| 4,737,437 | A | 4/1988 | Gutsell, Jr. et al. |
| 4,743,449 | A | 5/1988 | Yoshida et al. |
| 4,753,651 | A | 6/1988 | Eckenhoff |
| 4,762,791 | A | 8/1988 | Goeddel et al. |
| 4,765,989 | A | 8/1988 | Wong et al. |
| 4,783,337 | A | 11/1988 | Wong et al. |
| 4,818,517 | A | 4/1989 | Kwee et al. |
| 4,820,638 | A | 4/1989 | Swetly et al. |
| 4,826,144 | A | 5/1989 | Balsells |
| 4,830,344 | A | 5/1989 | Balsells |
| 4,840,896 | A | 6/1989 | Reddy et al. |
| 4,845,196 | A | 7/1989 | Cowling |
| 4,847,079 | A | 7/1989 | Kwan |
| 4,851,228 | A | 7/1989 | Zentner et al. |
| 4,865,845 | A | 9/1989 | Eckenhoff et al. |
| 4,873,080 | A | 10/1989 | Brickl et al. |
| 4,874,388 | A | 10/1989 | Wong et al. |
| 4,876,781 | A | 10/1989 | Balsells |
| 4,885,166 | A | 12/1989 | Meyer et al. |
| 4,886,668 | A | 12/1989 | Haslam et al. |
| 4,892,778 | A | 1/1990 | Theeuwes et al. |
| 4,893,795 | A | 1/1990 | Balsells |
| 4,897,471 | A | 1/1990 | Stabinsky |
| 4,907,788 | A | 3/1990 | Balsells |
| 4,915,366 | A | 4/1990 | Balsells |
| 4,915,949 | A | 4/1990 | Wong et al. |
| 4,915,954 | A | 4/1990 | Ayer et al. |
| 4,917,887 | A | 4/1990 | Hauptmann et al. |
| 4,917,895 | A | 4/1990 | Lee et al. |
| 4,923,805 | A | 5/1990 | Reddy et al. |
| 4,927,687 | A | 5/1990 | Nuwayser |
| 4,929,554 | A | 5/1990 | Goeddel et al. |
| 4,931,285 | A | 6/1990 | Edgren et al. |
| 4,934,666 | A | 6/1990 | Balsells |
| 4,940,465 | A | 7/1990 | Theeuwes et al. |
| 4,940,588 | A | 7/1990 | Sparks et al. |
| 4,952,402 | A | 8/1990 | Sparks et al. |
| 4,957,119 | A | 9/1990 | de Nijs |
| 4,961,253 | A | 10/1990 | Balsells |
| 4,964,204 | A | 10/1990 | Balsells |
| 4,969,884 | A | 11/1990 | Yum |
| 4,974,821 | A | 12/1990 | Balsells |
| 4,976,966 | A | 12/1990 | Theeuwes et al. |
| 5,004,689 | A | 4/1991 | Fiers et al. |
| 5,006,346 | A | 4/1991 | Theeuwes et al. |
| 5,019,382 | A | 5/1991 | Cummins, Jr. |
| 5,019,400 | A | 5/1991 | Gombotz et al. |
| 5,023,088 | A | 6/1991 | Wong et al. |
| 5,024,842 | A | 6/1991 | Edgren et al. |
| 5,030,216 | A | 7/1991 | Theeuwes et al. |
| 5,034,229 | A | 7/1991 | Magruder et al. |
| 5,057,318 | A | 10/1991 | Magruder et al. |
| 5,059,423 | A | 10/1991 | Magruder et al. |
| 5,066,436 | A | 11/1991 | Komen et al. |
| 5,071,642 | A | 12/1991 | Lahr et al. |
| 5,072,070 | A | 12/1991 | Balsells |
| 5,079,388 | A | 1/1992 | Balsells |
| 5,091,188 | A | 2/1992 | Haynes |
| 5,108,078 | A * | 4/1992 | Balsells .......... F16F 1/04 267/1.5 |
| 5,110,596 | A | 5/1992 | Magruder et al. |
| 5,112,614 | A | 5/1992 | Magruder et al. |
| 5,113,938 | A | 5/1992 | Clayton |
| 5,117,066 | A | 5/1992 | Balsells |
| D326,718 | S | 6/1992 | Maxwell |
| 5,118,666 | A | 6/1992 | Habener |
| 5,120,306 | A | 6/1992 | Gosselin |
| 5,120,712 | A | 6/1992 | Habener |
| 5,120,832 | A | 6/1992 | Goeddel et al. |
| 5,122,128 | A | 6/1992 | Cardinal et al. |
| 5,122,377 | A | 6/1992 | Miller |
| 5,126,142 | A | 6/1992 | Ayer et al. |

(56) References Cited

U.S. PATENT DOCUMENTS

| | | |
|---|---|---|
| 5,126,147 A | 6/1992 | Silvestri et al. |
| 5,134,244 A | 7/1992 | Balsells |
| 5,137,727 A | 8/1992 | Eckenhoff |
| 5,151,093 A | 9/1992 | Theeuwes et al. |
| 5,160,122 A | 11/1992 | Balsells |
| 5,160,743 A | 11/1992 | Edgren et al. |
| 5,161,806 A | 11/1992 | Balsells |
| 5,180,591 A | 1/1993 | Margruder et al. |
| 5,190,765 A | 3/1993 | Jao et al. |
| 5,203,849 A | 4/1993 | Balsells |
| 5,204,108 A | 4/1993 | Illum |
| 5,207,752 A | 5/1993 | Sorensen et al. |
| 5,209,746 A | 5/1993 | Balaban et al. |
| 5,213,809 A | 5/1993 | Wright et al. |
| 5,213,810 A | 5/1993 | Steber |
| 5,221,278 A | 6/1993 | Linkwitz et al. |
| 5,223,265 A | 6/1993 | Wong |
| 5,225,205 A | 7/1993 | Orsolini |
| 5,231,176 A | 7/1993 | Goeddel et al. |
| 5,234,424 A | 8/1993 | Yum et al. |
| 5,234,692 A | 8/1993 | Magruder et al. |
| 5,234,693 A | 8/1993 | Magruder et al. |
| 5,234,695 A | 8/1993 | Hobbs et al. |
| 5,252,338 A | 10/1993 | Jao et al. |
| 5,260,069 A | 11/1993 | Chen |
| 5,278,151 A | 1/1994 | Korb et al. |
| 5,279,608 A | 1/1994 | Cherif Cheikh |
| 5,284,655 A | 2/1994 | Bogdansky et al. |
| 5,288,501 A | 2/1994 | Nürnberg et al. |
| 5,288,502 A | 2/1994 | Mcginity et al. |
| 5,290,271 A | 3/1994 | Jernberg |
| 5,300,079 A | 4/1994 | Niezink et al. |
| 5,300,302 A | 4/1994 | Tachon et al. |
| 5,308,348 A | 5/1994 | Balaban et al. |
| 5,312,335 A | 5/1994 | McKinnon et al. |
| 5,312,389 A | 5/1994 | Theeuwes et al. |
| 5,312,390 A | 5/1994 | Wong |
| 5,318,558 A | 6/1994 | Linkwitz et al. |
| 5,318,780 A | 6/1994 | Viegas et al. |
| 5,320,616 A | 6/1994 | Magndu et al. |
| 5,324,280 A | 6/1994 | Wong et al. |
| 5,336,057 A | 8/1994 | Fukuda et al. |
| 5,336,505 A | 8/1994 | Ng et al. |
| 5,352,662 A | 10/1994 | Brooks et al. |
| 5,368,588 A | 11/1994 | Bettinger |
| 5,368,863 A | 11/1994 | Eckenhoff et al. |
| 5,371,089 A | 12/1994 | Rattan |
| 5,374,620 A | 12/1994 | Clark et al. |
| 5,385,738 A | 1/1995 | Yamahira et al. |
| 5,385,887 A | 1/1995 | Yim et al. |
| 5,407,609 A | 4/1995 | Tice et al. |
| D358,644 S | 5/1995 | Park |
| 5,411,951 A | 5/1995 | Mitchell |
| 5,413,572 A | 5/1995 | Wong et al. |
| 5,413,672 A | 5/1995 | Hirotsuji et al. |
| 5,424,236 A | 6/1995 | Eng |
| 5,424,286 A | 6/1995 | Eng |
| 5,428,024 A | 6/1995 | Chu et al. |
| 5,429,602 A | 7/1995 | Hauser |
| 5,439,688 A | 8/1995 | Orsolini et al. |
| 5,443,459 A | 8/1995 | Wong et al. |
| 5,445,829 A | 8/1995 | Paradissis et al. |
| 5,456,679 A | 10/1995 | Balaban et al. |
| 5,458,888 A | 10/1995 | Chen |
| 5,464,929 A | 11/1995 | Bezwada et al. |
| 5,472,708 A | 12/1995 | Chen |
| 5,478,564 A | 12/1995 | Wantier et al. |
| 5,486,365 A | 1/1996 | Takado et al. |
| 5,498,255 A | 3/1996 | Wong et al. |
| 5,511,355 A | 4/1996 | Dingler |
| 5,512,293 A | 4/1996 | Landrau et al. |
| 5,512,549 A | 4/1996 | Chen et al. |
| 5,514,110 A | 5/1996 | Teh |
| 5,529,914 A | 6/1996 | Hubbell et al. |
| 5,531,736 A | 7/1996 | Wong et al. |
| 5,540,665 A | 7/1996 | Mercado et al. |
| 5,540,912 A | 7/1996 | Roorda et al. |
| 5,541,172 A | 7/1996 | Labrie et al. |
| 5,542,682 A * | 8/1996 | Goldstein ............ F16J 15/3212 267/1.5 |
| 5,543,156 A | 8/1996 | Roorda et al. |
| 5,545,618 A | 8/1996 | Buckley et al. |
| 5,556,642 A | 9/1996 | Kobayashi et al. |
| 5,557,318 A | 9/1996 | Gabriel |
| 5,571,525 A | 11/1996 | Roorda et al. |
| 5,574,008 A | 11/1996 | Johnson et al. |
| 5,574,137 A | 11/1996 | Gray et al. |
| 5,580,578 A | 12/1996 | Oshlack et al. |
| 5,589,167 A | 12/1996 | Cleland et al. |
| 5,595,751 A | 1/1997 | Bezwada |
| 5,595,759 A | 1/1997 | Wright et al. |
| 5,597,579 A | 1/1997 | Bezwada et al. |
| 5,602,010 A | 2/1997 | Hauptmann et al. |
| 5,605,688 A | 2/1997 | Himmler et al. |
| 5,607,687 A | 3/1997 | Bezwada et al. |
| 5,609,885 A | 3/1997 | Rivera et al. |
| 5,614,221 A | 3/1997 | Fjellstrom |
| 5,614,492 A | 3/1997 | Habener |
| 5,618,552 A | 4/1997 | Bezwada et al. |
| 5,620,698 A | 4/1997 | Bezwada et al. |
| 5,620,705 A | 4/1997 | Dong et al. |
| 5,630,796 A | 5/1997 | Bellhouse et al. |
| 5,633,011 A | 5/1997 | Dong et al. |
| 5,635,213 A | 6/1997 | Nystrom et al. |
| 5,639,477 A | 6/1997 | Maruyama et al. |
| 5,639,640 A | 6/1997 | Reddy et al. |
| 5,645,850 A | 7/1997 | Bezwada et al. |
| 5,648,088 A | 7/1997 | Bezwada et al. |
| 5,650,173 A | 7/1997 | Ramstack et al. |
| 5,654,008 A | 8/1997 | Herbert et al. |
| 5,654,010 A | 8/1997 | Johnson et al. |
| 5,656,297 A | 8/1997 | Bernstein et al. |
| 5,656,299 A | 8/1997 | Kino et al. |
| 5,658,593 A | 8/1997 | Orly et al. |
| 5,660,847 A | 8/1997 | Magruder et al. |
| 5,660,858 A | 8/1997 | Parikh et al. |
| 5,660,861 A | 8/1997 | Jao et al. |
| 5,667,808 A | 9/1997 | Johnson et al. |
| 5,668,170 A | 9/1997 | Gyory |
| 5,672,549 A | 9/1997 | Minami et al. |
| 5,676,942 A | 10/1997 | Testa et al. |
| 5,683,801 A | 11/1997 | Mesens et al. |
| 5,686,097 A | 11/1997 | Taskovich et al. |
| 5,690,925 A | 11/1997 | Gray et al. |
| 5,690,952 A | 11/1997 | Magruder et al. |
| 5,698,213 A | 12/1997 | Jamiolkowski et al. |
| 5,700,486 A | 12/1997 | Canal et al. |
| 5,700,583 A | 12/1997 | Jamiolkowski et al. |
| 5,703,200 A | 12/1997 | Bezwada et al. |
| 5,707,644 A | 1/1998 | Illum |
| 5,711,967 A | 1/1998 | Juch |
| 5,713,847 A | 2/1998 | Howard, III et al. |
| 5,718,922 A | 2/1998 | Herrero-Vanrell |
| 5,728,088 A | 3/1998 | Margruder et al. |
| 5,728,396 A | 3/1998 | Peery et al. |
| 5,733,572 A | 3/1998 | Unger et al. |
| 5,736,159 A | 4/1998 | Chen et al. |
| 5,738,845 A | 4/1998 | Imakawa |
| 5,747,058 A | 5/1998 | Tipton et al. |
| 5,756,450 A | 5/1998 | Lorenz et al. |
| 5,767,251 A | 6/1998 | Reddy et al. |
| 5,770,231 A | 6/1998 | Mesens et al. |
| 5,782,396 A | 7/1998 | Mastri et al. |
| 5,792,477 A | 8/1998 | Rickey et al. |
| 5,795,591 A | 8/1998 | Lee et al. |
| 5,795,779 A | 8/1998 | McCormick et al. |
| 5,807,876 A | 9/1998 | Armistead et al. |
| 5,814,323 A | 9/1998 | Lyle |
| 5,817,129 A | 10/1998 | Labrecque et al. |
| 5,830,501 A | 11/1998 | Dong et al. |
| 5,836,935 A | 11/1998 | Ashton et al. |
| 5,843,891 A | 12/1998 | Sherman |
| 5,844,017 A | 12/1998 | Jamiolkowski et al. |
| 5,851,451 A | 12/1998 | Takechi et al. |

(56) References Cited

U.S. PATENT DOCUMENTS

| | | |
|---|---|---|
| 5,858,746 A | 1/1999 | Hubbell et al. |
| 5,859,150 A | 1/1999 | Jamiolkowski et al. |
| 5,861,166 A | 1/1999 | Eckenhoff |
| 5,871,770 A | 2/1999 | Margruder et al. |
| 5,871,778 A | 2/1999 | Kino et al. |
| 5,874,388 A | 2/1999 | Hsu |
| 5,876,746 A | 3/1999 | Jona et al. |
| 5,882,676 A | 3/1999 | Lee et al. |
| D408,917 S | 4/1999 | Hacker |
| 5,904,935 A | 5/1999 | Eckenhoff et al. |
| 5,906,816 A | 5/1999 | Soos et al. |
| 5,906,830 A | 5/1999 | Farinas et al. |
| 5,908,621 A | 6/1999 | Glue et al. |
| 5,916,598 A | 6/1999 | Rickey et al. |
| 5,922,253 A | 7/1999 | Herbert et al. |
| 5,928,666 A | 7/1999 | Farinas et al. |
| 5,932,547 A | 8/1999 | Stevenson et al. |
| 5,938,654 A | 8/1999 | Wong et al. |
| 5,939,286 A | 8/1999 | Johnson et al. |
| 5,942,223 A | 8/1999 | Bazer et al. |
| 5,942,253 A | 8/1999 | Gombotz et al. |
| 5,945,126 A | 8/1999 | Thanoo et al. |
| 5,948,430 A | 9/1999 | Zerbe et al. |
| 5,958,909 A | 9/1999 | Habener |
| 5,962,023 A | 10/1999 | Jamiolkowski et al. |
| 5,965,168 A | 10/1999 | Mesens et al. |
| 5,972,370 A | 10/1999 | Eckenhoff et al. |
| 5,972,373 A | 10/1999 | Yajima et al. |
| 5,976,109 A | 11/1999 | Heruth |
| 5,980,945 A | 11/1999 | Ruiz |
| 5,981,719 A | 11/1999 | Woiszwillo et al. |
| 5,984,890 A | 11/1999 | Gast et al. |
| 5,985,305 A | 11/1999 | Peery et al. |
| 5,989,463 A | 11/1999 | Tracy et al. |
| 5,997,527 A | 12/1999 | Gumucio et al. |
| 5,997,902 A | 12/1999 | Maruyama et al. |
| 6,007,805 A | 12/1999 | Foster et al. |
| 6,017,545 A | 1/2000 | Modi |
| 6,022,561 A | 2/2000 | Carlsson et al. |
| 6,029,361 A | 2/2000 | Newman |
| 6,056,718 A | 5/2000 | Funderburk et al. |
| 6,060,450 A | 5/2000 | Soos et al. |
| 6,069,133 A | 5/2000 | Carlo et al. |
| 6,074,660 A | 6/2000 | Jamiolkowski et al. |
| 6,074,673 A | 6/2000 | Guillen |
| 6,100,346 A | 8/2000 | Jamiolkowski et al. |
| 6,110,503 A | 8/2000 | Rickey et al. |
| 6,113,938 A | 9/2000 | Chen et al. |
| 6,113,947 A | 9/2000 | Cleland et al. |
| 6,120,787 A | 9/2000 | Gustafsson et al. |
| 6,124,261 A | 9/2000 | Stevenson et al. |
| 6,124,281 A | 9/2000 | Lewis et al. |
| 6,127,520 A | 10/2000 | Ueda et al. |
| 6,129,761 A | 10/2000 | Hubbell |
| 6,130,200 A | 10/2000 | Brodbeck et al. |
| 6,132,420 A | 10/2000 | Dionne et al. |
| 6,133,249 A | 10/2000 | Hills |
| 6,133,429 A | 10/2000 | Davis et al. |
| 6,147,168 A | 11/2000 | Jamiolkowski et al. |
| 6,156,331 A | 12/2000 | Peery et al. |
| 6,172,046 B1 | 1/2001 | Albrecht |
| 6,174,547 B1 | 1/2001 | Dong et al. |
| 6,177,096 B1 | 1/2001 | Zerbe et al. |
| 6,183,461 B1 | 2/2001 | Matsuura et al. |
| 6,187,095 B1 | 2/2001 | Labrecque et al. |
| 6,190,350 B1 | 2/2001 | Davis et al. |
| 6,190,700 B1 | 2/2001 | Okada et al. |
| 6,190,702 B1 | 2/2001 | Takada et al. |
| 6,191,102 B1 | 2/2001 | DiMarchi et al. |
| 6,204,022 B1 | 3/2001 | Johnson et al. |
| 6,217,893 B1 | 4/2001 | Pellet et al. |
| 6,217,906 B1 | 4/2001 | Gumucio et al. |
| 6,217,908 B1 | 4/2001 | Mathiowitz et al. |
| 6,218,431 B1 | 4/2001 | Schoen et al. |
| 6,224,894 B1 | 5/2001 | Jamiolkowski et al. |
| 6,235,712 B1 | 5/2001 | Stevenson et al. |
| 6,245,349 B1 | 6/2001 | Yiv et al. |
| 6,245,357 B1 | 6/2001 | Edgren et al. |
| 6,248,112 B1 | 6/2001 | Gambale et al. |
| 6,251,435 B1 | 6/2001 | Jamiolkowski et al. |
| 6,258,377 B1 | 7/2001 | New et al. |
| 6,261,584 B1 | 7/2001 | Peery et al. |
| 6,268,343 B1 | 7/2001 | Knudsen et al. |
| 6,270,700 B1 | 8/2001 | Ignatious |
| 6,270,787 B1 | 8/2001 | Ayer |
| 6,277,413 B1 | 8/2001 | Sankaram |
| 6,283,949 B1 | 9/2001 | Roorda |
| 6,284,264 B1 | 9/2001 | Zerbe et al. |
| 6,284,727 B1 | 9/2001 | Kim et al. |
| 6,287,295 B1 | 9/2001 | Chen et al. |
| 6,284,725 B1 | 12/2001 | Coolidge et al. |
| 6,329,336 B1 | 12/2001 | Bridon et al. |
| 6,331,311 B1 | 12/2001 | Brodbeck et al. |
| 6,372,218 B1 | 4/2002 | Cummins, Jr. |
| 6,372,256 B2 | 4/2002 | Jamiolkowski et al. |
| 6,375,978 B1 | 4/2002 | Kleiner et al. |
| 6,395,292 B2 | 5/2002 | Peery et al. |
| 6,403,655 B1 | 6/2002 | Bezwada et al. |
| 6,419,952 B2 | 7/2002 | Wong et al. |
| 6,433,144 B1 | 8/2002 | Morris et al. |
| 6,436,091 B1 | 8/2002 | Harper et al. |
| 6,447,522 B2 | 9/2002 | Gambale et al. |
| 6,451,974 B1 | 9/2002 | Hansen |
| 6,458,385 B2 | 10/2002 | Jamiolkowski et al. |
| 6,458,387 B1 | 10/2002 | Scott et al. |
| 6,458,924 B2 | 10/2002 | Knudsen et al. |
| 6,461,605 B1 | 10/2002 | Cutler et al. |
| 6,464,688 B1 | 10/2002 | Harper et al. |
| 6,468,961 B1 | 10/2002 | Brodbeck et al. |
| 6,471,688 B1 | 10/2002 | Harper et al. |
| 6,472,512 B1 | 10/2002 | LaFleur et al. |
| 6,485,706 B1 | 11/2002 | McCoy et al. |
| 6,495,164 B1 | 12/2002 | Ramstack et al. |
| 6,506,724 B1 | 1/2003 | Hiles et al. |
| 6,508,808 B1 | 1/2003 | Carr et al. |
| 6,514,500 B1 | 2/2003 | Bridon et al. |
| 6,514,517 B2 | 2/2003 | Jamilolkowski et al. |
| 6,524,305 B1 * | 2/2003 | Peterson .............. A61K 9/0004 424/422 |
| 6,528,093 B1 | 3/2003 | Kamei et al. |
| 6,528,486 B1 | 3/2003 | Larsen et al. |
| 6,541,021 B1 | 4/2003 | Johnson et al. |
| 6,544,252 B1 | 4/2003 | Theeuwes et al. |
| 6,547,250 B1 * | 4/2003 | Noble .................. F04B 53/143 277/309 |
| 6,551,613 B1 | 4/2003 | Dong et al. |
| 6,569,420 B2 | 5/2003 | Chen et al. |
| 6,572,890 B2 | 6/2003 | Faour et al. |
| 6,579,851 B2 | 6/2003 | Goeke et al. |
| 6,592,887 B2 | 7/2003 | Zerbe et al. |
| 6,593,295 B2 | 7/2003 | Bridon et al. |
| 6,635,268 B2 | 10/2003 | Peery et al. |
| 6,667,061 B2 | 12/2003 | Ramstack et al. |
| 6,670,368 B1 | 12/2003 | Breault et al. |
| 6,673,767 B1 | 1/2004 | Brodbeck et al. |
| 6,682,522 B2 | 1/2004 | Carr et al. |
| 6,703,225 B1 | 3/2004 | Kojima et al. |
| 6,703,359 B1 | 3/2004 | Young et al. |
| 6,706,689 B2 | 3/2004 | Coolidge et al. |
| 6,709,671 B2 | 3/2004 | Zerbe et al. |
| 6,720,407 B1 | 4/2004 | Hughes et al. |
| 6,730,328 B2 | 5/2004 | Maskiwicz et al. |
| 6,767,887 B2 | 7/2004 | Hoffmann et al. |
| 6,821,949 B2 | 11/2004 | Bridon et al. |
| 6,833,256 B1 | 12/2004 | Pontzer et al. |
| 6,835,194 B2 | 12/2004 | Johnson et al. |
| 6,840,931 B1 | 1/2005 | Peterson et al. |
| 6,849,708 B1 | 2/2005 | Habener |
| 6,849,714 B1 | 2/2005 | Bridon et al. |
| 6,858,576 B1 | 2/2005 | Young et al. |
| 6,872,700 B1 | 3/2005 | Young et al. |
| 6,875,748 B2 | 4/2005 | Manthorpe et al. |
| 6,887,470 B1 | 5/2005 | Bridon et al. |
| 6,887,849 B2 | 5/2005 | Bridon et al. |

(56) References Cited

U.S. PATENT DOCUMENTS

| | | | |
|---|---|---|---|
| 6,899,887 B2 | 5/2005 | Ayer |
| 6,899,898 B2 | 5/2005 | Albayrak |
| 6,902,744 B1 | 6/2005 | Kolterman et al. |
| 6,903,186 B1 | 6/2005 | Dong |
| 6,913,767 B1 | 7/2005 | Cleland et al. |
| 6,923,800 B2 | 8/2005 | Chen et al. |
| 6,924,264 B1 | 8/2005 | Prickett et al. |
| 6,939,556 B2 | 9/2005 | Lautenbach |
| 6,956,026 B2 | 10/2005 | Beeley et al. |
| 6,969,702 B2 | 11/2005 | Bertilsson et al. |
| 6,976,981 B2 | 12/2005 | Ayer |
| 6,989,366 B2 | 1/2006 | Beeley et al. |
| 6,992,065 B2 | 1/2006 | Okumu |
| 6,997,922 B2 | 2/2006 | Theeuwes et al. |
| 7,014,636 B2 | 3/2006 | Gilbert |
| 7,022,674 B2 | 4/2006 | DeFelippis et al. |
| 7,041,646 B2 | 5/2006 | Pan et al. |
| 7,074,423 B2 | 7/2006 | Fereira et al. |
| 7,084,243 B2 | 8/2006 | Glaesner et al. |
| 7,101,567 B1 | 9/2006 | Sano et al. |
| 7,101,843 B2 | 9/2006 | Glaesner et al. |
| 7,112,335 B2 | 9/2006 | Lautenbach |
| 7,115,569 B2 | 10/2006 | Beeley et al. |
| 7,138,375 B2 | 11/2006 | Beeley et al. |
| 7,138,486 B2 | 11/2006 | Habener et al. |
| 7,141,547 B2 | 11/2006 | Rosen et al. |
| 7,144,863 B2 | 12/2006 | DeFelippis et al. |
| 7,153,825 B2 | 12/2006 | Young et al. |
| 7,157,555 B1 | 1/2007 | Beeley et al. |
| 7,163,688 B2 | 1/2007 | Peery et al. |
| 7,163,697 B2 | 1/2007 | Hanes et al. |
| 7,199,217 B2 | 4/2007 | DiMarchi et al. |
| 7,205,409 B2 | 4/2007 | Pei et al. |
| 7,207,982 B2 | 4/2007 | Dionne et al. |
| 7,241,457 B2 | 7/2007 | Chen et al. |
| 7,258,869 B1 | 8/2007 | Berry et al. |
| 7,297,761 B2 | 11/2007 | Beeley et al. |
| 7,316,680 B2 | 1/2008 | Gilbert |
| 7,393,827 B2 | 7/2008 | Nadler |
| 7,407,499 B2 | 8/2008 | Trautman |
| 7,442,682 B2 | 10/2008 | Kitaura et al. |
| 7,456,254 B2 | 11/2008 | Wright et al. |
| 7,459,432 B2 | 12/2008 | Cowley et al. |
| 7,521,423 B2 | 4/2009 | Young et al. |
| 7,563,871 B2 | 7/2009 | Wright et al. |
| 7,589,169 B2 | 9/2009 | Bolotin |
| 7,612,176 B2 | 11/2009 | Wright et al. |
| 7,635,463 B2 | 12/2009 | Bolotin et al. |
| 7,655,254 B2 | 2/2010 | Dennis et al. |
| 7,655,257 B2 | 2/2010 | Peery et al. |
| 7,666,835 B2 | 2/2010 | Bloom et al. |
| 7,682,356 B2 * | 3/2010 | Alessi | A61K 9/0004 604/222 |
| 7,727,519 B2 | 6/2010 | Moran |
| 7,731,947 B2 | 6/2010 | Eliaz et al. |
| 7,736,665 B2 | 6/2010 | Patel et al. |
| 7,741,269 B2 | 6/2010 | Young et al. |
| 7,790,140 B2 | 9/2010 | Bolotin |
| 7,825,091 B2 | 11/2010 | Bloom et al. |
| 7,829,109 B2 | 11/2010 | Chen et al. |
| 7,833,543 B2 | 11/2010 | Gilson et al. |
| 7,879,028 B2 * | 2/2011 | Alessi | A61K 9/0004 604/222 |
| 7,879,794 B2 | 4/2011 | Berry et al. |
| 7,919,109 B2 | 4/2011 | Berry et al. |
| 7,928,065 B2 | 6/2011 | Rohloff et al. |
| 7,964,183 B2 | 6/2011 | Eliaz et al. |
| 8,039,432 B2 | 10/2011 | Bridon et al. |
| 7,959,938 B2 | 11/2011 | Lautenbach et al. |
| 8,048,438 B2 | 11/2011 | Berry et al. |
| 8,052,996 B2 | 11/2011 | Lautenbach et al. |
| 8,058,233 B2 | 11/2011 | Cowley et al. |
| 8,101,576 B2 | 1/2012 | Bloom |
| 8,114,430 B2 | 2/2012 | Rohloff et al. |
| 8,114,437 B2 | 2/2012 | Rohloff et al. |
| 8,158,150 B2 | 4/2012 | Lautenbach et al. |
| 8,173,150 B2 | 5/2012 | Berry et al. |
| 8,202,836 B2 | 6/2012 | Rohloff et al. |
| 8,206,745 B2 | 6/2012 | Rohloff et al. |
| 8,211,467 B2 | 7/2012 | Rohloff et al. |
| 8,217,001 B2 | 7/2012 | Cowley et al. |
| 8,231,859 B2 | 7/2012 | Bolotin et al. |
| 8,257,682 B2 | 9/2012 | Bolotin et al. |
| 8,257,691 B2 | 9/2012 | Eliaz et al. |
| 8,262,667 B1 | 9/2012 | Silver et al. |
| 8,263,545 B2 | 9/2012 | Bloom |
| 8,263,736 B2 | 9/2012 | Berry |
| 8,268,341 B2 | 9/2012 | Berry |
| 8,273,365 B2 | 9/2012 | Lautenbach et al. |
| 8,273,713 B2 | 9/2012 | Pittner et al. |
| D669,589 S | 10/2012 | Delaey |
| 8,277,776 B2 | 10/2012 | Bolotin et al. |
| 8,278,267 B2 | 10/2012 | Weyer et al. |
| 8,288,338 B2 | 10/2012 | Alessi et al. |
| 8,298,561 B2 | 10/2012 | Alessi et al. |
| 8,299,025 B2 | 10/2012 | Alessi et al. |
| 8,343,140 B2 | 1/2013 | Alessi et al. |
| 8,367,095 B2 | 2/2013 | Lautenbach et al. |
| 8,372,424 B2 | 2/2013 | Berry et al. |
| 8,398,967 B2 | 3/2013 | Eliaz et al. |
| 8,440,226 B2 | 5/2013 | Rohloff et al. |
| 8,460,694 B2 | 6/2013 | Rohloff et al. |
| 8,470,353 B2 | 6/2013 | Lautenbach et al. |
| 8,801,700 B2 * | 8/2014 | Alessi | A61K 9/0004 604/222 |
| 8,865,202 B2 | 10/2014 | Zerbe et al. |
| 8,888,745 B2 | 11/2014 | Van Der Graaf et al. |
| 8,926,595 B2 | 1/2015 | Alessi et al. |
| 8,940,316 B2 | 1/2015 | Alessi et al. |
| 8,992,961 B2 | 3/2015 | Lautenbach et al. |
| 8,992,962 B2 | 3/2015 | Lautenbach et al. |
| 9,044,209 B2 | 6/2015 | Dayton et al. |
| 9,078,900 B2 | 7/2015 | Kuzma et al. |
| 9,095,553 B2 | 8/2015 | Rohloff et al. |
| 9,526,763 B2 | 12/2016 | Rohloff et al. |
| 9,539,200 B2 | 1/2017 | Lautenbach |
| 9,572,889 B2 | 2/2017 | Alessi et al. |
| 9,682,127 B2 | 6/2017 | Alessi et al. |
| 9,889,085 B1 | 2/2018 | Alessi et al. |
| 2001/0012511 A1 | 8/2001 | Bezwada et al. |
| 2001/0021377 A1 | 9/2001 | Jamiolkowski et al. |
| 2001/0021822 A1 | 9/2001 | Ayer |
| 2001/0022974 A1 | 9/2001 | Ayer |
| 2001/0026793 A1 | 10/2001 | Jamiolkowski et al. |
| 2001/0027311 A1 | 10/2001 | Chen et al. |
| 2001/0036472 A1 | 11/2001 | Wong et al. |
| 2001/0037190 A1 | 11/2001 | Beisswenger |
| 2001/0040326 A1 * | 11/2001 | Balczun | F16C 27/063 267/141 |
| 2002/0001631 A1 | 1/2002 | Okumu |
| 2002/0004481 A1 | 1/2002 | Cleland et al. |
| 2002/0012818 A1 | 1/2002 | Ruppi et al. |
| 2002/0034532 A1 | 3/2002 | Brodbeck et al. |
| 2002/0037309 A1 | 3/2002 | Jamiolkowski et al. |
| 2002/0048600 A1 | 4/2002 | Bhatt et al. |
| 2002/0098180 A1 | 7/2002 | Lei |
| 2002/0136848 A1 | 9/2002 | Yoshii et al. |
| 2002/0137666 A1 | 9/2002 | Beeley et al. |
| 2002/0141985 A1 | 10/2002 | Pittner et al. |
| 2002/0197185 A1 | 12/2002 | Jamiolkowski et al. |
| 2002/0197235 A1 | 12/2002 | Moran |
| 2003/0032947 A1 | 2/2003 | Harper et al. |
| 2003/0044467 A1 | 3/2003 | Brodbeck et al. |
| 2003/0045454 A1 | 3/2003 | Okumu et al. |
| 2003/0059376 A1 | 3/2003 | Libbey et al. |
| 2003/0060425 A1 | 3/2003 | Ahlem et al. |
| 2003/0097121 A1 | 6/2003 | Babcock et al. |
| 2003/0104063 A1 | 6/2003 | Babcock et al. |
| 2003/0108608 A1 | 6/2003 | Berry et al. |
| 2003/0108609 A1 | 6/2003 | Berry et al. |
| 2003/0113380 A1 | 6/2003 | Ramstack et al. |
| 2003/0118660 A1 | 6/2003 | Rickey et al. |
| 2003/0114837 A1 | 7/2003 | Drustrup |
| 2003/0138403 A1 | 7/2003 | Drustrup |

(56) References Cited

U.S. PATENT DOCUMENTS

| | | |
|---|---|---|
| 2003/0138491 A1 | 7/2003 | Tracy et al. |
| 2003/0157178 A1 | 8/2003 | Chen et al. |
| 2003/0170289 A1 | 9/2003 | Chen et al. |
| 2003/0180364 A1 | 9/2003 | Chen et al. |
| 2003/0186858 A1 | 10/2003 | Arentsen |
| 2003/0191099 A1 | 10/2003 | Bohlmann et al. |
| 2003/0211974 A1 | 11/2003 | Brodbeck et al. |
| 2003/0215515 A1 | 11/2003 | Truong-Le et al. |
| 2004/0001689 A1 | 1/2004 | Goldsmith et al. |
| 2004/0001889 A1 | 1/2004 | Chen et al. |
| 2004/0002442 A1 | 1/2004 | Pan et al. |
| 2004/0022859 A1 | 2/2004 | Chen et al. |
| 2004/0024068 A1 | 2/2004 | Chen et al. |
| 2004/0024069 A1 | 2/2004 | Chen et al. |
| 2004/0029784 A1 | 2/2004 | Hathaway |
| 2004/0039376 A1 | 2/2004 | Peery et al. |
| 2004/0157951 A1 | 3/2004 | Glaesner et al. |
| 2004/0097906 A1 | 5/2004 | Fereira et al. |
| 2004/0101557 A1 | 5/2004 | Gibson et al. |
| 2004/0102762 A1 | 5/2004 | Gilbert |
| 2004/0115236 A1 | 6/2004 | Chan et al. |
| 2004/0142867 A1 | 7/2004 | Oi et al. |
| 2004/0142902 A1 | 8/2004 | Chen et al. |
| 2004/0151753 A1 | 8/2004 | Chen et al. |
| 2004/0198654 A1 | 10/2004 | Glaesner et al. |
| 2004/0209801 A1 | 10/2004 | Berry et al. |
| 2004/0224903 A1 | 11/2004 | Berry et al. |
| 2004/0225113 A1 | 11/2004 | LaFleur et al. |
| 2004/0243106 A1 | 12/2004 | Ayer |
| 2004/0265273 A1 | 12/2004 | Li et al. |
| 2004/0266683 A1 | 12/2004 | Hathaway et al. |
| 2004/0266692 A1 | 12/2004 | Young et al. |
| 2005/0004557 A1 | 1/2005 | Russell |
| 2005/0008661 A1 | 1/2005 | Fereira et al. |
| 2005/0009742 A1 | 1/2005 | Bertilsson et al. |
| 2005/0010196 A1 | 1/2005 | Fereira et al. |
| 2005/0070883 A1 | 3/2005 | Brown et al. |
| 2005/0070927 A1 | 3/2005 | Feinberg |
| 2005/0079200 A1 | 4/2005 | Rathenow et al. |
| 2005/0079202 A1 | 4/2005 | Chen et al. |
| 2005/0095284 A1 | 5/2005 | Trautman |
| 2005/0101942 A1 | 5/2005 | Gillis et al. |
| 2005/0101943 A1 | 5/2005 | Ayer et al. |
| 2005/0106214 A1 | 5/2005 | Chen |
| 2005/0112188 A1 | 5/2005 | Eliaz et al. |
| 2005/0118206 A1 | 6/2005 | Luk et al. |
| 2005/0131386 A1 | 6/2005 | Freeman et al. |
| 2005/0131389 A1 | 8/2005 | Pan et al. |
| 2005/0175701 A1 | 8/2005 | Pan et al. |
| 2005/0201980 A1 | 9/2005 | Moran |
| 2005/0215475 A1 | 9/2005 | Ong et al. |
| 2005/0216087 A1 | 9/2005 | Zucherman, Jr. et al. |
| 2005/0266087 A1 | 12/2005 | Junnarkar et al. |
| 2005/0271702 A1 | 12/2005 | Wright et al. |
| 2005/0276856 A1 | 12/2005 | Fereira et al. |
| 2005/0281879 A1 | 12/2005 | Chen et al. |
| 2006/0013879 A9 | 1/2006 | Brodbeck et al. |
| 2006/0014678 A1 | 1/2006 | Cowley et al. |
| 2006/0030526 A1 | 2/2006 | Liu et al. |
| 2006/0069029 A1 | 3/2006 | Kolterman et al. |
| 2006/0073182 A1 | 4/2006 | Wong et al. |
| 2006/0084604 A1 | 4/2006 | Kitaura et al. |
| 2006/0084922 A1 | 4/2006 | Botha |
| 2006/0094652 A1 | 5/2006 | Levy et al. |
| 2006/0094693 A1 | 5/2006 | Aziz et al. |
| 2006/0106399 A1 | 5/2006 | Taras et al. |
| 2006/0141040 A1 | 6/2006 | Chen et al. |
| 2006/0142234 A1 | 6/2006 | Chen et al. |
| 2006/0160736 A1 | 7/2006 | Nadler |
| 2006/0178304 A1 | 8/2006 | Juul-Mortensen et al. |
| 2006/0178643 A1* | 8/2006 | Sudo ............... A61M 5/31511 604/230 |
| 2006/0193918 A1* | 8/2006 | Rohloff ............... A61K 9/0004 424/486 |
| 2006/0216242 A1 | 9/2006 | Rohloff et al. |
| 2006/0224145 A1* | 10/2006 | Gillis ............... A61F 2/02 604/891.1 |
| 2006/0233841 A1 | 10/2006 | Brodbeck et al. |
| 2006/0246138 A1 | 11/2006 | Rohloff et al. |
| 2006/0251618 A1 | 11/2006 | Dennis et al. |
| 2006/0263433 A1 | 11/2006 | Ayer et al. |
| 2006/0264890 A1* | 11/2006 | Moberg ............ A61M 5/1413 604/500 |
| 2006/0280795 A1 | 12/2006 | Penhasi et al. |
| 2006/0293232 A1 | 12/2006 | Levy et al. |
| 2007/0027105 A1 | 2/2007 | Junnarkar et al. |
| 2007/0149011 A1* | 6/2007 | Kent .................. H01R 13/508 439/120 |
| 2007/0166352 A1 | 7/2007 | Wright et al. |
| 2007/0248572 A1 | 10/2007 | Moran et al. |
| 2007/0281024 A1 | 12/2007 | Lautenbach et al. |
| 2008/0020016 A1 | 1/2008 | Li et al. |
| 2008/0038316 A1 | 2/2008 | Wong et al. |
| 2008/0064636 A1 | 3/2008 | Bloom et al. |
| 2008/0065090 A1 | 3/2008 | Scribner et al. |
| 2008/0091176 A1 | 4/2008 | Alessi et al. |
| 2008/0110515 A1 | 5/2008 | Angelosanto et al. |
| 2008/0112994 A1 | 5/2008 | Junnarkar et al. |
| 2008/0200383 A1 | 8/2008 | Jennings et al. |
| 2008/0207512 A1 | 8/2008 | Roth et al. |
| 2008/0226625 A1 | 9/2008 | Berry et al. |
| 2008/0226689 A1 | 9/2008 | Berry et al. |
| 2008/0260838 A1 | 10/2008 | Hokenson et al. |
| 2008/0260840 A1 | 10/2008 | Alessi et al. |
| 2008/0269725 A1 | 10/2008 | Deem et al. |
| 2008/0312157 A1 | 12/2008 | Levy et al. |
| 2009/0022727 A1 | 1/2009 | Houston et al. |
| 2009/0035253 A1* | 2/2009 | Wright .............. A61K 9/0024 424/85.2 |
| 2009/0036364 A1 | 2/2009 | Levy et al. |
| 2009/0042781 A1 | 2/2009 | Petersen et al. |
| 2009/0074734 A1 | 3/2009 | Rottiers |
| 2009/0087408 A1 | 4/2009 | Berry et al. |
| 2009/0156474 A1 | 6/2009 | Roth et al. |
| 2009/0163447 A1 | 6/2009 | Maggio |
| 2009/0186817 A1 | 7/2009 | Ghosh et al. |
| 2009/0202481 A1 | 8/2009 | Li et al. |
| 2009/0202608 A1 | 8/2009 | Alessi et al. |
| 2009/0209460 A1 | 8/2009 | Young et al. |
| 2009/0210019 A1 | 8/2009 | Kim et al. |
| 2009/0215694 A1 | 8/2009 | Kolterman et al. |
| 2009/0234392 A1 | 9/2009 | Dziedzic |
| 2009/0247463 A1 | 10/2009 | Wright et al. |
| 2009/0254143 A1 | 10/2009 | Tweden et al. |
| 2009/0286723 A1 | 11/2009 | Levy et al. |
| 2009/0312246 A1 | 12/2009 | Baron et al. |
| 2010/0092566 A1 | 4/2010 | Alessi et al. |
| 2010/0105627 A1 | 4/2010 | Salama et al. |
| 2010/0144621 A1 | 6/2010 | Kim et al. |
| 2010/0185184 A1 | 7/2010 | Alessi et al. |
| 2010/0297209 A1 | 11/2010 | Rohloff et al. |
| 2010/0298840 A1 | 11/2010 | Schwartz |
| 2011/0076317 A1 | 3/2011 | Alessi et al. |
| 2011/0091527 A1 | 4/2011 | Moonen et al. |
| 2011/0104111 A1 | 5/2011 | Rohloff et al. |
| 2011/0152181 A1 | 6/2011 | Alsina-Fernandez et al. |
| 2011/0152182 A1 | 6/2011 | Alsina-Fernandez et al. |
| 2011/0160708 A1 | 6/2011 | Berry et al. |
| 2011/0166554 A1 | 7/2011 | Alessi et al. |
| 2011/0264077 A1 | 10/2011 | Rohloff et al. |
| 2011/0306549 A1 | 12/2011 | Tatarkiewicz et al. |
| 2012/0208755 A1 | 8/2012 | Leung |
| 2013/0030417 A1 | 1/2013 | Alessi |
| 2013/0034210 A1 | 2/2013 | Rohloff et al. |
| 2013/0052237 A1 | 2/2013 | Eliaz et al. |
| 2014/0058425 A1 | 2/2014 | Porat |
| 2014/0121741 A1 | 5/2014 | Bennett et al. |
| 2014/0257272 A1 | 9/2014 | Clark, III et al. |
| 2015/0057227 A1 | 2/2015 | Leung |
| 2015/0111818 A1 | 4/2015 | Alessi et al. |
| 2015/0133791 A1 | 5/2015 | Sato et al. |
| 2015/0231062 A1 | 8/2015 | Lautenback et al. |
| 2015/0231256 A1 | 8/2015 | Berry et al. |
| 2015/0297509 A1 | 10/2015 | Schwarz |

(56) References Cited

U.S. PATENT DOCUMENTS

| | | | |
|---|---|---|---|
| 2016/0022582 A1 | 1/2016 | Alessi et al. |
| 2016/0030337 A1 | 2/2016 | Kuzma et al. |
| 2016/0354115 A1 | 12/2016 | Smith et al. |
| 2016/0354305 A1 | 12/2016 | Alessi et al. |
| 2017/0056476 A1 | 3/2017 | Rohloff et al. |
| 2017/0079906 A1 | 3/2017 | Alessi et al. |
| 2017/0119854 A1 | 5/2017 | Alessi et al. |
| 2017/0119855 A1 | 5/2017 | Berry et al. |
| 2017/0181964 A1 | 6/2017 | Lautenbach et al. |
| 2017/0252409 A1 | 9/2017 | Leung |
| 2017/0319470 A1 | 11/2017 | Eliaz et al. |
| 2017/0319662 A1 | 11/2017 | Berry et al. |
| 2018/0185451 A1 | 7/2018 | Young et al. |

FOREIGN PATENT DOCUMENTS

| | | |
|---|---|---|
| EP | 0079405 | 5/1983 |
| EP | 0254394 | 1/1988 |
| EP | 0295411 | 12/1988 |
| EP | 0302582 A1 | 2/1989 |
| EP | 0368339 | 5/1990 |
| EP | 0373867 | 6/1990 |
| EP | 0431942 | 6/1991 |
| EP | 0486959 A1 | 5/1992 |
| EP | 0521586 A1 | 1/1993 |
| EP | 0596161 | 5/1994 |
| EP | 0379147 | 9/1994 |
| EP | 0627231 | 12/1994 |
| EP | 0729747 | 5/1997 |
| EP | 0771817 | 5/1997 |
| EP | 0841359 | 5/1998 |
| EP | 0767689 B1 | 6/1999 |
| EP | 1046399 | 10/2000 |
| EP | 1084703 | 3/2001 |
| EP | 1300129 A2 | 4/2003 |
| EP | 1300173 A2 | 4/2003 |
| EP | 1600187 | 1/2009 |
| EP | 2133073 A1 | 12/2009 |
| EP | 2020990 | 9/2010 |
| FR | 640907 | 7/1928 |
| GB | 1049104 | 11/1966 |
| GB | 1518683 | 7/1978 |
| GB | 2501400 | 10/2013 |
| JP | H02124814 A | 5/1990 |
| JP | H07196479 A | 8/1995 |
| JP | 9241153 | 9/1997 |
| JP | 11-100353 | 4/1999 |
| JP | 2006/213727 A | 8/2006 |
| NL | 9100160 | 8/1992 |
| NZ | 592113 | 8/2012 |
| TW | 200634060 | 10/2006 |
| WO | WO1989003678 A1 | 5/1989 |
| WO | WO1990013285 A1 | 11/1990 |
| WO | WO1990013361 A1 | 11/1990 |
| WO | WO1990013780 A1 | 11/1990 |
| WO | WO 91/07160 | 5/1991 |
| WO | WO1992019241 A1 | 11/1992 |
| WO | WO 93/06819 | 4/1993 |
| WO | WO 93/06821 | 4/1993 |
| WO | WO 93/008832 | 5/1993 |
| WO | WO 93/09763 | 5/1993 |
| WO | WO 93/23083 | 11/1993 |
| WO | WO 94/09743 | 5/1994 |
| WO | WO1994010982 A1 | 5/1994 |
| WO | WO 94/21262 | 9/1994 |
| WO | WO 95/01167 | 1/1995 |
| WO | WO 95/09006 | 4/1995 |
| WO | WO 95/09007 | 4/1995 |
| WO | WO1995013799 A1 | 5/1995 |
| WO | WO 95/34285 | 12/1995 |
| WO | WO 1996/01134 A1 | 1/1996 |
| WO | WO 96001134 | 1/1996 |
| WO | WO 96/003116 | 2/1996 |
| WO | WO1996036317 A1 | 11/1996 |
| WO | WO 96/40049 | 12/1996 |
| WO | WO 96/40139 | 12/1996 |
| WO | WO 96/40355 | 12/1996 |
| WO | WO1996040049 A1 | 12/1996 |
| WO | WO 97/15289 | 5/1997 |
| WO | WO 97/15296 | 5/1997 |
| WO | WO 97/28181 | 8/1997 |
| WO | WO1997031943 A1 | 9/1997 |
| WO | WO1997044039 A1 | 11/1997 |
| WO | WO 97/46204 | 12/1997 |
| WO | WO 97/47339 | 12/1997 |
| WO | WO 98/00152 | 1/1998 |
| WO | WO 98/00157 | 1/1998 |
| WO | WO 98/00158 | 1/1998 |
| WO | WO 98/02169 | 1/1998 |
| WO | WO1997041837 A3 | 2/1998 |
| WO | WO1998007412 A1 | 2/1998 |
| WO | WO 98/16250 | 4/1998 |
| WO | WO 98/17315 | 4/1998 |
| WO | WO 98/20930 | 5/1998 |
| WO | WO 98/27960 | 7/1998 |
| WO | WO 98/027962 | 7/1998 |
| WO | WO 98/27963 | 7/1998 |
| WO | WO 98/030231 | 7/1998 |
| WO | WO 98/32463 | 7/1998 |
| WO | WO1998030231 A1 | 7/1998 |
| WO | WO 98/42317 | 10/1998 |
| WO | WO 98/47487 | 10/1998 |
| WO | WO 98/51282 | 11/1998 |
| WO | WO 99/03453 | 1/1999 |
| WO | WO 99/04767 | 2/1999 |
| WO | WO 99/004768 | 2/1999 |
| WO | WO 1999/04768 A2 | 2/1999 |
| WO | WO1999012549 A2 | 3/1999 |
| WO | WO 99/16419 | 4/1999 |
| WO | WO 99/025728 | 5/1999 |
| WO | WO 99/29306 | 6/1999 |
| WO | WO 99/033446 | 7/1999 |
| WO | WO 99/33449 | 7/1999 |
| WO | WO 99/040788 | 8/1999 |
| WO | WO 1999/44659 A1 | 9/1999 |
| WO | WO 99/062501 | 12/1999 |
| WO | WO 99/064061 | 12/1999 |
| WO | WO 00/013663 | 3/2000 |
| WO | WO 00/029206 | 5/2000 |
| WO | WO 00/038652 | 7/2000 |
| WO | WO 00/039280 | 7/2000 |
| WO | WO 00/040273 | 7/2000 |
| WO | WO 00/041548 | 7/2000 |
| WO | WO 00/045790 | 8/2000 |
| WO | WO 00/054745 | 9/2000 |
| WO | WO2000059476 A1 | 10/2000 |
| WO | WO 00/066138 | 11/2000 |
| WO | WO 00/067728 | 11/2000 |
| WO | WO2000066087 A2 | 11/2000 |
| WO | WO2001019345 A1 | 3/2001 |
| WO | WO2001028525 A2 | 4/2001 |
| WO | WO 01/043528 | 6/2001 |
| WO | WO 01/051041 | 7/2001 |
| WO | WO 01/78683 | 10/2001 |
| WO | WO 02/028366 | 4/2002 |
| WO | WO 02/036072 | 5/2002 |
| WO | WO 02/043800 | 6/2002 |
| WO | WO 02/045752 | 6/2002 |
| WO | WO 02/47716 | 6/2002 |
| WO | WO 02/067895 | 9/2002 |
| WO | WO 02/069983 | 9/2002 |
| WO | WO 02/76344 | 10/2002 |
| WO | WO 02/085428 | 10/2002 |
| WO | WO 03/007981 | 1/2003 |
| WO | WO 2003/000230 A1 | 1/2003 |
| WO | WO 03/011892 | 2/2003 |
| WO | WO 03/024357 | 3/2003 |
| WO | WO 2003/024503 A2 | 3/2003 |
| WO | WO2003020245 A1 | 3/2003 |
| WO | WO 03/030923 | 4/2003 |
| WO | WO 03/041684 | 5/2003 |
| WO | WO 03/041757 | 5/2003 |
| WO | WO 03/053400 | 7/2003 |
| WO | WO2003066585 A2 | 8/2003 |

(56) References Cited

FOREIGN PATENT DOCUMENTS

| WO | WO 03/072113 | 9/2003 |
|---|---|---|
| WO | WO 03/072133 | 9/2003 |
| WO | WO 2004/002565 A1 | 1/2004 |
| WO | WO2004034975 A2 | 4/2004 |
| WO | WO2004035754 A2 | 4/2004 |
| WO | WO2004035762 A2 | 4/2004 |
| WO | WO2004036186 A2 | 4/2004 |
| WO | WO 04/052336 | 6/2004 |
| WO | WO 04/056338 | 7/2004 |
| WO | WO 04/089335 | 10/2004 |
| WO | WO2004103342 A2 | 12/2004 |
| WO | WO 05/048930 | 6/2005 |
| WO | WO 2005/048952 A2 | 6/2005 |
| WO | WO 05/102293 | 11/2005 |
| WO | WO2005102293 A1 | 11/2005 |
| WO | WO2005110425 | 11/2005 |
| WO | WO 06/017772 | 2/2006 |
| WO | WO 2006/023526 A2 | 3/2006 |
| WO | WO 06/081279 | 8/2006 |
| WO | WO 06/083761 | 8/2006 |
| WO | WO 2006/084139 A2 | 8/2006 |
| WO | WO 2006/086727 | 8/2006 |
| WO | WO 2006/086727 A2 | 8/2006 |
| WO | WO 06/101815 | 9/2006 |
| WO | WO 06/111169 | 10/2006 |
| WO | WO 2006/131730 | 12/2006 |
| WO | WO 07/024700 | 3/2007 |
| WO | WO 07/056681 | 5/2007 |
| WO | WO 07/075534 | 7/2007 |
| WO | WO 07/084460 | 7/2007 |
| WO | WO 07/133778 | 11/2007 |
| WO | WO 07/140416 | 12/2007 |
| WO | WO 08/021133 | 2/2008 |
| WO | WO2008041245 A2 | 4/2008 |
| WO | WO 08/061355 | 5/2008 |
| WO | WO 08/133908 | 11/2008 |
| WO | WO 08/134425 | 11/2008 |
| WO | WO 09/109927 | 9/2009 |
| WO | WO2009143285 A2 | 11/2009 |
| WO | WO 2013/004983 A1 | 1/2013 |

OTHER PUBLICATIONS

Costantino et al., "Protein Spray Freeze Drying. 2. Effect of Formulation Variables on particle Size and Stability," J. Pharm. Sci. 91:388-395 (2002).

Henry et al., "Comparing ITCA 650, continuous subcutaneous delivery of exenatide via DUROS® device, vs. twice daily exenatide injections in metformin-treated type 2 diabetes," oral presentation at the 46th Annual Meeting of the European Association for the Study of Diabetes in Stockholm, Sweden , 21 pages (Sep. 20-24, 2010).

Huggins et al., "Synergistic antiviral effects of ribavirin and the C-nucleoside analogs tiazofurin and selenazofurin against togaviruses, bunyaviruses, and arenaviruses," Antimicrobial Agents & Chemotherapy, 26(4):476-480 (1984).

Ishiwata et al., "Clinical effects of the recombinant feline interferon-omega on experimental parvovirus infection in beagle dogs," J. Vet. Med. Sci. 60(8):911-917 (1998).

Johnson et al., "How interferons fight disease," Sci. Am. 270(5):68-75 (May 1994).

Lublin et al., "Defining the clinical course of multiple sclerosis: results of an international survey," Neurology. 46:907-911 (1996).

Madsbad, "Exenatide and liraglutide: different approaches to develop GLP-1 receptor agonists (incretin mimetics)—preclinical and clinical results," Best Practice & Research Clinical Endocrinology & Metabolism 23:463-77 (2009).

Nielsen, "Incretin mimetics and DPP-IV inhibitors for the treatment of type 2 diabetes," Drug Discovery Today 10(10):703-710 (May 15, 2005).

Palmeri et al., "5-Fluorouracil and recombinant α-interferon-2a in the treatment of advanced colorectal carcinoma: a dose optimization study," J. Chemotherapy 2(5):327-330 (Oct. 1990).

Patti et al., "Natural interferon-b treatment of relapsing-remitting and secondary-progressive multiple sclerosis patients: two-year study," Acta. Neurol. Scand. 100:283-289 (1999).

Paty et al., "Interferon beta-1 b is effective in relapsing-remitting multiple sclerosis," Neurology 43:662-667 (1993).

PCT International Search Report for PCT/US2009/000916, 4 pages (dated Aug. 12, 2009).

"Intarcia Therapeutics Announces Final Results from a Phase 2 Study of Injectable Omega Interferon plus Ribavirin for the Treatment of Hepatits C Genotype-1 ," NLV Partners Press Coverage Portofolio News (Apr. 12, 2007) (Press Release).

Quianzon et al., "Lixisenatide-Once-daily Glucagon-like Peptide-1 Diabetes," US Endocrinology 7(2):104-109 (2011).

Ratner et al., "Dose-dependent effects of the one-daily GLP-1 receptor agonist lixisenatide in patients with Type 2 diabetes inadequately controlled with metfmmin: a randomized, double-blind, placebo-controlled trial," Diabetic Medicine 27(9):1024-1032 (Sep. 2010).

Roberts et al., "The Evolution of the Type I Interferons1," J. Interferon Cytokine Res. 18(10):805-816 (Oct. 1998).

Rohloff et al., "DUROS Technology Delivers Peptides and Proteins at Consistent Rate Continuously for 3 to 12 Months," J. Diabetes Sci. & Tech., 2(3):461-467 (May 1, 2008).

"Sequence Listings for International Patent Application Publication No. W02009109927, WIPO Patentscope", http://patentscope.wipo.int/search/docservicepdf_pct!id00000008776887, 1 page (last visited Nov. 14, 2012).

Shire et al., "Challenges in the Development of High Protein Concentration Formulations," J. Pharm. Sci. 93:1390-1402 (2004).

Smith, "Peripheral Neuro-hormones as a Strategy to Treat Obesity," oral presentation at the 2007 Cardiometabolic Health Congress in Boston, MA, pp. 1-35 (Sep. 26-29, 2007).

Written Opinion for International Patent Application No. PCT/US2009/005629 (corresponding to U.S. Appl. No. 12/587,946), 5 pages (dated Apr. 15, 2011).

Zhang et al., "Efficacy observations of different dosages of interferon to treat 150 Hepatitis B carriers," Current Physician 2(12):45-46 (1997).

"Abstracts 2007," Diabetologia Clinical & Experimental Diabetes & Metabolism, Springer, Berlin, Germany, vol. 50 S243 (Aug. 21, 2007) (paragraph [0586]) (XP002538652).

Jetschmann et al., "Open-label rising-dose study of omega interferon in IFN-naive patients with chronic hepatitis C," Gastroenterology 122:A278-A347 (Apr. 1, 2002) (Abstract M1454).

Bray, "Gut Signals and Energy Balance: Ghrelin, Peptide YY, Leptin, and Amylin," (Dec. 19, 2007) (slides and transcript for presentation at Medscape CME).

"Implantable infusion pumps: technology poised for takeoff," BBI Newsletter 17(12):209-211 (Dec. 1994).

Adamson et al., "Phase I trial and pharmacokinetic study of all-trans-retinoic acid administered on an intermittent schedule in combination with interferon-alpha2a in pediatric patients with refractory cancer," J. Clin. Oncol. 15(11):3330-3337 (Nov. 1997).

Adolf et al., "Monoclonal antibodies and enzyme immunoassays specific for human interferon (IFN) ω1: evidence that IFN-ω1 is a component of human leukocyte IFN," Virology 175(2):410-471 (Apr. 1990).

Adolf et al., "Antigenic structure of human interferon ω1 (Interferon αII1): comparison with other human interferons," J. Gen. Virol. 68(6):1669-1676 (Jun. 1987).

Adolf et al., "Purification and characterization of natural human interferon ω1," J. Bio. Chem. 265(16):9290-9295 (Jun. 1990).

Adolf et al., "Human interferon ω1: isolation of the gene, expression in Chinese hamster ovary cells and characterization of the recombinant protein," Biochim. Biophys. Acta 108(9):167-174 (Jun. 1991).

Andrx Pharmaceuticals, LLC, ANDA for Concerta® Extended-Release Tablets, 6 pages (correspondence dated Sep. 6, 2005).

ASTM International, Annual Book of ASTM Standards, 8.02:208-211, 584-587 (1984).

Ansel et al., "Dosage Form Design: Pharmaceutical and Formulation Considerations," Pharmaceutical Dosage Forms and Drug Delivery Systems, Ch. 3 at 87-92 (7th ed. Lippincott Williams & Wilkins 1999).

(56) References Cited

OTHER PUBLICATIONS

Ansel et al., "Modified-Release Dosage Forms and Drug Delivery Systems," Pharmaceutical Dosage Forms and Drug Delivery Systems, Ch. 8 at 229-243 (7th ed. Lippincott Williams & Wilkins 1999).
Aulitzky, "Successful Treatment of Metastatic Renal Cell Carcinoma With a Biologically Active Dose of Recombinant Interferon-Gama," Journal of Clinical Oncology 7(12):1875-1884 (1989).
Hauck, "Engineer's Guide to Plastics," Materials Engineering 5(72):38-45 (Jul. 17, 1972).
Bailon et al., "Rational Design of a Potent, Long-lasting Form of Interferon: A 40 kDa Branched Polyethylene Glycol-conjugated Interferon Alpha-2a for the Treatment of Hepatitis C," Bioconjugate Chemistry 12(2):195-202 (2001).
Bakan et al., "Physicochemical Characterization of a Synthetic Lipid Emulsion for Hepatocyte-Selective Delivery of Lipophilic Compounds: Application to Polyiodinated triglycerides as Contrast Agents for Computed Tomography," J. Pharm. Sci., 85(9):908-914 (1996).
Bakhtiar et al, "Taking Delivery," Soap Perfumery & Cosmetics 76(3):59-65 (2003) (liposomes in cosmetic delivery systems).
Balkwill,F., "Interferons," Lancet 1(8646):1060-1063 (May 1989).
Bauer et al., "Non-aqueous emulsions as vehicles for capsule fillings," Drug Dev. & Industrial Pharmacy 10(5):699-712 (1984).
Bekkering et al., "Estimation of early hepatitis C viral clearance in patients receiving daily interferon and ribavirin therapy using a mathematical model," Hepatology 33(2):419-423 (Feb. 2001).
Bell et al., "Hamster preproglucagon contains the sequence of glucagon and two related peptides," Nature 302:716-718 (1983).
Bell et al, "Impact of moisture on thermally induced denaturation and decomposition of lyophilized bovine somatotropin," Drug Delivery Research & Dev. Biopolymers, (35):201-209 (1995).
Bertoncello et al., "Haematopoietic radioprotection by Cremophor EL: a polyethoxylated castor oil," Int. J. Radiat. Biol. 67(1):57-64 (1995).
Bohlinder et al., "Use and characteristics of a novel lipid particle-forming matrix as a drug-carrier system," Euro. J. Pharm. Sci. 2(4):271-279 (1994).
Bolinger et al., "Recombinant interferon γ for treatment of chronic granulomatous disease and other disorders," Clin. Pharm. 11(10):834-850 (Oct. 1992).
Bonkovsky et al., "Outcomes research in chronic viral hepatitis C: effects of interferon therapy," Can. J. Gastroenterol. 14(Supp. B):21B-29B (Jul.-Aug. 2000).
Borden et al., "Second-generation interferons for cancer: clinical targets," Semin. Cancer Biol. 10(2):125-144 (Apr. 2000).
Boué et al., "Antiviral and antiluteolytic activity of recombinant bovine IFN-ω1 obtained from Pichia pastoris," J. Interferon & Cytokine Res. 20:677-683 (2000).
Buckwold et. al. "Antiviral activity of CHO-SS cell-derived human omega interferon and other human interferons against HCV RNA replicons and related viruses," Antiviral Res. 73(2):118-25 (Feb. 2007) (Epub Sep. 11, 2006).
Cantor, "Theory of lipid monolayers comprised of mixtures of flexible and stiff amphiphiles in anthermal solvents: fluid phase coexistence," J. Chem. Physics 104(20):8082-8095 (1996).
CAS No. 56-81-5 (Nov. 16, 1984).
Chang et al., "Biodegradeable polyester implants and suspension injection for sustained release of a cognitive enhancer," Pharm. Tech. 20(1):80-84 (1996).
Chapman et al., "Physical Studies of Phospholipids. VI. Thermotropic and Lyotropic Mesomorphism of Some 1,2-Diacylphosphatidylcholines (lecithins)," Chem. & Physics of Lipids 1(5):445-475 (1967).
Chaumeil, "Micronization: a method of improving the bioavailability of poorly soluble drugs," Methods & Findings in Experimental & Clinical Pharmacology 20(3):211-215 (1998).
Clark et al., "The diabetic Zucker fatty rat," Proc. Soc. Exp. Biol. 173(1):68-75 (1983).
Condino-Neto, "Interferon-γ improves splicing efficiency of CYBB gene transcripts in an interferon responsive variant of chronic granulomatous disease due to a splice site consensus region mutation," Blood 95(11):3548-3554 (Jun. 2000).
Darney, "Subdermal progestin implant contraception," Current Opinion in Obstetrics & Gynecology 3:470-476 (1991).
Das, S. et al., "Reviewing Antisense Oligonucleotide Therapy: Part 2, Delivery Issues," BioPharm, 2(11):44-51 (1999).
Dash, A. K. et al., "Therapeutic applications of implantable drug delivery systems," Journal of Pharmacological and Toxicological Methods, 40(1):1-12 (1998).
Davis et al., "Durability of viral response to interferon alone or in combination with oral ribavirin in patients with chronic hepatitis C," Prog. Abstr. 50th Annu. Mtg. Postgrad. Courses Am. Assn. Study Liver Dis., Dallas, TX (Nov. 5-9, 1999)(Abstract 570 ).
Deacon, C. F. et al., "GLP-1-(9-36) amide reduces blood glucose in anesthetized pigs by a mechanism that does not involve insulin secretion," Am. J. Physiol. Endocrinol. Metab., 282:E873-E879 (2002).
Desai et al., "Protein structure in the lyophilized state: a hydrogen isotope exchange/NMR study with bovine pancreatic trypsin inhibitor," J. Am. Chem. Soc. 116(21):9420-9422 (1994).
Di Marco et al., "Combined treatment of relapse of chronic hepatitis C with high-dose α-2B interferon plus ribavirin for 6 or 12 months," Prog. Abstr. 50th Annu. Mtg. Postgrad. Courses Am. Assn. Study Liver Dis., Dallas, TX (Nov. 5-9, 1999)(Abstract 569).
Dorr et al., "Phase I-II trial of interferon-alpha 2b by continuous subcutaneous infusion over 28 days," J. Interferon Res. 8:717-725 (1988).
Uhlig et al., "The electro-smotic acutation of implantable insulin micropumps," J. Biomed. Materials Res. 17:931-943 (1983).
Efendic, S. et al., et al., "Overview of incretin hormones," Horm. Metab. Res., 36(11-12):742-746 (2004).
Eissele, R. et al., "Rat gastric somatostatin and gastrin release: interactions of exendin-4 and truncated glucagon-like peptide-1 (GLP-1) amide," Life Sci., 55(8):629-634 (1994).
Elias et al., "Infusional Interleukin-2 and 5-fluorouracil with subcutaneous interferon-α for the treatment of patients with advanced renal cell carcinoma: a southwest oncology group Phase II study," Cancer 89(3):597-603 (Aug. 2000).
Eng, J. et al., "Isolation and characterization of exendin-4, an exendin-3 analogue, from Heloderma suspectum venom. Further evidence for an exendin receptor on dispersed acini from guinea pig pancreas," J. Biol. Chem., 267(11):7402-7405 (1992).
Eng, J. et al., "Purification and structure of exendin-3, a new pancreatic secretagogue isolated from Heloderma horridum venom," J. Biol. Chem., 265(33):20259-20262 (1990).
Eppstein et al., "Biological activity of liposome-encapsulated murine interferon γ is mediated by a cell membrane receptor," PNAS USA 82:3688-3692 (1985).
Eros et al., "Multiple phase emulsions as controlled drug delivery therapeutic systems," Proc.-Conf. Colloid Chem. 193-196 (1993).
Fang et al., "The impact of baseline liver histology on virologic response to interferon α-2b±ρ ribavirin therapy in patients with chronic hepatitis C," Prog. Abstr. 50th Annu. Mtg. Postgrad. Courses Am. Assn. Study Liver Dis., Dallas, TX (Nov. 5-9, 1999)(Abstract 572).
Felker et al., "The Rate of Transfer of Unesterified Cholesterol from Rat Erythrocytes to Emulsions Modeling Nascent Triglyceride-Rich Lipoproteins and Chylomicrons Depends on the Degree of Fluidity of the Surface," J. Nutritional Biochem. 4(1):630-634 (1993).
Ferenci et al, "Combination of interferon (IFN) induction therapy and ribavirin in chronic hepatitis C," Prog. Abstr. Dig. Dis. Week 2000, San Diego, CA (May 21-24, 2000) (Abstract 977).
Fontaine et al., "Recovery from chronic hepatitis C in long-term responders to ribarivin plus interferon α," Lancet 356(9223):41 (Jul. 2000).
Franchetti et al., "Furanfurin and Thiophenfurin: Two Novel TiazofurinAnalogues. Synthesis, Structure, Antitumor Activity, and Interactions with Inosine Monophosphate Dehydrogenase," J. Medicinal Chem. 38(19):3829-3837 (1995).
Fujii et al., "Effect of phosphatidylcholine on Skin Permeation of Indomethacin from gel prepared with Liquid Paraffin and Hydrogenated Phospholipid," Int'l J. Pharmaceutics 222(1):57-64 (2001).

(56) References Cited

OTHER PUBLICATIONS

Fujii et al., "Enhancement of skin permeation of miconazole by phospholipid and dodecyl 2-(N, N-dimethylamino) propionate (DDAIP)," Int'l J. Pharmaceutics 234(1-2):121-128 (2002).
Luft et al., "Electro-osmotic valve for the controlled administration of drugs," Med. & Biological Engineering & Computing 45-50 (Jan. 1978) (non-English with English abstract).
Gan to Kagaku Ryoho, "Phase II study of recombinant leukocyte A interferon (Ro22-8181) in malignant brain tumors," Cancer & Chemotherapy 12(4):913-920 (Apr. 1985) (non-English with English abtract).
Gappa et al., "Juvenile laryngeal papillomatosis—a case report," Pneumologie 45(11):936-938 (Nov. 1991) (XP009079028) (non-English with English abstract).
Gause et al., "Phase I study of subcutaneously administered interleukin-2 in combination with interferon alfa-2a in patients with advanced cancer," J. Clin. Oncol. 14(8):2234-2241 (Aug. 1996).
Ghiglione, M., et al., "How glucagon-like is glucagon-like peptide-1?" Diabetologia 27:599-600 (1984).
Glue et al., "A dose-ranging study of Peg-intron and ribavirin in chronic hepatitis C—safety, efficacy, and virological rationale," Prog. Abstr. 50th Annu. Mtg. Postgrad. Courses Am. Assn. Study Liver Dis., Dallas, TX(Nov. 5-9, 1999)(Abstract 571).
Goke, R. et al., "Exendin-4 is a high potency agonist and truncated exendin-(9-39)-amide an antagonist at the glucagon-like peptide 1-(7-36)-amide receptor of insulin-secreting beta-cells," J. Biol. Chem., 268(26):19650-19655 (1993).
Gonzales et al., "Randomized controlled trial including an initial 4-week 'induction' period during one year of high-dose interferon α-2B treatment for chronic hepatitis C," Prog. Abstr. Dig. Dis. Week 2000, San Diego, CA (May 21-24, 2000) (Abstract 975).
Gosland et al., "A phase I trial of 5-day continuous infusion cisplatin and Interferon alpha," Cancer Chemother. Pharmacol. 37(1-2):39-46 (1995).
Grant et al., "Combination therapy with interferon-α plus N-acetyl cystein for chronic hepatitis C: a placebo controlled double-blind multicentre study," J. Med. Virol. 61(4):439-442 (Aug. 2000).
Gutniak, M. et al., "Antidiabetogenic effect of glucagon-like peptide-1 (7-36)amide in normal subjects and patients with diabetes mellitus," N. Engl. J. Med., 326(20):1316-1322 (1992).
Hageman, "The Role of Moisture in Protein Stability," Drug Dev. & Ind. Pharm. 14(14):2047-2070 (1988).
Heathcote et al., "Peginterferon alfa-2a in Patients With Chronic Hepatitis C and Cirrhosis," New England J. Med. 343(23):1673-1680 (2000).
Heim et al., "Intracellular signaling and antiviral effects of interferons," Dig. Liver Dis. 32(3):257-263 (Apr. 2000).
Heinrich, G. et al., "Pre-proglucagon messenger ribonucleic acid: nucleotide and encoded amino acid sequences of the rat pancreatic complementary deoxyribonucleic acid," Endocrinol., 115:2176-2181 (1984).
Hellstrand et al., "Histamine and cytokine therapy," Acta Oncol. 37(4):347-353 (1998).
Hellstrand et al., "Histamine and the response to IFN-α in chronic hepatitis C," Interferon Cytokine Res. 18(1):21-22 (Jan. 1998).
Hellstrand et al., "Histamine in immunotherapy of advanced melanoma: a pilot study," Cancer Immunol Immunother. 39(6):416-419 (Dec. 1994).
Hisatomi et al., "Toxicity of polyoxyethylene hydrogenated castor oil 60 (HCO-60) in experimental animals," J. Toxicol. Sci., 18(3):1-9 (1993).
Hodoshima, N. et al., "Lipid nanoparticles for delivering antitumor drugs," International Journal of Pharmaceutics, 146(1):81-92 (1997).
Hoffmann-La Roche Inc., Pegasys® (peginterferon alfa-2a), 15 pages (2002).
Horton et al., "Antitumor effects of interferon-omega: in vivo therapy of human tumor xenografts in nude mice" Cancer Res 59(16):4064-4068 (Aug. 1999).
Hubel et al., "A phase I/II study of idarubicin, dexamethasone and interferon-alpha (1-Dexa) in patients with relapsed or refractory multiple myeloma" Leukemia 11 Suppl 5:S47-S51 (Dec. 1997).
Iacobelli et al., "A phase I study of recombinant interferon-alpha administered as a seven-day continuous venous infusion at circadian-rhythm modulated rate in patients with cancer," Am. J. Clin. Oncol. 18(1):27-31 (1995).
IFNB Multiple Sclerosis Study Group, "Interferonβ-1b is effective in relapsing-remitting multiple sclerosis," Neurology 43(4):655-667 (Apr. 1993).
Intermune® Inc., Infergen® (Interferon alfacon-1), 5 pages (2002).
"Introduction to Antibodies", http://www.chemicon.com/resource/ANT101/a1.asp, 8 pages (retrieved May 2, 2007).
Isaacs et al., "Virus interference. I. The interferon," Pro. R. Soc. Lond. B. Biol. Sci. 147:258-267 (1957).
Jain et al., "Controlled delivery of drugs from a novel injectable in situ formed biodegradable PLGA microsphere system," J. Microencapsulation 17(3):343-362 (2000).
Jordan et al., "Guidelines for Antiemetic Treatment of Chemotherapy-Induced Nausea and Vomiting: Past, Present and Future Recommendations," The Oncologist 12(9):1143-1150 (2007).
Kabalnov et al., "Macroemulsion type and stability of alkane-water-phospholipid systems," Abstracts of Papers, Part 1, 210th ACS National Meeting, 0-8412-3222-9, American Chemical Society, Chicago, IL (Aug. 20-24, 1995) (Abstract only).
Kabalnov et al., "Phospholipids as Emulsion Stabilizers.2. Phase Behavior Versus Emulsion Stability," Journal of Colloid and Interface Science 184(1):227-235 (1996).
Khalili et al., "Interferon and ribavirin versus interferon and amantadine in interferon nonresponders with chronic hepatitis C," Am. J. Gastroenterol. 95(5):1284-1289 (May 2000).
Kildsig et al., "Theoretical Justification of Reciprocal Rate Plots in Studies of Water Vapor Transmission through Films," J. Pharma. Sci. 29(11):1634-01637 (Nov. 17, 1970).
Kirkwood et al., "Interferon alfa-2b adjuvant therapy of high-risk resected cutaneous melanoma: The Eastern Cooperative Oncology Group Trial EST 1684," J. Clin. Oncol. 14(1):7-17 (1996).
Kita et al., "Characterization of a polyethylene glycol conjugate of recombinant human interferon-γ," Drug Des. Deliv. 6(3):157-0167 (Sep. 1990).
Knepp et al, "Identification of antioxidants for prevention of peroxide-mediated oxidation of recombinant human ciliary neurotrophic factor and recombinant human nerve growth factor," J. Pharm. Sci. Tech. 50(3):163-171 (1996).
Knepp et al., "Stability of nonaqueous suspension formulations of plasma derived factor IX and recombinant human alpha interferon at elevated temperatures," Pharma. Res. 15(7):1090-1095 (1998).
Knobler et al., "Systemic α-interferon therapy of multiple sclerosis," Neurology 34(10):1273-1279 (Oct. 1984).
Kovacevic et al., "Treatment of chronic viral hepatitis B in secondary membranoproliferative glomerulonephritis using recombinant α-2 interferon," Maksic Dj Vojnosanit. Pregl. 57(2):235-240 (Mar.-Apr. 2000) (non-English with English abstract).
Kracke et al., "Mx proteins in blood leukocytes for monitoring interferon β-1b therapy in patients with MS," Neurology 54(1):193-199 (Jan. 2000).
Kronenberger et al., "Influence of interferon-α on CD82-expression in HCV-positive patients," Prog. Abstr. Dig. Dis. Week 2000, San Diego, CA (May 21-24, 2000) (Abstract 976).
Krown et al., "Interferons and interferon inducers in cancer treatment," Semin. Oncol. 13(2):207-217 (1986).
Kubes et al., "Cross-species antiviral and antiproliferative activity of human interferon-ω," J. Interferon Res. 14:57-59 (1994).
Kunzi et al., "Role of interferon-stimulated gene ISG-15 in the interferon-ω-mediated inhibition of human immunodeficiency virus replication," J. Interferon Cytokine Res. 16(11):919-927 (Nov. 1996).
Larsson, "Stability of emulsions formed by polar lipids," Progress in the Chemistry of Fats and Other Lipids 16:163-0169 (1978).
Lee et al., "Dynamics of hepatitis C virus quasispecies turnover during interferon-A treatment," Prog. Abstr. Dig. Dis. Week 2000, San Diego, CA (May 21-24, 2000) (Abstract 974).

(56) References Cited

OTHER PUBLICATIONS

Lee, "Therapy of hepatits C: interferon alfa-2A trials," Hepatology 26: 89S-95S (Sep. 1997) (XP000981288).
Lopez, L. C. et al., "Mammalian pancreatic preproglucagon contains three glucagon-related peptides," Proc. Natl. Acad. Sci. USA, 80(18):5485-5489 (1983).
Lukaszewski et al., "Pegylated α interferon is an effective treatment for virulent Venezuelan equine encephalitis virus and has profound effects on host immune response to infection," J. Virol. 74(11):5006-5015 (Jun. 2000).
Lund, P. K. et al., "Pancreatic preproglucagon cDNA contains two glucagon-related coding sequences arranged in tandem," Proc. Natl. Acad. Sci. USA, 79(2):345-349 (1982).
Lundberg, "A submicron lipid emulsion coated with amphipathic polyethylene glycol for parenteral administration of paclitaxel (Taxol)," J. Pharm. & Pharmacol. 49(1):16-21 (1997).
Magnuson et al. "Enhanced recovery of a secreted mammalian protein from suspension culture of genetically modified tobacco cells," Protein Expression & Purification 7:220-228 (1996).
Malley et al., "Chronic Toxicity and Oncogenicity of N-Methylpyrrolidone (Nmp) in Rats and Mice by Dietary Administration," Drug Chem Toxicol. 24(4):315-38 (Nov. 2001).
Manning et al, "Stability of protein pharmaceuticals," Pharm. Res. 6(11):903-918 (1989).
Marincola et al., "Combination therapy with interferon alfa-2a and interleukin-2 for the treatment of metastatic cancer," J. Clinical Oncol. 13(5):1110-1122 (1995) (XP009078965).
Massey, "Interaction of vitamin E with saturated phospholipid bilayers," Biochem. & Biophys. Res. Comms. 106(3):842-847 (1982).
McHutchison et al., "Interferon α-2b alone or in combination with ribavirin as initial treatment for chronic hepatitis C," N. Engl. J. Med. 339(21):1485-1492 (Nov. 1998).
McHutchison, et al., "Open-label phase 1B study of hepatitis C viral dynamics with omega interferon treatment," Hepatology 34(4):A333 (Oct. 1, 2001) (XP004716177) (Abstract Only).
Meier, J. J. et al., "The glucagon-like peptide-1 metabolite GLP-1-(9-36) amide reduces postprandial glycemia independently of gastric emptying and insulin secretion in humans," Am. J. Physiol. Endocrinol. Metab., 290(6):E1118-E1123 (2006).
Merad et al., "Generation of monocyte-derived dendritic cells from patients with renal cell cancer: modulation of their functional properties after therapy with biological response modifiers (IFN-α plus IL-2 and IL-12)," J. Immunother. 23(3):369-378 (May-Jun. 2000).
Milella et al., "Neutralizing antibodies to recombinant α-interferon and response to therapy in chronic hepatitis C infection," Liver 13(3):146-150 (Jun. 1993).
Mohler, "Primer on electrodeposited coatings," Materials Engineering 5:38-45 (1972).
Mojsov, S., "Structural requirements for biological activity of glucagon-like peptide-I," Int. J. Peptide Protein Research, 40:333-343 (1992).
Morgan, "Structure and Moisture Permeability of Film-Forming Poloyers," Ind. Eng. Chem. 45(10):2296-2306 (1953).
Motzer et al., "Phase I trial of 40-kd branched pegylated interferon alfa-2a for patients with advanced renal cell carcinoma," J. Clinical Oncol. 19(5):1312-1319 (2001).
Nauck, M. A. et al., "Normalization of fasting glycaemia by intravenous GLP-1 ([7-36 amide] or [7-37]) in type 2 diabetic patients," Diabet. Med., 15(11):937-945(1998).
Neumann et al., "Hepatitis C Viral Dynamics In Vivo and the Antiviral Efficacy of Interferon-alpha Therapy," Science 282:103-107 (Dec. 1998).
Nieforth et al., "Use of an indirect pharmacodynamic stimulation model of MX protein induction to compare in vivo activity of interferon-α-2a and a polyethylene glycol-modified derivative in healthy subjects," Clin. Pharmacol. Ther. 59(6):636-646 (Jun. 1996).

Norden et al., "Physicochemical characterization of a drug-containing phospholipid-stabilized o / w emulsion for intravenous administration," Eur. J. Pharm. Sci. 13(4):393-401 (2001).
Olaso et al., "Early prediction of lack of response to treatment with interferon and interferon plus ribavirin using biochemical and virological criteria in patients with chronic hepatitis C," Esp. Quimioter. 12(3):220-228 (Sep. 1999) (non-English with English abstract).
Ortiz, A. et al., "A differential scanning calorimetry study of the interaction of α-tocopherol with mixtures of phospholipids," Biochim et Biophys Acta 898(2):214-222 (1987).
Panitch, "Interferons in multiple sclerosis," Drugs 44(6):946-962 (Dec. 1992).
Patzelt, C. et al., "Identification and processing of proglucagon in pancreatic islets," Nature, 282:260-266 (1979).
Peterson, R. G. et al., "Zucker Diabetic Fatty Rat as a Model for Non-insulin-dependent Diabetes Mellitus," ILAR Journal, 32(3):16-19 (1990).
Peterson, R. G. et al., "Neuropathic complications in the Zucker diabetic fatty rat (ZDF/Drt-fa)," Frontiers in diabetes research. Lessons from Animal Diabetes III, Shafrir, E. (ed.), pp. 456-458, Smith-Gordon, London (1990).
Pimstone et al., "High dose (780 MIU/52 weeks) interferon monotherapy is highly effective treatment for hepatitis C," Prog. Abstr. Dig. Dis. Week 2000, San Diego, CA (May 21-24, 2000) (Abstract 973).
Plauth et al, "Open-label phase II study of omega interferon in previously untreated HCV infected patients," Hepatology 34(4):A331 (Oct. 1, 2001) (XP004716169) (Abstract Only).
Plauth et al, "Open-label study of omega interferon in previously untreated HCV-infected patients," J. Hepatology 36(Supp. 1):125 (Apr. 2002) (XP002511882) (Abstract Only).
Pohl, M. et al., "Molecular cloning of the helodermin and exendin-4 cDNAs in the lizard. Relationship to vasoactive intestinal polypeptide/ pituitary adenylate cyclase activating polypeptide and glucagon-like peptide 1 and evidence against the existence of mammalian homologues," J. Biol. Chem., 273(16):9778-9784 (1998).
Poynard et al., "Is an 'a la carte' combined interferon α 2b plus ribavirin possible for the first line treatment in patients with chronic hepatitis C," Hepatology 31(1):211-218 (Jan. 2000).
Poynard et al., "Randomized trial of interferon α 2b plus ribavirin for 48 weeks or for 24 weeks versus interferon α 2b plus placebo for 48 weeks for the treatment of chronic infection with hepatitis C virus," Lancet 352(9138):1426-1432 (Oct. 1998).
"Intarcia Presents Positive ITCA 650 Phase 2 Study Results for Type 2 Diabetes at EASD," Intarcia Therapeutics, Inc. (Sep. 22, 2010) (Press Release).
Quesada et al., "Interferons in Hematological Malignancies", eds. Baron et al., U. Tex. 487-495 (1987).
Quintanar-Guerrero et al., "Applications of the ion-pair concept to hydrophilic substances with special emphasis on peptides," Pharm. Res. 14(2):119-127 (1997).
Rajkumar et al., "Phase I evaluation of radiation combined with recombinant interferon alpha-2a and BCNU for patients with high-grade glioma," Int'l J. Radiat. Oncol. Biol. Phys. 40(2):297-302 (Jan. 15, 1998).
Roche Pharmaceuticals, Roferon®-A (Interferon alfa-2a, recombinant), 22 pages (2003).
Roff et al., "Handbook of Common Polymers", Cleveland Rubber Co. 72 pages (1971).
Rogers et al., "Permeability Valves," Ind. & Eng. Chem. 49(11):1933-1936 (Nov. 17, 1957).
Roman et al., "Cholestasis in the rat by means of intravenous administration of cyclosporine vehicle, Cremophor EL," Transplantation 48(4);554-558 (1989).
Roth et al., "High Dose Etretinate and Interferon-alpha—A Phase I Study in Squamous Cell Carcinomas and Transitional Cell Carcinomas," Acta Oncol. 38(5):613-617 (1999).
Roth et al., "Combination therapy with amylin and peptide YY[3-36] in obese rodents: anorexigenic synergy and weight loss additivity," Endocrinol. 148(12):6054-61 (Dec. 2007).

(56) References Cited

OTHER PUBLICATIONS

Schepp, W. et al., "Exendin-4 and exendin-(9-39)NH2: agonist and antagonist, respectively, at the rat parietal cell receptor for glucagon-like peptide-1-(7-36)NH2," Eur. J. Pharmacol., 269(2):183-191 (1994).
Schering Corp., Intron® A for Injection, 6 pages (2001).
Schering Corp., PEG-Intron™ (Peginterferon alfa-2b) Powder for Injection, 29 pages (2003).
Schmalfub, et al., "Modification of drug penetration into human skin using microemulsions," J. Controlled Release 46(3):279-285 (1997).
Sen et al., "The interferon system: a bird's eye view of its biochemistry," J. Biol. Chem. 267(8):5017-5020 (Mar. 1992).
Shiffman et al., "A decline in HCV-RNA level during interferon or ihterferon/ribavirin therapy in patients with virologic nonresponse is associated with an improvement in hepatic histology," Prog. Abstr. 50th Annu. Mtg. Postgrad. Courses Am. Assn. Study Liver Dis., Dallas, TX (Nov. 5-9, 1999) (Abstract 567).
Shima et al., "Serum total bile acid level as a sensitive indicator of hepatic histological improvement in chronic hepatitis C patients responding to interferon treatment," J. Gastroenterol. Hepatol. 15(3):294-299 (Mar. 2000).
Shiratori et al., "Histologic improvement of fibrosis in patients with hepatitis C who have sustained response to interferon therapy," Ann. Int. Med. 132(7):517-524 (Apr. 2000).
Simon et al., "A longitudinal study of T1 hypointense lesions in relapsing MS: MSCRG trial of interferon β1a," Neurology 55(2):185-192 (Jul. 2000).
Sparks, J. D. et al., "Lipoprotein alterations in 10- and 20-week-old Zucker diabetic fatty rats: hyperinsulinemic versus insulinopenic hyperglycemia," Metabolism, 47(11):1315-1324 (1998).
Sulkowskii et al., "Pegylated Interferon Alfa-2A (Pegasys™) and Ribavirin Combination Therapy for Chronic Hepatitis C: A Phase II Open-Label Study," Gastroenterology 118(4, Supp. 2) (2000) (Abstract 236).
Sulkowski, M., et al., "Peginterferon-α-2a (40kD) and ribavirin in patients with chronic hepatitis C: a phase II open label study," Biodrugs 16(2):105-109 (2002).
Talpaz et al., "Phase I study of polyethylene glycol formulation of interferon alpha-2B (Schering 54031) in Philadelphia chromosome-positive chronic myelogenous leukemia," Blood 98(6):1708-1713 (2001).
Talsania, T., et al., "Peripheral exendin-4 and peptide YY(3-36) synergistically reduce food intake through different mechanisms in mice," Endocrinology 146(9):3748-56 ( Sep. 2005).
Tanaka, H., et al., "Effect of interferon therapy on the incidence of hepatocellular carcinoma and mortality of patients with chronic hepatitis C: a retrospective cohort study of 738 patients," Int. J. Cancer 87(5):741-749 (Sep. 2000).
Tong et al., "Prediction of response during interferon α 2b therapy in chronic hepatitis C patients using viral and biochemical characteristics: a comparison," Hepatology 26(6):1640-01645 (Dec. 1997).
Touza Rey et al., "The clinical response to interferon-γ in a patient with chronic granulomatous disease and brain abscesses due to Aspergillus fumigatus," Ann. Med. Int. 17(2):86-87 (Feb. 2000).
Trudeau et al., "A phase I study of recombinant human interferon alpha-2b combined with 5-fluorouracil and cisplatin in patients with advanced cancer," Cancer Chemother. Pharmacol. 35(6):496-500 (1995).
Tseng, C. C. et al., "Glucose-dependent insulinotropic peptide: structure of the precursor and tissue-specific expression in rat," PNAS USA, 90(5):1992-1996 (1993).
Tsung et al., "Preparation and Stabilization of Heparin/Gelatin Complex Coacervate Microcapsules," J. Pharm. Sci. 86(5):603-7 (May 1997).
Unniappan et al., "Effects of dipeptidyl peptidase IV on the satiety actions of peptide YY," Diabetologia; Clinical and Experimental Diabetes and Metabolism 49(8):1915-1923 (Jun. 27, 2006).
Vokes et al., "A phase I trial of concomitant chemoradiotherapy with cisplatin dose intensification and granulocyte-colony stimulating factor support for advanced malignancies of the chest," Cancer Chemother. Pharmacol. 35(4):304-312 (1995).
Vrabec, J. T., "Tympanic membrane perforations in the diabetic rat: a model of impaired wound healing," Otolaryngol. Head Neck Surg., 118(3 Pt. 1):304-308 (1998).
Wang et al., "Preferential interaction of α-tocopherol with phosphatidylcholines in mixed aqueous dispersions of phosphatidylcholine and phosphatidylethanolamine," Eur. J. Biochem. 267(21):6362-6368 (2000).
Wang et al., "Ripple phases induced by α-tocopherol in saturated diacylphosphatidylcholines," Archives of Biochem. & Biophys. 377(2):304-314 (2000).
Wang et al., "The distribution of α-tocopherol in mixed aqueous dispersions of phosphatidylcholine and phosphattidylethanolamine," Biochimica et Biophysica Acta-Biomembranes 1509(1-2):361-372 (2000).
Wang et al, "Parenteral formulations of proteins and peptides: stability and stabilizers," J. Parenter. Sci. Technol. 42(2S):S4-S26 (1988).
Weinstock-Guttman et al., "What is new in the treatment of multiple sclerosis?" Drugs 59(3):401-410 (Mar. 2000).
Weissmann et al., "The interferon genes," Prog. Nucleic Acid Res. Mol. Biol. 33:251-300 (1986).
Wright et al., "Preliminary experience with α-2b-interferon therapy of viral hepatitis in liver allograft recipients," Transplantation 53(1):121-123 (Jan. 1992).
Young et al., "Glucose-lowering and insulin-sensitizing actions of exendin-4: studies in obese diabetic (ob/ob, db/db) mice, diabetic fatty Zucker rats, and diabetic rhesus monkeys (*Macaca mulatta*)," Diabetes, 48(5):1026-1034 (1999).
Younossi et al., "The role of amantadine, rimantadine, ursodeoxycholic acid, and NSAIDs, alone or in combination with α interferons, in the treatment of chronic hepatitis C," Semin. Liver Dis. 19(Supp. 1):95-102 (1999).
Yu et al., "Preparation, characterization, and in vivo evaluation of an oil suspension of a bovine growth hormone releasing factor analog," J. Pharm. Sci. 85(4):396-401 (1996).
Zeidner et al., "Treatment of FeLV-induced immunodeficiency syndrome (feLV-FAIDS) with controlled release capsular implantation of 2',3'-dideoxycytidine," Antivir. Res. 11(3):147-0160 (Apr. 1989).
Zein, "Interferons in the management of viral hepatitis," Cytokines Cell Mol. Ther. 4(4):229-241 (Dec. 1998).
Zeuzem et al., "Peginterferon Alfa-2a in Patients with Chronic Hepatitis C," New Engl. J. Med. 343(23):1666-1672 (2000).
Zeuzem et al., "Hepatitis C virus dynamics in vivo: effect of ribavirin and interferon α on viral turnover," Hepatology 28(1):245-252 (Jul. 1998).
Zhang et al., "Report on Large Dosage Interferon to Treat 30 Cases of Viral Encephalitis," J. Clinical Pediatrics 14(2):83-84 (1996).
Zhang et al, "A new strategy for enhancing the stability of lyophilized protein: the effect of the reconstitution medium on keratinocyte growth factor," Pharm. Res. 12(10):1447-1452 (1995).
Zheng et al. "Therapeutic Effect of Interferon Varied Dose in Treating Virus Encephalitis," Beijing Med. J. 13(2):80-81 (1998).
Ziesche et al., "A preliminary study of long-term treatment with interferon γ-1b and low-dose prednisolone in patients with idiopathic pulmonary fibrosis," New Engl. J. Med. 341(17):1264-1269 (Oct. 1999).
Pratley et al., "Targeting Incretins in Type 2 Diabetes: Role of GLP-1 Receptor Agonists and DPP-4 Inhibitors," Rev. Diabet. Stud., 5(2):73-94 (2008).
Sanofi-Aventis U.S. LLC, Prescribing Information for ADLYXIN® (Lixisenatide) Injection, for Subcutaneous Use, rev. Jul. 2016, 31 pages.
Amylin Pharmaceuticals, Inc., Prescribing Information for BYETTA® (Exenatide) Injection, rev. Oct. 2009, 34 pages.
AstraZeneca Pharmaceuticals LP, Prescribing Information for BYDUREON® (Exenatide Extended-Release for Injectable Suspension), rev. Mar. 2015, 60 pages.
Novo Nordisk A/S, Prescribing Information for Victoza® (Liraglutide [rDNA Origin] Injection), Solution for Subcutaneous Use, v. 1, Jan. 2010, 23 pages.

(56) References Cited

OTHER PUBLICATIONS

GlaxoSmithKline LLC, Prescribing Information for TANZEUM® (Albiglutide) for Injection, for Subcutaneous Use, rev. Jun. 2014, 55 pages.
Eli Lilly & Company, Prescribing Information for TRULICITY® (Dulaglutide) Injection, for Subcutaneous Use, rev. Mar. 2015, 19 pages.
PCT International Search Report (PCT Article 18 and Rules 43 and 44), International Application No. PCT/US2007/017634, dated May 26, 2008, 3 pages.
PCT Written Opinion of the International Searching Authority (PCT Rule 43bis.1), International Application No. PCT/US2007/017634, dated May 26, 2008, 8 pages.
Gonzalez, et al., "Hemoglobin Alc: A Reliable and Accurate Test for Diabetes Care? A Prospective Study in Mexico," Salud Publica Mex 55:462-468 (2013).
Ahn et al., "A New Approach to Search for the Bioactive Confirmation of Glucagon: Positional Cyclization Scanning" Journal of Medicinal Chemistry, vol. 44, No. 19, (2001): 3109-3116.
Akers, et al., "Formulation Design and Development of Parenteral Suspensions," Journal of Parenteral Science & Technology, 41(3): 88-96 (1987).
Alonso, et al., "Determinants of Release Rate of Tetanus Vaccine from Polyester Microspheres," Pharmaceutical Research, 10(7):945-953 (1993).
Beck, et al., "Poly(dl-lactide-co-glycolide)/norethisterone microcapsules: An injectable biodegradable contraceptive," Biology of Reproduction, 28(1): 186-195 (1983).
Bodmeier and McGinity, "Solvent selection in the preparation of poly(dl-lactide) microspheres prepared by the solvent evaporation method," International Journal of Pharmaceutics, 43(1-2): 179-186 (Apr. 1988).
Cha and Pitt, "A one-week subdermal delivery system for I-methadone based on biodegradable microcapsules," Journal of Controlled Release, 7: 69-78 (1988).
Cha and Pitt, "The acceleration of degradation-controlled drug delivery from polyester microspheres," Journal of Controlled Release, 8: 259-265 (1989).
Cohen, et al., "Controlled delivery systems for proteins based on poly(lactic/glycolic acid) microspheres," Pharmaceutical Research, 8(6): 713-720 (1991).
Conti, et al., "Use of polylactic acid for the preparation of microparticulate drug delivery systems," Journal of Microencapsulation, 9(2): 153-166 (1992).
Hodgman, et al., Eds., Handbook of Chemistry and Physics, 35th Edition, 1024-1025 (1953).
Jalil and Nixon, "Biodegradable poly(lactic acid) and poly(lactide-co-glycolide) microcapsules: Problems associated with preparative techniques and release properties," Journal of Microencapsulation, 7(3): 297-325 (Jul.-Sep. 1990).
Lee and Timasheff, "The stabilization of proteins by sucrose," J. Biological Chem., 256(14): 7193-7201 (Jul. 1981).
Li, et al., "Prediction of solvent removal profile and effect on properties for peptide-loaded PLGA microspheres prepared by solvent extraction/evaporation method," Journal of Controlled Release, 37: 199-214 (1995).

Maa and Hsu, "Liquid-liquid emulsification by static mixers for use in microencapsulation," Journal of Microencapsulation, 13(4): 419-433 (Jul.-Aug. 1996).
Maulding, et al., "Biodegradable microcapsules: Acceleration of polymeric excipient hydrolytic rate by incorporation of a basic medicament," Journal of Controlled Release, 3: 103-117 (1986).
Mehta, et al.,"Peptide containing microspheres from low molecular weight and hydrophilic poly(d,l-lactide-co-glycolide)," Journal of Controlled Release, 41: 249-257 (1996).
Sah, et al., "A novel method of preparing PLGA microcapsules utilizing methylethyl ketone," Pharmaceutical Research, 13(3): 360-367 (1996).
Sato, et al., "Porous biodegradable microspheres for controlled drug delivery. I. Assessment of processing conditions and solvent removal techniques," Pharmaceutical Research, 5(1): 21-30 (1988).
Szayna, et al., "Exendin-4 decelerates food intake, weight gain, and fat deposition in Zucker rats," Endocrinology, 141(6): 1936-1941 (2000).
Thomasin, et al., "A contribution to overcoming the problem of residual solvents in biodegradable microspheres prepared by coacervation," Eur. J. Pharm. Biopharm., 42(1): 16-24 (1996).
Van Santbrink and Fauser, "Urinary follicle-stimulating hormone for normogonadotropic colomiphene-resistant anovulatory infertility: Prospective, randomized comparison between low dose step-up and step-down dose regimens," J. Clin. Endocrin. Metab., 82(11): 3597-3602 (1997).
Tracy et al., "Factors affecting the degradation rate of poly(lactide-co-glycolide) microspheresin vivo and in vitro." Biomaterials. 20(11:): 1057-1062 (1999).
Ertl et al., "Poly (DL-lactide-co-glycolide) microspheres as carriers for peptide vaccines," Vaccine 14(9):879-885.(1996).
Thompson et al., "Biodegradable microspheres as a delivery system for rismorelin porcine, a porcine-growth-hormone-releasing hormone," Journal of Controlled Release 43(1):9-22 (1997).
Glumetza Brochure 2009, 13 Pages.
Erowid,"Introduction to the Federal Controlled Substance Analog Act" 2001, 4 pages.
Li et al. ("Glucagon-Like Peptide-I Receptor Agonists Versus Insulin Glargine for Type 2 Diabetes Mellitus: A Systematic Review and Meta-Analysis of Randomized Controlled Trials" in Current Therapeutic Research, vol. 71, No. 4, Aug. 2010.
Georgios, et al., "Pharmacokinetics and Tolerability of Exenatide Delivered by 7-Day Continuous Subcutaneous Infusion in Healthy Volunteers", Advances in Therapy, Health Communications, Metuchen, NJ, US, vol. 32, No. 7, Jul. 10, 2015, pp. 650-661.
Yu et al., "Glucagon-like peptide 1 based therapy for type 2 diabetes", World Journal of Pediatrics vol. 4, No. 1, Feb. 1, 2008, pp. 8-13.
Taylor et al., "Day-long subcutaneous infusion of exenatide lowers glycemia in patients with type 2 diabetes", Horm Metab Res 37: 627-632 (2005).
Gao et al., "Target-Mediated Pharmacokinetic and Pharmacodynamic Model of Exendin-4 in Rats, Monkeys. and Humans," Drug Metabolism and Disposition, vol. 40, No. 5, pp. 990-997 (2012).

* cited by examiner

OSMOTIC DELIVERY SYSTEMS AND PISTON ASSEMBLIES FOR USE THEREIN

CROSS-REFERENCE TO RELATED APPLICATIONS

This application is a continuation of U.S. patent application Ser. No. 12/930,950, filed 19 Jan. 2011, which is a continuation of U.S. patent application Ser. No. 12/658,570, filed 9 Feb. 2010, now U.S. Pat. No. 7,879,028, which is a continuation of U.S. patent application Ser. No. 11/890,836, filed 8 Aug. 2007, now U.S. Pat. No. 7,682,356, which claims the benefit of U.S. Provisional Application Ser. No. 60/821,830, filed 9 Aug. 2006, and U.S. Provisional Application Ser. No. 60/930,205, filed 15 May 2007, all of which applications are herein incorporated by reference in their entireties.

TECHNICAL FIELD

The invention relates generally to osmotic delivery systems for sustained delivery of active agents in fluid environments. More specifically, the invention relates to a piston assembly used in forming a partition in the lumen of a reservoir of an osmotic delivery system.

BACKGROUND OF THE INVENTION

In osmotic delivery systems such as described in U.S. Pat. Nos. 5,728,396 and 6,524,305, a piston is positioned in the lumen of a reservoir to divide the lumen of the reservoir into two chambers. The first chamber contains an osmotic agent formulation while the second chamber contains an active agent formulation. The piston isolates the osmotic agent formulation from the active agent formulation by engaging and sealing against the wall of the reservoir. Pressure differential across the piston allows the piston to move longitudinally within the reservoir. The piston is generally required to maintain its seal with the wall of the reservoir as it moves within the reservoir. The piston is typically made of a material that is of lower hardness than the reservoir, that will deform to fit the lumen of the reservoir, and that is impermeable. Typically, the piston is made of an elastomeric material, examples of which include, but are not limited to, the following: polypropylene; rubbers such as ethyl propylene diene rubber, silicone rubber, butyl rubber, chlorinated rubber, styrene-butadiene rubber, or chloroprene rubber; and thermoplastic elastomers such as plasticized polyvinylchloride, polyurethane, SANTOPRENE® (Advanced Elastomer Systems, Akron Ohio), or C-FLEX® (Consolidated Polymer Technologies, Inc., Clearwater Fla.).

There continues to be a desire to improve compatibility and sealing of pistons with components of the osmotic delivery systems.

SUMMARY OF THE INVENTION

The present invention relates to osmotic delivery systems, active agent formulations for use therein, as well as methods of making and methods of using the osmotic delivery systems. The present invention also relates to pistons and piston assemblies. In some embodiments the pistons and piston assemblies are substantially resistant to leaching when contacted with an organic solvent or solutions comprising organic solvents, for example, suspension vehicles.

In one aspect, the invention relates to an osmotic delivery system for delivering an active agent formulation in a fluid environment. The osmotic delivery system comprises a reservoir comprising a lumen that contains the active agent formulation, an osmotic agent formulation, and a piston assembly positioned in the lumen to isolate the active agent formulation from the osmotic agent formulation. The piston assembly comprises a body, for example, a columnar body, constructed and arranged for positioning in the lumen. The body is typically made of material that is resistant to leaching in an organic solvent, for example, a polymeric material. The body further comprising means for engaging and sealing against a wall of the reservoir.

In one embodiment of the osmotic delivery system, the body of the piston assembly is substantially columnar and comprises a rim at a distal end thereof for engaging and sealing against the wall of the reservoir, as well as a spring retained at the distal end for biasing the rim against the wall of the reservoir. The spring may be retained in a cavity at the distal end of the columnar body. The spring may be, for example, a radial spring such as a canted coil spring. Typically the spring is made of a non-reactive metal. One or more such combination of a rim and ring may be present along the body of the piston, for example, at one distal end, at each distal end, or at one or more distal end with one or more such combinations distributed along the body of the piston between the distal ends.

In another embodiment of the osmotic delivery system, the piston assembly may comprise a body constructed and arranged for positioning in the lumen, the body being made of a material that is resistant to leaching in an organic solvent (e.g., a suitable polymeric material). The piston assembly can, for example, further comprises one or more concentric grooves, each groove formed to retain an elastomeric O-ring that provides the means for engaging and sealing against the wall of the reservoir.

In another aspect, the invention relates to a piston assembly for positioning in a lumen of a reservoir for an osmotic delivery system. The piston assembly comprises a body, for example, a columnar body, constructed and arranged for positioning in the lumen, the body being made of a material (e.g., a suitable polymeric material) that is resistant to leaching in an organic solvent, wherein the body further comprises means for engaging and sealing against a wall of the reservoir.

In one embodiment of the piston assembly, the body is substantially columnar and comprises a rim at a distal end (or, in another embodiment, a rim at each distal end) of the piston assembly for engaging and sealing against the wall of the reservoir, and a spring retained at the distal end (or at both distal ends) for biasing the rim against the wall of the reservoir. Further, one or more springs may be retained between the distal ends of the piston assembly providing one or more rim for engaging and sealing against the wall of the reservoir. Thus the piston assembly may comprise one or more means for engaging and sealing against the wall of the reservoir placed at various locations along the length of the piston assembly with, preferably, at least one such means near the distal end of the piston that comes into contact with the chamber of the reservoir that comprises organic solvent (e.g., the chamber comprising the active agent formulation).

Springs useful in the practice of the present invention include radial springs such as canted coil springs, for example, made of metal that is non-reactive with other components of the osmotic delivery system (in particular, non-reactive with the active agent formulation and/or the osmotic agent formulation).

In another embodiment of the piston assembly, the piston assembly comprises a body constructed and arranged for positioning in the lumen, wherein the body is made of a material that is resistant to leaching in an organic solvent and comprises one or more concentric grooves. Typically, each groove is formed to retain an elastomeric O-ring that provides the means for engaging and sealing against the wall of the reservoir.

In another aspect the present invention relates to an osmotic delivery system loaded with an active agent comprising one or more peptide, polypeptide or protein (e.g., a particle suspension comprising one or more peptide particles, polypeptide particles, or protein particles). In one embodiment the peptide is an interferon, for example, an interferon selected from the group consisting of alpha interferon, beta interferon, delta interferon, gamma interferon, lambda interferon, omega interferon, tau interferon, and mixtures thereof. The active agent can be, for example, a suspension formulation comprising (i) a particle formulation of peptide particles (e.g., comprising interferon), and (ii) suspended in a vehicle comprising a solvent (e.g., an organic solvent) and polymer.

In another aspect the present invention relates to the treatment of interferon-responsive disease states using the osmotic delivery system of the present invention loaded with an active agent comprising interferon. In one embodiment, the present invention relates to a method of treating hepatitis C virus (HCV) infection in a subject in need of such treatment, comprising administering an osmotic delivery system of the present invention loaded with a suspension formulation comprising alpha, beta, or omega interferon (e.g., a particle formulation comprising the selected interferon) to the subject. In another embodiment, the present invention relates to a method of treating multiple sclerosis in a subject in need of such treatment, comprising administering an osmotic delivery system of the present invention loaded with a suspension formulation comprising beta or omega interferon (e.g., a particle formulation comprising the selected interferon) to the subject.

In another aspect the present invention relates to the treatment of diabetes and/or diabetes-related diseases using the osmotic delivery system of the present invention loaded with an active agent comprising an insulinotropic peptide. In one embodiment, the present invention relates to a method of treating diabetes in a subject in need of such treatment, comprising administering an osmotic delivery system of the present invention loaded with a suspension formulation comprising glucagon like protein 1 (GLP-1) or exendin-4 (e.g., a particle formulation comprising the GLP-1 or exendin-4) to the subject.

These and other embodiments of the present invention will readily occur to those of ordinary skill in the art in view of the disclosure herein.

BRIEF DESCRIPTION OF THE FIGURES

The accompanying drawings, described below, illustrate typical embodiments of the invention and are not to be considered limiting of the scope of the invention, for the invention may admit to other equally effective embodiments. The figures are not necessarily to scale, and certain features and certain view of the figures may be shown exaggerated in scale or in schematic in the interest of clarity and conciseness.

DETAILED DESCRIPTION OF THE INVENTION

Figure 1:
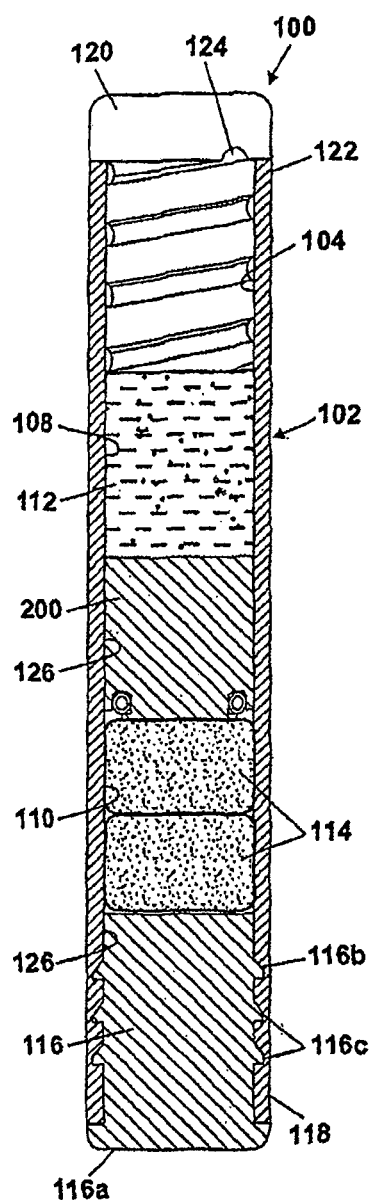
FIG. 1 depicts a cross-sectional view of an osmotic delivery system including a piston assembly.

All patents, publications, and patent applications cited in this specification are herein incorporated by reference as if each individual patent, publication, or patent application was specifically and individually indicated to be incorporated by reference in its entirety for all purposes.

1.0.0 Definitions

It is to be understood that the terminology used herein is for the purpose of describing particular embodiments only and is not intended to be limiting. As used in this specification and the appended claims, the singular forms "a," "an" and "the" include plural referents unless the context clearly dictates otherwise. Thus, for example, reference to "a polymer" includes a combination of two or more such polymers, reference to "an active agent" includes one or more active agent, mixtures of active agents, and the like.

Unless defined otherwise, all technical and scientific terms used herein have the same meaning as commonly understood by one of ordinary skill in the art to which the invention pertains. Although other methods and materials similar, or equivalent, to those described herein can be used in the practice of the present invention, the preferred materials and methods are described herein.

In describing and claiming the present invention, the following terminology will be used in accordance with the definitions set out below.

The phrase "active agent" as used herein typically refers to a pharmacologically useful compound, including, but not limited to, small molecules, peptides, and combinations thereof.

The terms "peptide," "polypeptide," and "protein" are used interchangeable herein and typically refer to a molecule comprising a chain of two or more amino acids (e.g., most typically L-amino acids, but also including, e.g., D-amino acids, modified amino acids, amino acid analogues, and/or amino acid mimetics). Peptides, polypeptides, and proteins may also comprise additional groups modifying the amino acid chain, for example, functional groups added via post-translational modification. Examples of post-translation modifications include, but are not limited to, acetylation, alkylation (including, methylation), biotinylation, glutamylation, glycylation, glycosylation, isoprenylation, lipoylation, phosphopantetheinylation, phosphorylation, selenation, and C-terminal amidation. The terms peptides, polypeptides, and proteins also include modifications of the amino terminus and/or the carboxy terminus. Modifications of the terminal amino group include, but are not limited to, des-amino, N-lower alkyl, N-di-lower alkyl, and N-acyl modifications. Modifications of the terminal carboxy group include, but are not limited to, amide, lower alkyl amide, dialkyl amide, and lower alkyl ester modifications (e.g., wherein lower alkyl is $C_1$-$C_4$ alkyl).

The term "amino acid" as used herein typically refers to naturally occurring and synthetic amino acids, as well as amino acid analogs and amino acid mimetics that function in a manner similar to the naturally occurring amino acids. Naturally occurring amino acids include those encoded by the genetic code, as well as amino acids formed by later modification, for example, hydroxyproline, gamma-carboxyglutamate, and O-phosphoserine.

The term "amino acid analogs" as used herein typically refers to compounds that have the same basic chemical structure as a naturally occurring amino acid (e.g., a carbon that is linked to: a hydrogen, a carboxyl group, an amino group, and an R group). Examples of amino acid analogs include, but are not limited to, homoserine, norleucine, methionine sulfoxide, or methionine methyl sulfonium. Such analogs generally have modified R groups (e.g., norleucine) or modified peptide backbones, but retain the same basic chemical structure as a naturally occurring amino acid.

The term "amino acid mimetics" as used herein typically refers to chemical compounds that have a structure that is different from the general chemical structure of an amino acid, but that function in a manner similar to a naturally occurring amino acid.

The terms "peptide mimetics" or "peptidomimetics" as used herein generally refer to active agents that are structurally similar to therapeutically useful peptides and that may be used to produce an equivalent therapeutic or prophylactic effect (Fauchere, J., Adv. Drug. Res. 15, 29-69 (1986); Veber and Freidinger, TINS p. 392-396 (1985); and Evans, et al., J. Med. Chem. 30:1229-1239 (1987)) and are usually developed with the aid of computerized molecular modeling. Peptidomimetics are typically structurally similar to a reference polypeptide (i.e., a polypeptide that has a selected biochemical property or pharmacological activity, for example, omega interferon, GLP-1, or exendin-4) but have one or more peptide linkages optionally replaced by a linkage selected from, but not limited to, the following: —CH2NH—; —CH2S—; —CH2-; —CH=CH— (cis and trans); —COCH2-, —CH(OH)CH2-, or —CH2SO—. Such linkages are known in the art. Such peptide mimetics may provide advantages relative to polypeptide embodiments, for example, by providing more economical production, greater chemical stability, enhanced pharmacological properties (e.g., half-life, absorption, potency, efficacy, etc.), altered specificity (e.g., a broad-spectrum of biological activities), and/or reduced antigenicity.

As used herein the terms "analog polypeptides" or "derivative polypeptides" typically refer to polypeptides comprising one or more conservative amino acid substitutions with respect to a naturally-occurring reference sequence. Analog or derivative polypeptides also refers to amino acid additions or amino acid deletions relative to the primary sequence of a reference polypeptide wherein the modification (e.g., amino acid addition or deletion) does not substantially, adversely affect the desired property of the analog polypeptide. Generally polypeptides having one or more amino acid substitution, addition, or deletion relative to a reference polypeptide have substantial identity to the reference polypeptide. The term "substantial identity" as used herein typically means that two peptide sequences, when optimally aligned, such as by the programs GAP or BESTFIT using default parameters (e.g., default gap weights), share at least about 80 percent sequence identity, preferably at least about 90 percent sequence identity, more preferably at least about 95 percent sequence identity, and most preferably at least about 98 percent sequence identity. Preferably, residue positions that are not identical differ by conservative amino acid substitutions.

As used herein the phrase "conservative amino acid substitutions" typically refers to the interchangeability of amino acid residues having similar side chains, for example, a group of amino acids having aliphatic side chains comprises glycine, alanine, valine, leucine, or isoleucine; a group of amino acids having aliphatic-hydroxyl side chains comprises serine or threonine; a group of amino acids having amide-containing side chains comprises asparagine or glutamine; a group of amino acids having aromatic side chains comprises phenylalanine, tyrosine, or tryptophan; a group of amino acids having basic side chains comprises lysine, arginine, or histidine; and a group of amino acids having sulfur-containing side chains comprises cysteine or methionine. Preferred conservative substitution groups of amino acids include, but are not limited to, valine/leucine/isoleucine (i.e., each of these three may be substituted at residues where one of them occurs), phenylalanine/tyrosine, lysine/arginine, alanine/valine, glutamic/aspartic, and asparagine/glutamine.

The term "vehicle" as used herein refers to a medium used to carry an active agent. Vehicles of the present invention typically comprise components such as polymers and solvents. The term "organic solvent" as used herein refers to organic compounds (i.e., containing carbon atoms) used to dissolve another substance (e.g., a polymer). The phrase "suspension vehicle" as used herein typically refers to solvents and polymers that are used to prepare suspension formulations of, for example, peptide particles (herein the terms peptide particle, polypeptide particle and protein particle are used interchangeably). The bodies of the piston assemblies of the present invention are generally made of one or more polymeric materials and are substantially resistant to leaching in an organic solvent that is included in a vehicle used in combination with a piston assembly.

The phrase "phase separation" as used herein refers to the formation of multiple phases (e.g., liquid or gel phases) in the suspension vehicle, such as when the suspension vehicle contacts the aqueous environment. In some embodiments of the present invention, the suspension vehicle is formulated to exhibit phase separation upon contact with an aqueous environment having less than about 50% water, preferably less than about 20% water, and more preferably less than about 10% water.

The phrase "single-phase" as used herein refers to a solid, semisolid, or liquid homogeneous system that is physically and chemically uniform throughout.

The term "dispersed" as used herein refers to dissolving, dispersing, suspending, or otherwise distributing a compound, for example, a peptide particle, in a suspension vehicle.

The phrase "chemically stable" as used herein refers to formation in a formulation of an acceptable percentage of degradation products produced over a defined period of time by chemical pathways such as deamidation (usually by hydrolysis), aggregation, or oxidation.

The phrase "physically stable" as used herein refers to formation in a formulation of an acceptable percentage of aggregates (e.g., dimers and other higher molecular weight products). Furthermore, a physically stable formulation typically will not change its physical state as, for example, from liquid to solid, from amorphous to crystal form, or interexchange between polymorphous states.

The term "viscosity" as used herein typically refers to a value determined from the ratio of shear stress to shear rate (see, e.g., Considine, D. M. & Considine, G. D., Encyclopedia of Chemistry, 4th Edition, Van Nostrand, Reinhold, N.Y., 1984) essentially as follows:

$$F/A = \mu(V/L) \quad \text{(Equation 1)}$$

where F/A=shear stress (force per unit area),
μ=a proportionality constant (viscosity), and
V/L=the velocity per layer thickness (shear rate).

From this relationship, the ratio of shear stress to shear rate defines viscosity. Measurements of shear stress and shear rate are typically determined using parallel plate rheometry performed under selected conditions (for example, at a temperature of about 37° C.). Other methods for the determination of viscosity include measurement of a kinematic viscosity using a viscometers, for example, a Cannon-Fenske viscometer, a Ubbelohde viscometer for the Cannon-Fenske opaque solution, or a Ostwald viscometer. Generally, suspension vehicles of the present invention have a viscosity sufficient to prevent a particle formulation suspended therein from settling during storage and settling during use in a method of delivery, for example, in an implantable, osmotic delivery system for delivering an active agent formulation.

The term "non-aqueous" as used herein refers to an overall moisture content, for example, of a formulation, typically of less than about 10 weight percent (wt %), preferably less than about 5 wt %, and more preferably less than about 4 wt %.

The phrase "resistant to leaching in an organic solvent" as used herein typically refers to the generation of an amount of leachates into the active agent formulation that is acceptable for pharmaceutical use. An acceptable amount of leachates generally depends on the quantity as well as toxicity of the leachates and may include determination of other factors including, but not limited to, the following: daily dose of leachates; route of administration (e.g., oral, inhaled, injected, or delivered from an implanted device); clinical vs. commercial use; and reactivity or interference of leachates with active agent, other device components, packaging, assays or product functionality. In pharmaceutical applications the amount and type of leachates are typically within tolerance limits for the subject who will be exposed to the leachates. In some embodiments of the present invention, (i) production of volatile leachates (when the piston assembly of the present invention is exposed to organic solvent) is less than between about 1.4 μg/ml and about 10 μg/ml, preferably less than about 1.4 μg/ml, from polymeric material when exposed to the organic solvent at 40° C. for about 45 days, or between about 1.4 μg/ml and about 15 μg/ml, preferably less than about 1.4 μg/ml, from polymeric material when exposed to the organic solvent at 40° C. for about 90 days or longer, and (ii) production of non-volatile leachates (when the piston assembly of the present invention is exposed to organic solvent) is less than between about 9.0 μg/ml and about 15 μg/ml, preferably less than about 9.0 μg/ml, from polymeric material when exposed to the organic solvent at 40° C. for about 45 days, or between about 9.0 μg/ml and about 20 μg/ml, preferably less than about 9.0 μg/ml, from polymeric material when exposed to the organic solvent at 40° C. for about 90 days or longer.

The phrases "sealing member," "sealing means," or "sealing device" as used herein generally refer to a device used between two parts (e.g., chambers) to prevent leakage of fluid between the parts. The sealing device is typically made of a flexible material. A sealing member between two chambers of a reservoir is typically water-tight. Examples of sealing devices include, but are not limited to, a piston assembly (e.g., where a canted coil spring biases a rim of the piston against the interior wall of the reservoir) or one or more component of the piston assembly (e.g., an O-ring, gasket, seal, packing, or the like) that contacts the inner surface of the lumen of the reservoir to provide substantial separation between the contents of the active agent chamber of the lumen of the reservoir and contents of the osmotic agent chamber of the lumen of the reservoir. The sealing member or sealing means provides substantial separation between two or more fluids contained within different regions or chambers of reservoir.

The term "subject" as used herein refers to any member of the subphylum chordata, including, without limitation, humans and other primates, including non-human primates such as rhesus macaque, chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

2.0.0 General Overview of the Invention

Before describing the present invention in detail, it is to be understood that this invention is not limited to particular types of polymeric materials, particular sources of polymers, particular polymers, and the like, as use of such particulars may be selected in view of the teachings of the present specification. It is also to be understood that the terminology used herein is for the purpose of describing particular embodiments of the invention only, and is not intended to be limiting.

In one aspect, the present invention relates to an osmotic delivery system for delivering an active agent formulation to a fluid environment, including a piston assembly comprising a body (e.g., a columnar body). In some embodiments, the piston assembly or components of the piston assembly are made of a polymeric material that is resistant to leaching in an organic solvent. In some embodiments, the piston assemblies of the present invention provide a reliable seal (e.g., a water-tight seal) between the piston assembly and the interior wall of the reservoir. In some embodiments, the piston assemblies of the present invention may comprise two or more materials to provide a reliable seal (e.g., a water-tight seal) between the piston assembly and the interior wall of the reservoir.

In one aspect, the present invention relates to an osmotic delivery system for delivery an active agent formulation to a fluid environment. The osmotic delivery system typically comprises a reservoir that defines a lumen, wherein the reservoir contains within the lumen the active agent formulation and an osmotic agent formulation. A piston assembly is typically positioned in the lumen to isolate the active agent formulation from the osmotic agent formulation. Typically the piston assembly provides a reliable seal between the piston assembly and the interior wall of the reservoir. The piston assembly, for example, comprises a body constructed and arranged for positioning in the lumen and typically the body is made of a polymeric material that is resistant to leaching in an organic solvent. The body can further comprise means for engaging and sealing against a wall of the reservoir. The piston may be movable within the reservoir in response to pressure within the reservoir. In some embodiments, the osmotic delivery system may be implantable in a subject. The reservoir can be made, for example, from an impermeable material (e.g., a titanium alloy).

The piston assembly can comprise, for example, a body constructed and arranged for positioning in the lumen. In one embodiment of the current invention, the piston assembly can include, for example, a columnar body comprising a rim at a distal end thereof for engaging and sealing against the wall of the reservoir, and a spring (e.g., a radial spring, such as a canted coil spring) retained at the distal end for biasing the rim against the wall of the reservoir. The spring may be, for example, made of a non-reactive metal. The spring may be retained in a cavity at the distal end of the columnar body. Such a columnar body may comprise one or more rims at a distal end and/or placed at other locations along the length of the columnar body, wherein the rim engages and seals against the interior wall of the reservoir, for example, by use of a retained spring.

In another embodiment, the body of the piston assembly can be made of a polymeric material that is resistant to leaching in an organic solvent and can comprise one or more concentric grooves, each groove formed to retain an elastomeric O-ring that provides the means for engaging and sealing against the wall of the reservoir. Such one or more concentric grooves can be located at one or more distal end of the body and/or placed at other locations along the length of the columnar body, wherein the elastomeric O-ring engages and seals against the interior wall of the reservoir.

In preferred embodiments, the body of the piston assembly can be made of a polymeric material that is resistant to leaching in an organic solvent. Exemplary polymeric materials include, but are not limited to, polyethylene, polyaryletherketones and ultra high molecular weight polyethylenes. The organic solvent is typically an organic solvent that is parenterally acceptable for use in a subject. Examples of organic solvents include, but are not limited to, lauryl alcohol, benzyl benzoate, benzyl alcohol, lauryl lactate, decanol, ethyl hexyl lactate, long chain ($C_8$ to $C_{24}$) aliphatic alcohols, esters, or mixtures thereof. Preferred organic solvents for use in the practice of the present invention are benzyl benzoate, benzyl alcohol, or mixtures thereof. The polymeric material preferably produces volatile leachates at a concentration of less than about 1.4 µg/ml when exposed to the organic solvent at 40° C. for at least about 45 days, more preferably for at least about 90 days. The polymeric material preferably produces non-volatile leachates at a concentration of less than about 9.0 µg/ml when exposed to the organic solvent at 40° C. for at least about 45 days, more preferably for at least about 90 days.

In some embodiments, the osmotic delivery system can, for example, include a semipermeable membrane positioned at a first end of the reservoir adjacent the osmotic agent formulation. Further, a flow modulator with an orifice for delivering the active agent formulation to the fluid environment may, for example, be positioned at a second end of the reservoir adjacent the active agent formulation.

The active agent formulation of the osmotic delivery system can comprise a suspension formulation. Examples of suspension formulations include, but are not limited to, combinations of a particle formulation and a suspension vehicle. Particle formulations can comprise a selected peptide, for example, one or more interferon (e.g., alpha interferon, beta interferon, delta interferon, gamma interferon, omega interferon, lambda interferon, tau interferon, or mixtures thereof). In preferred embodiments, the interferon can be omega interferon or beta interferon. Further, the active agent formulation may comprise a suspension formulation comprising a particle formulation comprising an insulinotropic peptide (e.g., glucagon like protein 1 (GLP-1) or exendin-4). Preferred organic solvents for use in suspension vehicles include, but are not limited to, benzyl benzoate, benzyl alcohol, or mixtures thereof.

In one embodiment of the osmotic delivery system of the present invention, the active agent formulation comprises a suspension formulation comprising a particle formulation (e.g., comprising omega interferon, sucrose, methionine, citric acid monohydrate, and sodium citrate) and a suspension vehicle (e.g., comprising, benzyl benzoate and polyvinylpyrrolidone (PVP)). The osmotic agent formulation comprises two cylindrical tablets, each tablet comprising, for example, sodium chloride salt with cellulosic and povidone binders. The piston assembly comprises a columnar body comprising a rim at a distal end thereof for engaging and sealing against the wall of the reservoir and a spring retained at the distal end for biasing the rim against the wall of the reservoir. The piston assembly comprises ultra-high molecular weight polyethylene, and the spring is a canted coil spring. This embodiment may further comprise (i) a semipermeable membrane (made of for example, polyurethane) positioned at a first end of the reservoir adjacent the osmotic agent formulation, and (ii) a flow modulator (made of, for example, polyetheretherketone) positioned at a second end of the reservoir adjacent the active agent formulation. In addition, this embodiment can be implantable in a subject.

Another aspect of this invention relates to a method of manufacturing the osmotic delivery system, comprising the reservoir, the active agent formulation, the osmotic agent formulation, the piston assembly, a semipermeable membrane and a flow modulator. Steps of the method of manufacturing may include, for example, assembling the reservoir, the active agent formulation, the osmotic agent formulation, the piston assembly, the semipermeable membrane and the flow modulator, such that the piston assembly is positioned in the lumen to isolate the active agent formulation from the osmotic agent formulation, the semipermeable membrane is positioned at a first end of the reservoir adjacent the osmotic agent formulation, and the flow modulator is positioned at a second end of the reservoir adjacent the active agent formulation.

One embodiment of the present invention relates to an osmotic delivery system for delivery an active agent formulation to a fluid environment. The osmotic delivery system comprises a reservoir (made, for example, from a titanium alloy) having a lumen that contains the active agent formulation and an osmotic agent formulation. The active agent formulation comprises a suspension formulation comprising (i) a particle formulation (e.g., comprising omega interferon, sucrose, methionine, citric acid monohydrate, and sodium citrate), and (ii) a suspension vehicle (e.g., comprising, benzyl benzoate and polyvinylpyrrolidone (PVP)). The osmotic agent formulation comprises two cylindrical tablets, each tablet comprising, for example, sodium chloride salt with cellulosic and povidone binders. A piston assembly positioned in the lumen isolates the active agent formulation from the osmotic agent formulation, wherein (i) the piston assembly comprises a columnar body having an hour-glass-like shape constructed and arranged for positioning in the lumen, and (ii) the columnar body comprises ultra-high molecular weight polyethylene. Further the columnar body has a rim at a distal end thereof for engaging and sealing against a wall of the reservoir and a canted coil spring retained at the distal end for biasing the rim against the wall of the reservoir. This embodiment comprises a semipermeable membrane (made, for example, from polyurethane) positioned at a first end of the reservoir adjacent the osmotic agent formulation, as well as a flow modulator (made, for example, from polyetheretherketone) that is positioned at a second end of the reservoir adjacent the active agent formulation.

A further aspect of the present invention relates to treating interferon-responsive diseases (e.g., multiple sclerosis or viral infection, such as, HCV infection) with a method that comprises administering the devices described herein. Typically the osmotic delivery system of the present invention is implanted in a subject to provide delivery of the active agent (e.g., interferon) at a therapeutically effective rate. The interferon used may be, for example, alpha interferon, beta interferon, omega interferon, or combinations thereof.

Another aspect of treatment relates to a method of treating diabetes or diabetes-related diseases by administering the devices described herein. Typically the osmotic delivery system of the present invention is implanted in a subject to provide delivery of the active agent (e.g., insulinotropic peptide) at a therapeutically effective rate.

In yet another aspect, the present invention relates to a piston assembly adapted for positioning in a lumen of a reservoir for an osmotic delivery system. The piston assembly typically comprises a body constructed and arranged for positioning in the lumen. The body may be made of a polymeric material that is resistant to leaching in the presence of an organic solvent. Examples of such solvents include, but are not limited to benzyl benzoate and benzyl alcohol. The body further comprises a device or means for engaging and sealing against a wall of the reservoir.

In some embodiments, the body may be a columnar body comprising a device or means for engaging and sealing against a wall of the reservoir, for example, wherein the device or means comprises a rim at a distal end of the columnar body for engaging and sealing against the wall of the reservoir, and a spring retained at the distal end for biasing the rim against the wall of the reservoir. The spring can be a canted coil spring made, for example, of a non-reactive metal.

In another embodiment, the piston assembly may comprise a body comprising one or more concentric grooves. Each groove may be formed to retain an elastomeric O-ring that provides the means for engaging and sealing against the wall of the reservoir.

Exemplary polymeric materials for the body of the piston assembly include, but are not limited to, polyethylene, polyaryletherketones and ultra high molecular weight polyethylenes. Preferably, the polymeric material produces volatile leachates at a concentration of less than about 1.4 µg/ml when exposed to the organic solvent at 40° C. for at least about 45 days, more preferably for at least about 90 days. Preferably, the polymeric material produces non-volatile leachates at a concentration of less than about 9.0 µg/ml when exposed to the organic solvent at 40° C. for at least about 45 days, more preferably for at least about 90 days.

These aspects and embodiments of the invention are described in detail with reference to a few preferred embodiments, as illustrated, for example, in the accompanying drawings. In describing some preferred embodiments herein below, numerous specific details are set forth in order to provide a thorough understanding of the invention. However, it will be apparent to one skilled in the art that the invention may be practiced without some or all of these specific details. In other instances, well-known features and/or process steps have not been described in detail so as not to unnecessarily obscure the invention. In addition, like or identical reference numerals are used to identify common or similar elements.

3.0.0 Components of an Exemplary Osmotic Delivery System

FIG. 1 presents a cross-sectional view of an example of an osmotic delivery system including a piston assembly.

FIG. 1 depicts an osmotic delivery system 100 having a reservoir 102 with a lumen 104. A piston assembly 200 is positioned in the lumen 104. The piston assembly 200 divides the lumen 104 into two chambers 108, 110. In one example, the chamber 108 contains an active agent formulation 112 and the chamber 110 contains an osmotic agent formulation 114. A semipermeable membrane 116 is positioned at a first end 118 of the reservoir 102, adjacent the chamber 110 containing the osmotic agent formulation 114. A flow modulator 120 is positioned at a second end 122 of the reservoir 102, adjacent the chamber 108 containing the active agent formulation 112. The flow modulator 120 includes a delivery orifice 124. The flow modulator 120 may be any suitable flow device having a delivery orifice. Alternatively, the second end 122 of the reservoir 102 may be closed-ended and may include the delivery orifice.

Fluid is imbibed into the chamber 110 through the semipermeable membrane 116. The active agent formulation 112 is dispensed from the chamber 108 through the delivery orifice 124 in the flow modulator 120. The piston assembly 200 engages and seals against the wall 126 of the reservoir 102, thereby isolating the osmotic agent formulation 114 and fluid imbibed through the semipermeable membrane 116 from the active agent formulation 112. At steady-state, the active agent formulation 112 is expelled through the delivery orifice 124 in the flow modulator 120 at a rate corresponding to the rate at which external fluid is imbibed into the chamber 110 through the semipermeable membrane 116.

3.1.0 Piston Assembly

The piston assembly (e.g., 200, FIG. 1) is made, in a preferred embodiment, of a material that is substantially resistant to leaching by an organic solvent, for example, that is present in the active agent formulation (e.g., 112, FIG. 1). Resistance of the piston assembly to an organic solvent means that there are minimal leachates and minimal or no dimensional changes, swelling, deformation and disintegration when the piston assembly is exposed to the organic solvent. Examples of organic solvents useful in the practice of the present invention include, but are not limited to, parenterally acceptable organic solvents, for example, lauryl alcohol, benzyl benzoate, benzyl alcohol, lauryl lactate, decanol (also called decyl alcohol), ethyl hexyl lactate, long chain ($C_8$ to $C_{24}$) aliphatic alcohols, esters, or mixtures thereof. In one embodiment, the piston assembly 200 is made of a material that is resistant to leaching by benzyl benzoate. In another embodiment, the piston assembly is made of a material that is resistant to leaching by benzyl alcohol.

Figure 2A:
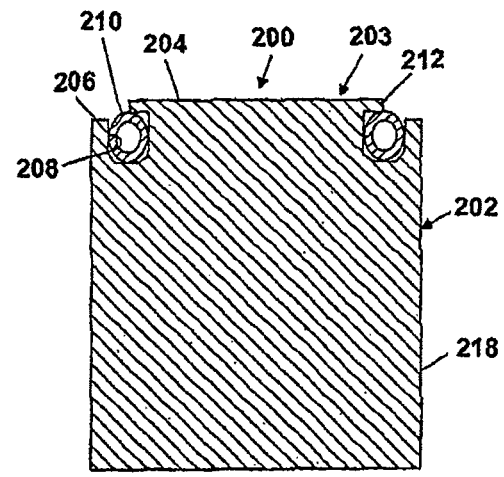
FIG. 2A is an enlarged view of the piston assembly of FIG. 1.

FIG. 2A depicts a cross-section of an example of a piston assembly. The piston assembly 200 comprises a body (e.g., a columnar body 202) that does not allow flow there through. A first distal end 203 of the columnar body 202 includes an inner ridge 204 and an outer rim 206 arranged concentrically. A cavity 208 is formed between the ridge 204 and rim 206. The cavity 208 is substantially annular in shape and may be continuous or segmented. At least one spring 210 is positioned in the cavity 208.

The spring 210 applies a radial force on the rim 206, biasing the rim 206 outwardly. Preferably, the radial force is uniformly applied about the circumference of the rim 206. In one example, the spring 210 is a canted coiled spring such as available from Bal Seal Engineering (Foothill Ranch, Calif.). A canted coil spring may be described as a round-wire spring with inclining (i.e., canted), elliptical coils. The coils deflect independently when compressed. The entire spring responds whenever any portion of a coil is deflected, permitting uniform applied radial force at each contact point of the coil spring with a surface. Canted-coil springs have been previously described (see, e.g., U.S. Pat. Nos. 4,655,462; 4,826,144; 4,830,344; 4,876,781; 4,893,795; 4,907,788; 4,915,366; 4,934,666; 4,961,253; 4,964,204; 4,974,821; 5,072,070; 5,079,388; 5,108,078; 5,117,066; 5,134,244; 5,160,122; 5,161,806; and 5,203,849). However, the invention is not limited to use of a canted coil spring. Any spring (e.g., radial spring) or spring-like means capable of exerting a radial force on the rim 206 such that the rim 206 is biased outwardly may be positioned in the cavity 208.

When the piston 200 is positioned in the lumen (104 in FIG. 1), the spring 210 biases the rim 206 against the interior wall (126 in FIG. 1) of the reservoir (102 in FIG. 1), thereby maintaining a seal between the rim 206 and the interior wall of the reservoir. The spring 210 provides a substantially constant sealing force over long periods of time, even when the material of the columnar body 202 creeps over time. The force of the spring 210 can be selected such that a seal is maintained between the piston assembly 200 and the interior wall of the reservoir during operation of the osmotic delivery system (100 in FIG. 1). The ridge 204 may include a lip 212 that partially encloses or partially covers the cavity 208 such that the lip serves to help retain the spring 210 in the cavity 208.

Figure 2B:
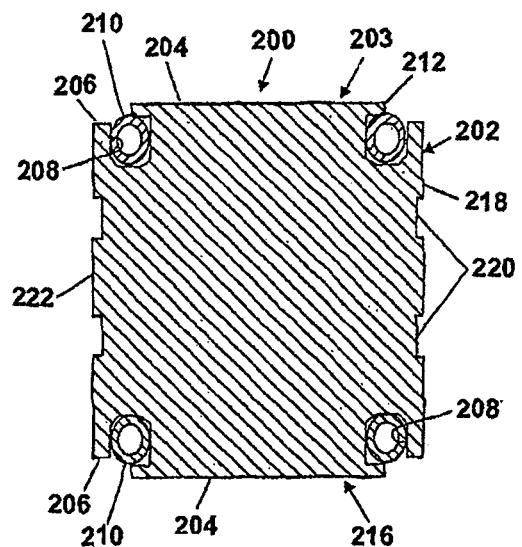
FIG. 2B depicts a cross-sectional view of a piston assembly having dual lip-seals.

In another example of the piston 200, as illustrated in FIG. 2B, a second distal end 216 of the columnar body 202, opposite the first distal end 203, may also include a rim 206, cavity 208, and ridge 204, and other features as described above for the first distal end 203 (e.g., a lip 212).

The outer surface 218 of the columnar body 202 may be smooth, as illustrated in FIG. 2A. Alternately, as illustrated in FIG. 2B, undercuts 220 and/or ribs 222 may be formed on the outer surface 218 of the columnar body 202 to further enhance the seal between the columnar body 202 and the interior wall (126 in FIG. 1) of the reservoir (102 in FIG. 1) when the piston assembly 200 is positioned in the lumen (104 in FIG. 1) of the reservoir. The cross-sectional shape of the columnar body 202 may be the same or vary along the length of the columnar body 202. For example, where undercuts 220 are formed on the columnar body 202, the cross-sectional shape of the undercut sections 220 may differ from the cross-sectional shape of the rib sections 222. The cross-sectional shape of the columnar body 202 may be circular, elliptical, or any other suitable shape. Preferably, the outer (circumferential) profile of the rim 206 conforms to the inner (circumferential) profile of the lumen of the reservoir. Therefore, where the lumen has a circular profile, the rim 206 will also preferably have a circular profile. Preferably, the outer diameter of the rim 206 is selected such that the rim 206 engages the wall of the reservoir when inserted in the lumen to prevent, for example, flow-through between the chamber 108 in FIG. 1, which comprises an active agent formulation 112 (in FIG. 1), and the chamber 110 in FIG. 1, which comprises an osmotic agent formulation 114 (in FIG. 1).

The columnar body 202 is preferably made of a polymeric material that is substantially impermeable to and substantially resistant to leaching when exposed to an organic solvent, for example, an organic solvent used in the formulation of a suspension vehicle. In one embodiment, a polymeric material that is suitable for the columnar body 202 produces volatile and non-volatile leachates less than about 1.4 µg/ml and less than about 9 µg/ml, respectively, when exposed to an organic solvent at 40° C. for about 45 days, and for about 90 days. Preferably minimal leachates occur during the course of storage and usage such that the integrity and performance of the piston assembly is not substantially, adversely affected for the intended period of storage and use. The amount of acceptable leachates can be determined depending on, for example, the toxicity of the leachate and other factors including, but not limited to, the following: daily dose of leachates; route of administration (e.g., oral, inhaled, injected, or delivered from an implanted device); clinical vs. commercial use; and reactivity or interference of leachates with active agent, other device components, packaging, assays or functionality of the osmotic delivery system. In one embodiment, the polymeric material used for the columnar body 202 is resistant to leaching in the presence of an organic solvent selected from, but not limited to, the group including lauryl alcohol, benzyl benzoate, benzyl alcohol, lauryl lactate, decanol (also called decyl alcohol), ethyl hexyl lactate, and long chain ($C_8$ to $C_{24}$) aliphatic alcohols, esters, or mixtures thereof. In a preferred embodiment, the polymeric material used for the body of the piston assembly (e.g., columnar body 202, FIG. 1) is resistant to leaching in the presence of benzyl benzoate and/or benzyl alcohol.

In one embodiment of the present invention, the body of the piston assembly is similar to the shape presented in FIG. 2B, that is columnar, but with more of an hour-glass shape (i.e. only in contact with the inner surface of the lumen near distal ends of the piston). In general the body of the piston is columnar (i.e., column-like) though one of skill in the art, in view of the teachings of the specification, can choose other shapes effective to prevent, for example, flow-through between the chamber 108 in FIG. 1, which comprises an active agent formulation 112 (in FIG. 1), and the chamber 110 in FIG. 1, which comprises an osmotic agent formulation 114 (in FIG. 1). The core of the piston assembly may be an ultra-high molecular weight polyethylene and the canted coil spring may be made of titanium alloy. The body of the piston assembly can take any form such that at least a portion of the assembly contacts the inner surface of the lumen to provide substantial separation between the contents of the active agent chamber and contents of the osmotic agent chamber of the lumen of the reservoir.

Examples of polymeric materials suitable for making the body of the piston assembly include, but are not limited to, the following: polyethylene; polyaryletherketones (e.g., polyetherketone and polyetheretherketone (PEEK)); and ultra-high-molecular-weight polyethylene. Other examples of useful polymers include, but are not limited to, the following: perfluoronated elastomers and polymers (e.g. elastomeric materials having broad chemical resistance, combining the resilience and sealing force of an elastomer with chemical resistance approaching that of polytetrafluoroethylene (PTFE) as available, for example, CHEMRAZ® (Greene, Tweed of Delaware, Inc., Wilmington Del.) materials); polyimides; and polysulfones. In a preferred embodiment the polymeric material has some natural lubricity relative to the material comprising the inner wall of the lumen. The polymeric material may be one that adheres to the wall of the reservoir upon wetting. The spring 210 retained on the columnar body 202 may be made of a metallic material. Preferably, the metallic material is non-reactive (or inert) and biocompatible. Materials used for the spring 210 may be similar to the materials used for the reservoir (102 in FIG. 1) of the osmotic delivery system, as will be further described below. Alternatively, other means to provide a seal (e.g., a water-tight seal) between the piston and the interior wall of the lumen may be employed, some of which are discussed further herein below.

In addition to use of a solid core of the polymeric materials to make the piston assembly, a thick impermeable coating of one or more of these solvent resistant polymers on a dissimilar core substrate may be used.

Furthermore, although an exemplary shape of the piston is described as a cylinder, the shape of the piston assembly may vary from a cylindrical shape (e.g., the piston may have an hour glass shape that contacts with the inner surface of the lumen near the distal ends). Shape of the piston assembly is typically such that it contacts the inner surface of the lumen to (i) provide separation between the active agent chamber and the osmotic agent chamber of the lumen, and (ii) prevent flow-through there between. In preferred embodiments, the piston assembly substantially prevents fluid exchange between the active agent chamber and the osmotic agent chamber of the lumen.

In one aspect, the piston assembly of the present invention may comprise two or more components or materials, wherein the piston effectively separates the active drug formulation from the osmotic engine. By using multiple materials or multiple components to construct a piston, each material or component may be selected to provide one or more advantages. For example, thermoplastics such as polyethylene (e.g., ultra high molecular weight polyethylene (UHMWPE)) and polyetheretherketone (PEEK) have a broad resistance to chemicals typically used in pharmaceutical applications; however, such thermoplastics typically do not have elastic properties needed to create a tight seal against the inner wall of the reservoir. However, if one or more rim/spring, spring, O-ring, gasket, seal, packing, or the like sealing means, is used with the thermoplastic material or component of the piston assembly, an acceptable seal against the inner wall of the reservoir is created. Embodiments using canted coil springs are described herein above.

Elastomers, for example, perfluoroelastomer, typically have broad chemical resistance but can be difficult and costly to mold into a one-piece piston. However, a thin, perfluoroelastomer O-ring, gasket, or coating may be installed on to or applied to on a rigid core material (e.g., thermoplastic, ceramic, metal) to create an acceptable piston seal. Such combination (or composite) pistons may help solve some problems typically associated with use of single materials or single component piston. For example, although some single materials have a broad resistance to chemicals that can be used in pharmaceutical applications, when used to create single material pistons they typically do not have elastic properties needed to create a tight seal against the inner wall of the reservoir. Also, some elastomers that are useful for creating tight seals against the inner wall of the reservoir are very expensive (e.g., perfluoroelastomer) and difficult to mold into a complete piston. As discussed herein, O-rings or the like can be formed from such elastomers thus avoiding the need to mold complete pistons from the elastomer and reducing production cost as well. Accordingly, the piston assemblies of the present invention may comprise two or more components and/or two or more materials, thus providing broader chemical compatibility with excipients, vehicles, osmotic systems, and drug substances.

Accordingly, in one aspect the present invention relates to a piston assembly or seal in a drug delivery device that is used to separate two or more fluids. The piston assembly or seal may be made from two or more materials and/or components that provide superior utility to a piston assembly made from a single material or component in the areas of, but not limited to: chemical compatibility, biocompatibility, cost, strength, system start-up, resistance to compression set (shelf stability), and part complexity. Composite piston assemblies can be cleaned, lubricated, and installed in the same or similar manner to a single component or single material pistons.

One embodiment of the present invention includes a thermoplastic core piece with a cavity that contains a canted metallic spring that supplies a sealing force to a thin flange or lip of the thermoplastic core, as shown in FIG. 2A and FIG. 2B. This type of design may incorporate multiple spring seals and be installed with either end contacting the drug formulation. The thermoplastic core has excellent chemical and biological compatibility, strength and (being incompressible) provides excellent system start-up delivery. This embodiment is described in more detail herein above.

Figures 4A, 4B:
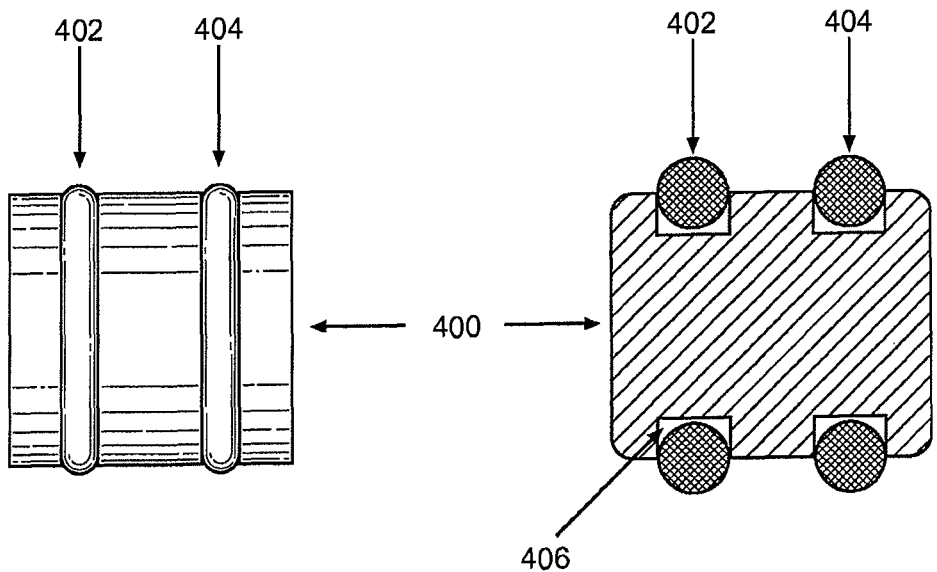
FIG. 4A depicts a side view of a piston assembly having two O-ring type sealing members.
FIG. 4B presents a schematic side view of the piston assembly of FIG. 4A.
Figure 4C:
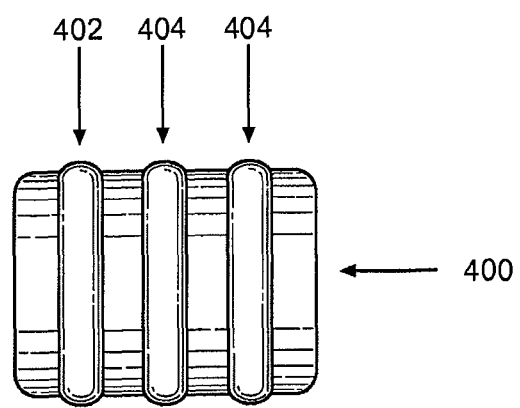
FIG. 4C depicts a side view of a piston assembly having three O-ring type sealing members.

Another aspect of the present invention includes a core (e.g., a thermoplastic core) with one or more concentric furrows, grooves or glands (i.e., a gland is a groove void) that accepts an elastomeric O-ring or gasket. The O-ring or gasket provides the seal with the inner wall of the lumen of the reservoir. Two examples of such piston assemblies are shown in FIG. 4A, FIG. 4B and FIG. 4C. Referring to FIG. 4A, two elastomeric O-rings 402 and 404 are shown. The body of the piston assembly 400 is, for example, a thermoplastic (e.g., PEEK or UHMWPE) or titanium alloy core. The O-rings 402 and 404 may be made of the same or different materials. In one embodiment, the O-ring that forms a seal relative to the reservoir chamber comprising an organic solvent may be made of a material resistant to damage or degradation by the solvent. For example, O-ring 402 may be made of a perfluoroelastomer. The second O-ring 404 that forms a seal relative to the reservoir chamber comprising the osmotic agent may be made of a different material, for example, a fluoroelastomer or other elastomer. FIG. 4B presents a schematic view of the piston assembly shown in FIG. 4A. In addition to the O-rings 402 and 404, and the body 400, FIG. 4B illustrates the groove or gland 406 formed by the body of the piston assembly into which the O-rings are seated.

Another piston assembly with multiple O-rings is illustrated in FIG. 4C. In FIG. 4C, three O-rings 402 and 404 are shown. As described above, these O-rings may all be made of the same or similar material, or the O-rings may be made of a variety of materials. For example, in one embodiment, the O-ring that forms a seal relative to the reservoir chamber comprising an organic solvent may be made of a material resistant to damage or degradation by the solvent. For example, O-ring 402 may be made of a perfluoroelastomer. The second and third O-rings 404 that form a seal relative to the reservoir chamber comprising the osmotic agent may be made of a different material, for example, a fluoroelastomer or other elastomer. The body of the piston assembly 400 may be made of a variety of materials as described herein and may also assume a number of suitable shapes including, but not limited to, a substantially columnar body.

A thermoplastic core may provide excellent chemical and biological compatibility and (being incompressible) also provide excellent system start-up delivery. The elastomeric O-rings or gaskets can be small to keep cost low (e.g., perfluoroelastomer) or different composition O-rings or gaskets may be used on the same piston if the fluids being separated have different solvating powers (e.g., saturated salt solution versus an organic solvent drug suspension). The elastomeric seals can be, for example, separate components installed into the glands, or they may be attached to the thermoplastic core by an over-molding or bonding process.

One embodiment of the present invention is the ability to control the amount of leachates produced from the piston assembly by careful selection of materials for making the piston assembly in view of organic solvent components that contact the piston assembly. In other embodiments, the piston assemblies of the present invention are useful with a wide variety of pharmaceutical excipients and provide several general advantages over previously used piston assemblies. For example, the use of two or more materials can be used to provide a reliable seal (e.g., a water-tight seal) between the piston assembly and the interior wall of the reservoir, and the use of two or more materials can provide easier manufacturing of the piston assembly and can provide cost savings as well. Further, the piston assemblies of the present invention provide acceptable operation of the piston and the osmotic delivery system for long periods of time, for example, greater than about 45 days, preferably greater than about 90 days, more preferably greater than about 180 days, more preferably greater than about 365 days. In addition, the piston assemblies of the present invention produce pharmaceutically acceptably low levels or less of volatile and non-volatile leachates when used in combination with organic solvents.

The piston assemblies described herein may be used, for example, in osmotic delivery systems such as the DUROS® (ALZA Corporation, Palo Alto Calif.) delivery system or similar system (see, e.g., U.S. Pat. Nos. 5,728,396; 5,985,305; 5,997,527; 6,113,938; 6,132,420; 6,156,331; 6,217,906; 6,261,584; 6,270,787; 6,287,295; 6,395,292; 6,508,808; 6,544,252; 6,635,268; 6,682,522; 6,923,800; 6,939,556; 6,976,981; 6,997,922; 7,014,636; 7,112,335; 7,163,688).

The DUROS® device releases an active agent at a predetermined rate based on the principle of osmosis. Extracellular fluid (e.g., from the fluid environment into which the device was placed, for example, by implantation in a subject) enters the DUROS® device through a semi-permeable membrane directly into a salt engine that expands to drive the piston at a slow and even delivery rate. Movement of the piston forces the drug formulation to be released through the orifice or exit port.

Implantable devices, for example, the DUROS® device, provide the following advantages for administration of a suspension formulations: true zero-order release of the active agent pharmacokinetically; long-term release period time (e.g., up to about 12 months); and reliable delivery and dosing of the active agent.

3.2.0 Semipermeable Membrane

The reservoir (e.g., 102, FIG. 1) may be sized such that it can be implanted within a body. The first end (e.g., 118, FIG. 1) may be open, and the semipermeable membrane (e.g., 116, FIG. 1) may be provided as a plug which is inserted in the open end (e.g, 118, FIG. 1). Such a plug may be, for example, inserted by press-fitting or using screw/thread-like means. Alternately, the semipermeable membrane (e.g., 116, FIG. 1) may be integral with the end (e.g., 118, FIG. 1) of the reservoir (e.g., 102, FIG. 1).

In one embodiment of the semipermeable membrane as a plug, the semipermeable membrane 116 may include an enlarged portion 116a that acts as a stop member engaging the first end 118 of the reservoir 102. The outer surface 116b of the semipermeable membrane 116 may have ribs 116c that engage the wall 126 of the reservoir 102, thereby locking the semipermeable membrane 116 to the reservoir 102 and allowing a seal to be formed between the reservoir 102 and the semipermeable membrane 116. The wall 126 of the reservoir 102 may also include undercuts that engage the ribs 116c on the semipermeable membrane 116. The semipermeable membrane 116 acts as a one-way valve, allowing flow into the chamber 110 from an external fluid environment while preventing flow out of the chamber 110 to the external fluid environment.

Semipermeable materials suitable for the semipermeable membrane (e.g., 116, FIG. 1) are those that can conform to the shape of the lumen (e.g., 104, FIG. 1) of the reservoir (e.g., 102, FIG. 1) upon wetting. Preferably, these materials can also adhere to the wall (e.g., 126, FIG. 1) of the reservoir (e.g., 102, FIG. 1) upon wetting, thereby providing or maintaining a seal between the wall (e.g., 126, FIG. 1) and the semipermeable membrane (e.g., 116, FIG. 1). Typically, these semipermeable materials are polymeric materials, which can be selected based on the permeability of the membrane and system configuration requirements. Examples of suitable semipermeable materials include, but are not limited to, plasticized cellulosic materials; enhanced polymethyl methacrylates (PMMAs) such as hydroxyethylmethacrylate (HEMA); and elastomeric materials such as polyurethanes and polyamides, polyether-polyamind copolymers, thermoplastic copolyesters; and the like.

Generally the membrane permeability ranges of the polymeric material is selected in order to provide the appropriate influx of aqueous solution into the lumen of the osmotic delivery system such that the osmotic agent expands at a rate determined to provide delivery of an active agent at a desired rate for a selected period of time. Table 1 presents examples of water permeability ranges for membranes for a 150 µl nominal volume osmotic delivery system.

TABLE 1

| System duration [months] | 1 | 3 | 6 | 12 |
|---|---|---|---|---|
| Water Permeability [µl/day] | 4.5-5.5 | 1.4-1.7 | 0.8-0.9 | 0.37-0.40 |

The semipermeable membrane material is typically selected based on, for example, the equilibrium water absorption percent of the polymeric material and/or the polymeric material's dynamic water permeability rate.

In one embodiment of the present invention, the semipermeable membrane is an aliphatic, polyether-based polyurethane having a nominal equilibrium water absorption of 33%. The thermoplastic polyurethane may be injection molded to form a membrane with four barbed, concentric ribs and an enlarged portion (e.g., 116a, FIG. 1) that acts as a stop member.

3.3.0 Osmotic Agent

The osmotic agent (or water-swellable agent) formulation (e.g., in chamber 110, FIG. 1) is preferably a tissue tolerable formulation whose high osmotic pressure and high solubility propels the active agent over a long period of time while remaining in saturated solution in the water admitted by the semipermeable membrane. The osmotic agent is preferably selected for tolerability by subcutaneous tissue, at least at pumping rates and hypothetically resulting concentrations to allow inadvertent dispensing from implanted devices left in the patient for a longer than the labeled period. In preferred embodiments, the osmotic agent does not diffuse or permeate through the piston assembly to any appreciable amount (e.g., less than about 10%, more preferably less than about 8%, more preferably less than about 6%) under normal operating conditions.

The osmotic agent formulation may be, for example, in the form of tablets as shown in 114, FIG. 1. One or more such tablets may be used. Alternatively, the osmotic agent formulation may have other shape, texture, density, or consistency. For example, the osmotic agent formulation may be a slurry, a tablet, a molded or extruded material, a powder or granular form, or other form known in the art. The osmotic agent formulation may include one or more osmotic polymers. An osmotic polymer is a hydrophilic polymer that can imbibe aqueous fluids (such as biological fluids and water) and upon imbibing aqueous fluids expands to an equilibrium state and retains a significant portion of the imbibed fluid. An osmotic polymer can expand to a very high degree, for example, about 2 to about 50 times its initial volume. An osmotic polymer may or may not be cross-linked. Preferred osmotic polymers are hydrophilic polymers that are lightly cross-linked, such cross-links being formed by covalent or ionic bonds or residue crystalline regions after swelling. Osmotic polymers may be, for example, of plant, animal or synthetic origin.

Examples of osmotic polymers suitable for use in the osmotic agent formulation (e.g., 114, FIG. 1) include, but are not limited to, poly (hydroxy-alkyl methacrylate) having a molecular weight of from 30,000 to 5,000,000; polyvinylpyrrolidone (PVP) having a molecular weight of from 10,000 to 360,000; anionic and cationic hydrogels; polyelectrolytes complexes; polyvinyl alcohol having a low acetate residual, cross-linked with glyoxal, formaldehyde, or glutaraldehyde and having a degree of polymerization of from 200 to 30,000; a mixture of methyl cellulose, cross-linked agar and carboxymethyl cellulose; a mixture of hydroxypropyl methylcellulose and sodium carboxymethylcellulose; a mixture of hydroxypropyl ethylcellulose and sodium carboxymethyl cellulose; sodium carboxymethylcellulose; potassium carboxymethylcellulose; a water insoluble, water swellable copolymer formed from a dispersion of finely divided copolymer of maleic anhydride with styrene, ethylene, propylene, butylene or isobutylene cross-linked with from 0.001 to about 0.5 moles of saturated cross-linking agent per mole of maleic anhydride per copolymer; water swellable polymers of N-vinyl lactams; polyoxyethylene-polyoxypropylene gel; polyoxybutylene-polyethylene block copolymer gel; carob gum; polyacrylic gel; polyester gel; polyuria gel; polyether gel; polyamide gel; polypeptide gels; polyamino acid gels; polycellulosic gel; polygum gel; and initially dry hydrogels that imbibe and absorb water that penetrates the glassy hydrogel and lowers its glass temperature.

Other examples of osmotic polymers include, but are not limited to, the following: polymers that form hydrogels such as CARBOPOL® (Noveon, Inc., Cleveland Ohio), acidic carboxypolymer, a polymer of acrylic and cross-linked with a polyallyl sucrose, also known as carboxypolymethylene and carboxyvinyl polymer having a molecular weight of 250,000 to 4,000,000; cynamer polyacrylamides; cross-linked water swellable indene-maleic anhydride polymers; GOOD-RITE® (Noveon, Inc., Cleveland Ohio) polyacrylic acid having a molecular weight of 80,000 to 200,000; POLYOX® (Union Carbide Chemicals & Plastics Technology Corporation, Danbury Conn.) polyethylene oxide polymer having a molecular weight of 100,000 to 5,000,000 and higher; starch graft copolymers; acrylate polymer polysaccharides composed of condensed glucose units such as diester cross-linked polygluran; and the like.

The osmotic agent formulation may include an osmotic effective solute either in addition to or in lieu of the osmotic polymer described above. Osmotic effective solutes include inorganic and organic compounds that can exhibit an osmotic pressure gradient across the semipermeable membrane when the osmotic delivery system is placed in a fluid environment. An osmotic effective solute in the osmotic agent formulation (e.g., 114, FIG. 1) imbibes fluid into the chamber (e.g., 110, FIG. 1) through the semipermeable membrane (e.g., 116, FIG. 1), thereby making available fluid pressure to displace the piston assembly (e.g., 200, FIG. 1) and push the active agent formulation (e.g., 112, FIG. 1) through the delivery orifice (e.g., 124, FIG. 1) via the flow modulator (e.g., 120, FIG. 1). Osmotic effective solutes or osmagents (i.e., the non-volatile species that are soluble in water and create the osmotic gradient driving the osmotic inflow of water) useful in the osmotic agent formulation include, but are not limited to, magnesium sulfate, magnesium chloride, sodium chloride, potassium sulfate, sodium sulfate, lithium sulfate, sodium phosphate, potassium phosphate, d-mannitol, urea, inositol, magnesium succinate, tartaric acid, inositol, carbohydrates, and various monosaccharides, oligosaccharides and polysaccharides such as sucrose, glucose, lactose, fructose, raffinose and dextran, as well as mixtures of any of these various species.

Osmotic agents such as sodium chloride (NaCl) with appropriate tabletting agents (lubricants and binders; e.g., cellulosic and povidone binders) and viscosity modifying agents, such as sodium carboxymethylcellulose or sodium polyacrylate are examples of preferred osmotic agents. Other osmotic agents useful as the water-swellable agent include osmopolymers and osmagents and are described, for example, in U.S. Pat. No. 5,413,572. A liquid or gel additive or filler may be added to chamber 20 to exclude air from spaces around the osmotic engine. Exclusion of air from the devices generally means that delivery rates will be less affected by nominal external pressure changes (e.g., about +/−7 p.s.i. (+/−5 a.t.m.)).

An osmotic tablet is an osmotic agent that is a fluid-attracting agent used to drive the flow of the active agent. The osmotic agent may be an osmagent, an osmopolymer, or a mixture of the two. Species which fall within the category of osmagent (i.e., the non-volatile species which are soluble in water and create the osmotic gradient driving the osmotic inflow of water) vary widely. Examples of such osmagents are well known in the art and include those listed herein above. The osmotic agent 114 in FIG. 1 is illustrated as osmotic tablets. Osmotic tablets may, for example, comprise sodium chloride, sodium carboxymethylcellulose, polyvinylpyrrolidone (PVP), magnesium stearate, and water for injection.

The osmotic agent may be manufactured by a variety of techniques, many of which are known in the art (see, e.g., U.S. Pat. Nos. 6,923,800 and 6,287,295). In one such technique, an osmotically active agent is prepared as solid or semi-solid formulations and pressed into pellets or tablets whose dimensions correspond to slightly less than the internal dimensions of the respective chambers that they will occupy in the enclosure interior. Depending on the nature of the materials used, the agent and other solid ingredients that may be included may be processed prior to the formation of the pellets by such procedures as ball-milling, calendaring, stirring or roll-milling to achieve a fine particle size and fairly uniform mixtures of each ingredient. The enclosure for pressing the osmotic agent into tablets or pellets may be formed from a wall-forming material by the use of a mold, with the materials applied either over the mold or inside the mold, depending on the mold configuration.

3.4.0 Active Agent

The active agent formulation (e.g., 112, FIG. 1) may comprise one or more active agents. The active agent may be any physiologically or pharmacologically active substance, particularly those known to be delivered to the body of a human or an animal such as medicaments, vitamins, nutrients, or the like. Active agents that may be delivered by the osmotic delivery system of the present invention include, but are not limited to, drugs that act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system or the central nervous system. Further, active agents that may be delivered by the osmotic delivery system of the present invention include, but are not limited to, active agents used for the treatment of infectious diseases, chronic pain, diabetes, auto-immune disorders, endocrine disorders, metabolic disorders, and rheumatologic disorders.

Suitable active agents include, but are not limited to, the following: peptides, proteins, polypeptides (e.g., enzymes, hormones, cytokines), polynucleotides, nucleoproteins, polysaccharides, glycoproteins, lipoproteins, steroids, analgesics, local anesthetics, antibiotic agents, anti-inflammatory corticosteroids, ocular drugs, other small molecules for pharmaceutical use (e.g., ribavirin), or synthetic analogs of these species, as well as mixtures thereof. Preferred active agents include macromolecules (e.g., peptides, proteins and polypeptides) or active agents that are highly potent.

The osmotic devices of the invention may be used to deliver a wide variety of active agents. These agents include, but are not limited to, pharmacologically active peptides proteins, polypeptides, genes, gene products, other gene therapy agents, or other small molecules. The polypeptides may include but are not limited to the following: growth hormone; somatostatin; somatropin, somatotropin, somatotropin analogues, somatomedin-C, somatotropin plus an amino acid, somatotropin plus a protein; follicle stimulating hormone; luteinizing hormone, luteinizing hormone-releasing hormone (LHRH), LHRH analogues such as leuprolide, nafarelin and goserelin, LHRH agonists or antagonists; growth hormone releasing factor; calcitonin; colchicine; gonadotropic releasing hormone; gonadotropins such as chorionic gonadotropin; oxytocin, octreotide; vasopressin; adrenocorticotrophic hormone; epidermal growth factor; fibroblast growth factor; platelet-derived growth factor; transforming growth factor; nerve growth factor; prolactin; cosyntropin; lypressin polypeptides such as thyrotropin releasing hormone; thyroid stimulation hormone; secretin; pancreozymin; enkephalin; glucagon; endocrine agents secreted internally and distributed by way of the bloodstream; or the like.

Further active agents that may be delivered include but are not limited to the following: alpha antitrypsin; factor VII; factor IX and other coagulation factors; insulin; peptide hormones; adrenal cortical stimulating hormone, thyroid stimulating hormone and other pituitary hormones; erythropoietin; growth factors such as granulocyte-colony stimulating factor, granulocyte-macrophage colony stimulating factor, insulin-like growth factor 1; tissue plasminogen activator; CD4; 1-deamino-8-D-arginine vasopressin; interleukin-1 receptor antagonist; tumor necrosis factor, tumor necrosis factor receptor; tumor suppresser proteins; pancreatic enzymes; lactase; cytokines, including lymphokines, chemokines or interleukins such as interleukin-1, interleukin-2; cytotaxic proteins; superoxide dismutase; endocrine agents secreted internally and distributed in an animal by way of the bloodstream; recombinant antibodies, antibody fragments, humanized antibodies, single chain antibodies, monoclonal antibodies; avimers; or the like.

Further, the active agents that may be administered include inorganic and organic compounds without limitation including those compounds that transport across a vessel. Examples of active agents that may be used in the practice of the present invention include, but are not limited to, the following: hypnotics and sedatives such as pentobarbital sodium, phenobarbital, secobarbital, thiopental, amides and ureas exemplified by diethylisovaleramide and alpha-bromo-isovaleryl urea, urethanes, or disulfanes; heterocyclic hypnotics such as dioxopiperidines, and glutarimides; antidepressants such as isocarboxazid, nialamide, phenelzine, imipramine, tranylcypromine, pargyline); tranquilizers such as chloropromazine, promazine, fluphenazine reserpine, deserpidine, meprobamate, benzodiazepines such as chlordiazepoxide; anticonvulsants such as primidone, diphenylhydantoin, ethltoin, pheneturide, ethosuximide; muscle relaxants and anti-parkinson agents such as mephenesin, methocarbomal, trihexylphenidyl, biperiden, levo-dopa, also known as L-dopa and L-beta-3-4-dihydroxyphenylalanine; analgesics such as morphine, codeine, meperidine, nalorphine; antipyretics and anti-inflammatory agents such as aspirin, salicylamide, sodium salicylamide, naproxin, ibuprofen; local anesthetics such as procaine, lidocaine, naepaine, piperocaine, tetracaine, dibucane; antispasmodics and antiulcer agents such as atropine, scopolamine, methscopolamine, oxyphenonium, papaverine, prostaglandins such as $PGE_1$, $PGE_2$, $PGF_{1alpha}$, $PGF_{2alpha}$, PGA; antimicrobials such as penicillin, tetracycline, oxytetracycline, chlorotetracycline, chloramphenicol, sulfonamides, tetracycline, bacitracin, chlorotetracycline, erythromycin; anti-malarials such as 4-aminoquinolines, 8-aminoquinolines and pyrimethamine; hormonal agents such as prednisolone, cortisone, cortisol and triamcinolone, androgenic steroids (for example, methyltestosterone, fluoxmesterone), estrogenic steroids (for example, 17-beta-estradoil and thinyl estradiol), progestational steroids (for example, 17-alpha-hydroxyprogesterone acetate, 19-nor-progesterone, norethindrone); sympathomimetic drugs such as epinephrine, amphetamine, ephedrine, norepinephrine; cardiovascular drugs such as procainamide, amyl nitrate, nitroglycerin, dipyridamole, sodium nitrate, mannitol nitrate; diuretics such as acetazolamide, chlorothiazide, flumethiazide; antiparasitic agents such as bephenium hydroxynaphthoate, dichlorophen, enitabas, dapsone; neoplastic agents such as mechloroethamine, uracil mustard, 5-fluorouracil, 6-thioguanine and procarbazine; hypoglycemic drugs such as insulin related compounds (for example, isophane insulin suspension, protamine zinc insulin suspension, globin zinc insulin, extended insulin zinc suspension) tolbutamide, acetohexamide, tolazamide, chlorpropamide; nutritional agents such as vitamins, essential amino acids, and essential fats; eye drugs such as pilocarpine base, pilocarpine hydrochloride, pilocarpine nitrate; antiviral drugs such as disoproxil fumarate, aciclovir, cidofovir, docosanol, famciclovir, fomivirsen, foscarnet, ganciclovir, idoxuridine, penciclovir, trifluridine, tromantadine, valaciclovir, valganciclovir, vidarabine, amantadine, arbidol, oseltamivir, peramivir, rimantadine, zanamivir, abacavir, didanosine, emtricitabine, lamivudine, stavudine, zalcitabine, zidovudine, tenofovir, efavirenz, delavirdine, nevirapine, loviride, amprenavir, atazanavir, darunavir, fosamprenavir, indinavir, lopinavir, nelfinavir, ritonavir, saquinavir, tipranavir, enfuvirtide, adefovir, fomivirsen, imiquimod, inosine, podophyllotoxin, ribavirin, viramidine, fusion blockers specifically targeting viral surface proteins or viral receptors (for example, gp-41 inhibitor (T-20), CCR-5 inhibitor); anti-nausea such as scopolamine, dimenhydrinate); iodoxuridine, hydrocortisone, eserine, phospholine, iodide, as well as other beneficial active agents.

Numerous peptides, proteins, or polypeptides that are useful in the practice of the present invention are described herein. In addition to the peptides, proteins, or polypeptides described, modifications of these peptides, proteins, or polypeptides are also known to one of skill in the art and can be used in the practice of the present invention following the guidance presented herein. Such modifications include, but are not limited to, amino acid analogs, amino acid mimetics, analog polypeptides, or derivative polypeptides. Further, the active agents disclosed herein may be formulated singly or in combination (e.g., mixtures).

Some embodiments of the present invention comprise use of interferon peptides (e.g., alpha, beta, delta, gamma, lambda, omega, tau interferon, as well as analogs or derivatives thereof such as pegylated forms; see, for example, *The Interferons: Characterization and Application*, by Anthony Meager (Editor), Wiley-VCH (May 1, 2006)) or peptide hormones for the treatment of diabetes and diabetes related conditions (e.g., insulinotropic peptides such as glucagon like protein (such as GLP-1), as well as analogues and derivatives thereof, or exendins (such as exendin-4), as well as analogs and derivatives thereof).

GLP-1 (including three forms of the peptide, GLP-1(1-37), GLP-1(7-37) and GLP-1(7-36)amide, as well as analogs of GLP-1) have been shown to stimulate insulin secretion (i.e., it is insulinotropic) which induces glucose uptake by cells and results in decreases in serum glucose levels (see, e.g., Mojsov, S., Int. J. Peptide Protein Research, 40:333-343 (1992)).

Numerous GLP-1 derivatives and analogues demonstrating insulinotropic action are known in the art (see, e.g., U.S. Pat. Nos. 5,118,666; 5,120,712; 5,512,549; 5,545,618; 5,574,008; 5,574,008; 5,614,492; 5,958,909; 6,191,102; 6,268,343; 6,329,336; 6,451,974; 6,458,924; 6,514,500; 6,593,295; 6,703,359; 6,706,689; 6,720,407; 6,821,949; 6,849,708; 6,849,714; 6,887,470; 6,887,849; 6,903,186; 7,022,674; 7,041,646; 7,084,243; 7,101,843; 7,138,486; 7,141,547; 7,144,863; and 7,199,217). Accordingly, for ease of reference herein, the family of GLP-1 derivatives and analogues having insulinotropic activity is referred to collectively as GLP-1.

The exendins are peptides that were isolated from the venom of the Gila-monster. Exendin-4 is present in the venom of *Heloderma suspectum* (Eng, J., et al., J. Biol. Chem., 265:20259-62 (1990); Eng., J., et al., J. Biol. Chem., 267:7402-05 (1992); U.S. Pat. No. 5,424,286). The exendins have some sequence similarity to several members of the glucagon like peptide family, with the highest homology, 53%, being to GLP-1(7-36)amide (Goke, et al., J. Biol. Chem., 268:19650-55 (1993)).

Exendin-4 acts at GLP-1 receptors on insulin-secreting beta-TC1 cells, dispersed acinar cells from guinea pig pancreas, and parietal cells from stomach. The exendin-4 peptide also stimulates somatostatin release and inhibits gastrin release in isolated stomachs (Goke, et al., J. Biol. Chem. 268:19650-55 (1993); Schepp, et al., Eur. J. Pharmacol., 69:183-91 (1994); Eissele, et al., Life Sci., 55:629-34 (1994)). Based on their insulinotropic activities, use of exendin-3 and exendin-4 for the treatment of diabetes mellitus and the prevention of hyperglycemia has been proposed (see, e.g., U.S. Pat. No. 5,424,286).

Exendin-4 has similar properties to GLP-1 in that, for example, it regulates gastric emptying, insulin secretion, food intake, and glucagon secretion.

Numerous exendin-4 derivatives and analogues (including, e.g., exendin-4 agonists) demonstrating insulinotropic action are known in the art (see, e.g., U.S. Pat. Nos. 5,424,286; 6,268,343; 6,329,336; 6,506,724; 6,514,500; 6,528,486; 6,593,295; 6,703,359; 6,706,689; 6,767,887; 6,821,949; 6,849,714; 6,858,576; 6,872,700; 6,887,470; 6,887,849; 6,924,264; 6,956,026; 6,989,366; 7,022,674; 7,041,646; 7,115,569; 7,138,375; 7,141,547; 7,153,825; and 7,157,555). Accordingly, for ease of reference herein, the family of exendin-4 derivatives and analogues having insulinotropic activity is referred to collectively as exendin-4.

The active agents can also be in various forms including, but not limited to, the following: uncharged molecules; components of molecular complexes; and pharmacologically acceptable salts such as hydrochloride, hydrobromide, sulfate, laurates, palmatates, phosphate, nitrate, borate, acetate, maleate, tartrate, oleates, or salicylates. For acidic drugs, salts of metals, amines or organic cations, for example, quaternary ammonium, can be employed. Furthermore, simple derivatives of the drug such as esters, ethers, amides and the like that have solubility characteristics suitable for the purpose of the invention can also be used herein. Drug or other formulation within the osmotic device reservoir can have various art known forms such as solution, dispersion, paste, cream, particle, granule, tablet, emulsions, suspensions, powders and the like. In addition to the one or more active agents, the active agent formulation may optionally include pharmaceutically acceptable carriers and/or additional ingredients such as antioxidants, stabilizing agents, buffers, and permeation enhancers.

The above agents are useful for the treatment of a variety of conditions including but not limited to hemophilia and other blood disorders, growth disorders, diabetes, leukemia, hepatitis, renal failure, bacterial infection, viral infection (e.g., infection by HIV, HCV, etc.), hereditary diseases such as cerbrosidase deficiency and adenosine deaminase deficiency, hypertension, septic shock, autoimmune diseases (e.g., Graves disease, systemic lupus erythematosus and rheumatoid arthritis), shock and wasting disorders, cystic fibrosis, lactose intolerance, Crohn's diseases, inflammatory bowel disease, gastrointestinal and other cancers.

The amount of active or beneficial agent employed in the delivery device of the invention is that amount necessary to deliver a therapeutically effective amount of the agent to achieve the desired therapeutic result at the site of delivery. In practice, this will vary depending upon such variables, for example, as the particular agent, the site of delivery, the severity of the condition, and the desired therapeutic effect. Beneficial agents and their dosage unit amounts are known to the prior art in Goodman & Gilman's The Pharmacological Basis of Therapeutics, 11th Ed., (2005), McGraw Hill; Remington's Pharmaceutical Sciences, 18th Ed., (1995), Mack Publishing Co.; and Martin's Physical Pharmacy and Pharmaceutical Sciences, 1.00 edition (2005), Lippincott Williams & Wilkins. Typically, for an osmotic delivery system, the volume of the chamber comprising the active agent formulation (e.g., chamber 108, FIG. 1) is between about 100 μl to about 1000 μl, more preferably between about 140 μl and about 200 μl. In one embodiment, the volume of the chamber comprising the active agent formulation is about 150 μl.

In one aspect, the present invention provides an active agent formulation of an interferon (e.g., alpha, beta, delta, gamma, lambda, omega or tau interferon), for example, a suspension formulation comprising, a particle formulation comprising omega interferon and a suspension vehicle as described, for example, in published U.S Patent Application Publication Nos. 2006-0263433 and 2006-0251618. The suspension vehicle typically comprises a non-aqueous, single-phase vehicle including one or more polymer and one or more solvent. The vehicle preferably exhibits viscous fluid characteristics. The peptide component comprises the interferon peptide in a particle formulation that is dispersed in the vehicle. Typically, the particle formulation includes a stabilizing component comprising one of more stabilizer component selected from the group consisting of carbohydrates, antioxidants, amino acids, buffers, and inorganic compounds.

3.4.1 Particle Formulations

Particle formulations used in the practice of the invention are preferably chemically and physically stable for at least about 1 month, more preferably at least about 3 months, more preferably at least about 6 months, and even more preferably at least about 12 months, at delivery temperature. The delivery temperature is typically normal human body temperature, for example, about 37° C., or slightly higher, for example, about 40° C. Further, particle formulations of the present invention are preferably chemically and physically stable for at least about 3 months, more preferably at least about 6 months, even more preferably at least about 12 months, at storage temperature. Examples of storage temperatures include refrigeration temperature, for example, about 5° C., or room temperature, for example, about 25° C.

A particle formulation may be considered chemically stable if less than about 25%, preferably less than about 20%, more preferably less than about 15%, more preferably less than about 10%, and more preferably less than about 5% breakdown products of the peptide particles are formed after about 3 months, preferably after about 6 months, preferably after about 12 months at delivery temperature and after about 6 months, after about 12 months, and preferably after about 24 months at storage temperature.

A particle formulation may be considered physically stable if less than about 10%, preferably less than about 5%, more preferably less than about 3%, more preferably less than 1% aggregates of the peptide particles are formed after about 3 months, preferably after about 6 months, at delivery temperature and about 6 months, preferably about 12 months, at storage temperature. Another criterion for demonstrating that a particle formulation is considered physically stable is that the solid state of the particle can remain essentially the same or substantially similar (for example, the particle does not demonstrate a phase transition from amorphous to crystal or an inter-exchange between polymorphous states) for a selected period of time (e.g., after about 3 months, preferably after about 6 months, preferably after about 12 months at delivery temperature and after about 6 months, preferably after about 12 months, and more preferably after about 24 months at storage temperature).

To preserve protein stability generally a protein solution is kept in a frozen condition and lyophilized or spray dried to a solid state. Tg (glass transition temperature) may be one factor to consider in achieving stable compositions of protein. While not intending to be bound by any particular theory, the theory of formation of a high Tg amorphous solid to stabilize peptides, polypeptides, or proteins has been utilized in pharmaceutical industry. Generally, if an amorphous solid has a higher Tg, such as 100° C., protein products will not have mobility when stored at room temp or even at 40° C. because the storage temperature is below the Tg. Calculations using molecular information have shown that if a glass transition temperature is above a storage temperature of 50° C. that there is zero mobility for molecules. No mobility of molecules correlates with no instability issues. Tg is also dependent on the moisture level in the product formulation. Generally, the more moisture, the lower the Tg of the composition.

Accordingly, in some aspects of the present invention, excipients with higher Tg may be included in the protein formulation to improve stability, for example, sucrose (Tg=75° C.) and trehalose (Tg=110° C.). Preferably, particle formulations are formable into particles using processes such as spray drying, lyophilization, desiccation, freeze-drying, milling, granulation, ultrasonic drop creation, crystallization, precipitation, or other techniques available in the art for forming particles from a mixture of components. The particles are preferably substantially uniform in shape and size.

A typical spray dry process may include, for example, loading a spray solution containing a peptide, for example, omega interferon, and stabilizing excipients into a sample chamber. The sample chamber is typically maintained at a desired temperature, for example, refrigeration to room temperature. Refrigeration generally promotes stability of the protein. A feed pump sprays the spray solution into a nozzle atomizer. At the same time, atomized gas (typically, air, nitrogen, or inert gas) is directed at the outlet of the nozzle atomizer to form a mist of droplets from the spray solution. The mist of droplets is immediately brought into contact with a drying gas in a drying chamber. The drying gas removes solvent from the droplets and carries the particles into a collection chamber. In spray drying, factors that can affect yield include, but are not limited to, localized charges on particles (which may promote adhesion of the particles to the spray dryer) and aerodynamics of the particles (which may make it difficult to collect the particles). In general, yield of the spray dry process depends in part on the particle formulation.

The particles are sized such that they can be delivered via an osmotic delivery system of the present invention. Uniform shape and size of the particles typically help to provide a consistent and uniform rate of release from such a delivery system; however, a particle preparation having a non-normal particle size distribution profile may also be used. For example, in an osmotic delivery system as described herein having a delivery orifice 124 of FIG. 1, the size of the particles is less than about 30%, preferably is less than about 20%, preferably is less than about than 10%, and more preferably less than about 5% of the diameter of the delivery orifice.

In a preferred embodiment, when the particles are incorporated in a suspension vehicle they do not settle in less than about 3 months at delivery temperature. Generally speaking, smaller particles tend to have a lower settling rate in viscous suspension vehicles than larger particles. Accordingly, micron- to nano-sized particles are typically desirable. In an embodiment of the particle formulation for use with an osmotic delivery system, wherein the delivery orifice diameter of the implant is in a range of, for example, about 0.1 to about 0.5 mm, particle sizes may be preferably less than about 50 microns, more preferably less than about 10 microns, more preferably in a range from about 3 to about 7 microns. In one embodiment, the orifice is about 0.25 mm (250 μm) and the particle size is approximately 3-5 μm.

In one embodiment, a particle formulation of the present invention comprises one or more interferon peptides (e.g., alpha, beta, delta, gamma, lambda, omega or tau interferon), one or more stabilizers, and optionally a buffer. The stabilizers may be, for example, carbohydrate, antioxidant, amino acid, buffer, or inorganic compound. The amounts of stabilizers and buffer in the particle formulation can be determined experimentally based on the activities of the stabilizers and buffers and the desired characteristics of the formulation. Typically, the amount of carbohydrate in the formulation is determined by aggregation concerns. In general, the carbohydrate level is not be too high so as to avoid promoting crystal growth in the presence of water due to excess carbohydrate unbound to the peptide. Typically, the amount of antioxidant in the formulation is determined by oxidation concerns, while the amount of amino acid in the formulation is determined by oxidation concerns and/or formability of particles during spray drying. Typically, the amount of buffer in the formulation is determined by pre-processing concerns, stability concerns, and formability of particles during spray drying. Buffer may be required to stabilize the peptide during processing, e.g., solution preparation and spray drying, when all excipients are solubilized.

Examples of carbohydrates that may be included in the particle formulation include, but are not limited to, monosaccharides (e.g., fructose, maltose, galactose, glucose, D-mannose, and sorbose), disaccharides (e.g., lactose, sucrose, trehalose, and cellobiose), polysaccharides (e.g., raffinose, melezitose, maltodextrins, dextrans, and starches), and alditols (acyclic polyols; e.g., mannitol, xylitol, maltitol, lactitol, xylitol sorbitol, pyranosyl sorbitol, and myoinsitol). Preferred carbohydrates include non-reducing sugars such as sucrose, trehalose, and raffinose.

Examples of antioxidants that may be included in the particle formulation include, but are not limited to, methionine, ascorbic acid, sodium thiosulfate, catalase, platinum, ethylenediaminetetraacetic acid (EDTA), citric acid, cysteins, thioglycerol, thioglycolic acid, thiosorbitol, butylated hydroxanisol, butylated hydroxyltoluene, and propyl gallate.

Examples of amino acids that may be included in the particle formulation include, but are not limited to, arginine, methionine, glycine, histidine, alanine, L-leucine, glutamic acid, iso-leucine, L-threonine, 2-phenylamine, valine, norvaline, praline, phenylalanine, tryptophan, serine, asparagines, cysteine, tyrosine, lysine, and norleucine. Preferred amino acids include those that readily oxidize, e.g., cysteine, methionine, and tryptophan.

Examples of buffers that may be included in the particle formulation include, but are not limited to, citrate, histidine, succinate, phosphate, maleate, tris, acetate, carbohydrate, and gly-gly. Preferred buffers include citrate, histidine, succinate, and tris.

Examples of inorganic compounds that may be included in the particle formulation include, but are not limited to, NaCl, NaSCN, $Na_2SO4$, $NaHCO_3$, KCl, $KH_2PO4$, $CaCl_2$, and $MgCl_2$.

In addition, the particle formulation may include other excipients such as surfactants, bulking agents, and salts. Examples of surfactants include, but are not limited to, Polysorbate 20, Polysorbate 80, PLURONIC® (BASF Corporation, Mount Olive N.J.) F68, and sodium docecyl sulfate (SDS). Examples of bulking agents include, but are not limited to, mannitol and glycine. Examples of salts include, but are not limited to, sodium chloride, calcium chloride, and magnesium chloride.

3.4.2 Vehicle Formulations

In one aspect of the present invention, a suspension vehicle provides a stable environment in which a particle formulation is dispersed. The suspension vehicle typically comprises one or more polymer and one or more solvent that form a solution of sufficient viscosity to uniformly suspend the particles comprising the peptide. The piston assemblies of the present invention, as described herein above, are substantially impermeable to and substantially resistant to leaching when exposed to the vehicle, particularly to the organic solvent of the vehicle.

The viscosity of the suspension vehicle is typically sufficient to prevent the particle formulation from settling during storage and use in a method of delivery, for example, in the osmotic delivery system. The suspension vehicle is biodegradable in that the suspension vehicle disintegrates or breaks down over a period of time in response to a biological environment. The disintegration of the suspension vehicle may occur by one or more physical or chemical degradative processes such as by enzymatic action, oxidation, reduction, hydrolysis (e.g., proteolysis), displacement (e.g., ion exchange), or dissolution by solubilization, emulsion or micelle formation. After the suspension vehicle disintegrates, components of the suspension vehicle are absorbed or otherwise dissipated by the body and surrounding tissue of the subject.

The solvent in which the polymer is dissolved may affect characteristics of the suspension formulation such as the behavior of the peptide particle formulation during storage. A solvent may be selected in combination with a polymer so that the resulting suspension vehicle exhibits phase separation upon contact with the aqueous environment. Optionally, the solvent may be selected in combination with the polymer so that the resulting suspension vehicle exhibits phase separation upon contact with the aqueous environment having less than approximately about 10% water.

In some embodiments, the solvent may be an acceptable solvent that is not miscible with water. The solvent may also be selected so that the polymer is soluble in the solvent at high concentrations such as at a polymer concentration of greater than about 30%. However, typically the peptide is substantially insoluble in the solvent. Examples of solvents useful in the practice of the present invention include, but are not limited to, lauryl alcohol, benzyl benzoate, benzyl alcohol, lauryl lactate, decanol (also called decyl alcohol), ethyl hexyl lactate, and long chain ($C_8$ to $C_{24}$) aliphatic alcohols, esters, or mixtures thereof. The solvent used in the suspension vehicle may be "dry," in that it has a low moisture content. Preferred solvents for use in formulation of the suspension vehicle include lauryl lactate, lauryl alcohol, and benzyl benzoate.

Additional solvents that may be useful in the practice of the present invention include, but are not limited to, the following: vegetable oils (sesame oil, cottonseed oil, soybean oil); triglycerides; glycerin; glycerol; polyethylene glycol (e.g., PEG400); glycofurol; N-methylpyrrolidone; polysorbates (e.g., polysorbate 20 and polysorbate 80); alpha-tocopherol (e.g., Vitamin E); dimethyl sulfoxide; or silicon medical fluid.

Examples of polymers for formulation of the suspension vehicles of the present invention include, but are not limited to, a polyester (e.g., polylactic acid or polylacticpolyglycolic acid), pyrrolidone (e.g., polyvinylpyrrolidone (PVP) having a molecular weight ranging from approximately 2,000 to approximately 1,000,000), ester or ether of an unsaturated alcohol (e.g., vinyl acetate), polyoxyethylenepolyoxypropylene block copolymer, or mixtures thereof. In one embodiment, the polymer is PVP having a molecular weight of 2,000 to 1,000,000. The polymer used in the suspension vehicle may include one or more different polymers or may include different grades of a single polymer. The polymer used in the suspension vehicle may also be dry or have a low moisture content.

Generally speaking, a suspension vehicle according to the present invention may vary in composition based on the desired performance characteristics. In one embodiment, the suspension vehicle may comprise about 25 wt % to about 80 wt % polymer and about 75 wt % to about 20 wt % solvent, more preferably 40 wt % to about 75 wt % polymer and about 60 wt % to about 25 wt % solvent. Preferred embodiments of a suspension vehicle include vehicles formed of polymer and solvent combined at the following ratios: about 75 wt % polymer and about 25 wt % solvent; about 60 wt % polymer and about 40 wt % solvent; about 55 wt % polymer and about 45 wt % solvent; about 50 wt % polymer and about 50 wt % solvent; about 45 wt % polymer and about 55 wt % solvent; about 40 wt % polymer and about 60 wt % solvent; and about 25 wt % polymer and about 75 wt % solvent.

The suspension vehicle may exhibit Newtonian behavior. The suspension vehicle is typically formulated to provide a viscosity that maintains a uniform dispersion of the particle formulation for a predetermined period of time in a suspension formulation. This helps facilitate making a suspension formulation tailored to provide controlled delivery of the peptide at a desired rate. The viscosity of the suspension vehicle may vary depending on the desired application, the size and type of the particle formulation, and the loading of the particle formulation in the suspension vehicle. The viscosity of the suspension vehicle may be varied by altering the type or relative amount of the solvent or polymer used.

The suspension vehicle may have a viscosity ranging from about 100 poise to about 1,000,000 poise, preferably from about 1,000 poise to about 100,000 poise. The viscosity may be measured at 37° C., at a shear rate of $10^{-4}$/sec, using a parallel plate rheometer. In one embodiment, the viscosity of the suspension vehicle ranges from approximately 5,000 poise to approximately 50,000 poise. In one embodiment, the vehicle has a viscosity of about 16,700 poise at 33° C. In preferred embodiments, the viscosity range is between about 12,000 to about 18,000 poise at 33° C.

The suspension vehicle may exhibit phase separation when contacted with the aqueous environment. However, typically the suspension vehicle exhibits substantially no phase separation as a function of temperature. For example, at a temperature ranging from approximately 0° C. to approximately 70° C. and upon temperature cycling, such as cycling from 4° C. to 37° C. to 4° C., the suspension vehicle typically exhibits no phase separation. In some embodiments of the invention, the suspension vehicle exhibits phase separation when contacted with the aqueous environment having less than approximately 10% water.

The suspension vehicle may be, for example, prepared by combining the polymer and the solvent under dry conditions such as in a dry box. The polymer and solvent may be combined at an elevated temperature, for example, from approximately 40° C. to approximately 70° C., and allowed to liquefy and form the single phase. The ingredients may be blended under vacuum to remove air bubbles produced from the dry ingredients. The ingredients may be combined using a conventional mixer such as a dual helix blade or similar mixer, for example, set at a speed of approximately 40 rpm. However, higher speeds may also be used to mix the ingredients. Once a liquid solution of the ingredients is achieved, the suspension vehicle may be cooled to room temperature. Differential scanning calorimetry (DSC) may be used to verify that the suspension vehicle is a single phase. Further, the components of the suspension vehicle (e.g., the solvent and/or the polymer) may be treated to substantially reduce or substantially remove peroxides.

The particle formulation, comprising a peptide (e.g., omega interferon), is added to the suspension vehicle to form a suspension formulation. The suspension formulation may be prepared by dispersing the particle formulation in the suspension vehicle. The suspension vehicle may be heated and the particle formulation added to the suspension vehicle under dry conditions. The ingredients may be mixed under vacuum at an elevated temperature such as from about 40° C. to about 70° C. The ingredients may be mixed at a sufficient speed such as from about 40 rpm to about 120 rpm, and for a sufficient amount of time, for example, about 15 minutes, to achieve a uniform dispersion of the particle formulation in the suspension vehicle. The mixer may be a dual helix blade or other suitable mixer. The resulting mixture may be removed from the mixer, sealed in a dry container to prevent water from contaminating the suspension formulation, and allowed to cool to room temperature before further use, for example, loading into an osmotic delivery system.

The suspension formulation typically has an overall moisture content of less than about 10 wt %, preferably less than about 5 wt %, and more preferably less than about 4 wt %.

In summary, the components of the suspension vehicle provide biocompatibility with the subject in whom use is intended. Components of the suspension vehicle offer suitable chemico-physical properties to form stable suspensions of, for example, dry powder particle formulations. These properties include, but are not limited to, the following: viscosity of the suspension; purity of the vehicle; residual moisture of the vehicle; density of the vehicle; compatibility with the dry powders; compatibility with implantable devices; molecular weight of the polymer; stability of the vehicle; and hydrophobicity and hydrophilicity of the vehicle. These properties can be manipulated and controlled, for example, by variation of the vehicle composition and manipulation of the ratio of components used in the suspension vehicle.

All components included in the particle formulation are typically acceptable for pharmaceutical use in subjects, particularly humans.

One embodiment of the present invention includes an osmotic delivery system as described herein, comprising an suspension formulation as follows: an omega interferon particle formulation (omega interferon:sucrose:methionine:citrate in a ratio of 1:2:1:2.15 by weight) suspended in a benzyl benzoate/polyvinylpyrrolidone (BB/PVP) suspension vehicle with a target particle loading of approximately 10% (w/w). Reservoirs of the osmotic delivery system are filled with approximately 150 μL of the suspension.

3.5.0 Reservoir

Materials that may be used for the reservoir (e.g., 102, FIG. 1) are sufficiently rigid to withstand expansion of the osmotic agent formulation (e.g., 114, FIG. 1) without changing its size or shape. Where the osmotic delivery system is implantable, the materials are typically selected to ensure that the reservoir will not leak, crack, break, or distort under stresses to which it may be subjected during implantation or under stresses due to the pressures generated during operation. The reservoir may be formed of non-reactive (or inert), biocompatible, natural or synthetic materials which are known in the art. The material of the reservoir may be non-bioerodible (i.e., not soluble in a fluid environment of use, e.g., gastric fluid) or may be bioerodible (i.e., soluble in a fluid environment of use, e.g., gastric fluid). Preferably, the material of the reservoir is non-bioerodible. Generally, preferred materials for the reservoir are those acceptable for human implantation. Preferably, the material of the reservoir is impermeable, particularly when stability of the formulation in the reservoir is sensitive to fluids in the fluid environment of use (e.g., after implantation in a subject).

Examples of materials suitable for the reservoir include non-reactive, biocompatible polymers and metals or alloys. Examples of non-reactive, biocompatible polymers for the reservoir include, but are not limited to, acrylonitrile polymers such as acrylonitrile-butadiene-styrene terpolymer; halogenated polymers such as polytetrafluoroethylene, polychlorotrifluoroethylene, copolymer tetrafluoroethylene and hexafluoropropylene; polyimide; polysulfone; polycarbonate; polyethylene; polypropylene; polyvinylchloride-acrylic copolymer; polycarbonate-acrylonitrile-butadiene-styrene; and polystyrene. Examples of metallic, biocompatible materials for the reservoir 102 include, but are not limited to, stainless steel, titanium, platinum, tantalum, gold, and their alloys, as well as gold-plated ferrous alloys, platinum-plated ferrous alloys, cobalt-chromium alloys and titanium nitride coated stainless steel. For size-critical applications, high payload capability, long duration applications, and applications where the formulation is sensitive to body chemistry at the implantation site, the reservoir is preferably made of titanium or a titanium alloy having greater than about 60%, more preferably greater than about 85% titanium.

The body of the reservoir may be labeled, for example, using laser etching, to indicate the nature of the active agent, dosage of the active agent, manufacturer, and the like. In addition, the body of the reservoir may comprise a marking, for example, a grooved band, to provide directional orientation to the user for the product, for example, a grooved band may be asymmetrically placed relative to the mid-point of the body of the reservoir to indicate which end of the reservoir comprises the semipermeable membrane or the flow modulator. Such a groove is particularly useful when both ends of the body of the reservoir are similar in appearance.

The total size of the reservoir is selected based on a variety of parameters, for example, (i) the volume occupied by a flow modulator (e.g., FIG. 1, flow modulator 120), (ii) the volume occupied by an active agent formulation (e.g., FIG. 1, chamber 108), (iii) the volume occupied by a piston assembly (e.g., FIG. 1, piston assembly 200), (iv) the volume occupied by an osmotic agent formulation (e.g., FIG. 1, osmotic agent formulation 114), (v) the volume occupied by a semipermeable membrane (e.g., FIG. 1 semipermeable membrane 116), and (vi) the amount of active agent being delivered and the period of time over which the osmotic delivery system will be delivering the active agent. Typically, the total reservoir volume (i.e., the volume defined by interior chamber of the reservoir in the absence of other components) is between about 200 µl to about 2000 µl, more preferably between about 250 µl and about 400 µl. In one embodiment, the total reservoir volume is about 300 µl.

3.6.0 Flow Modulator and Orifice

The flow modulator is typically a plug-like member defining a liquid flow path for exit of the active agent from the osmotic delivery system (see, e.g., U.S. Pat. Nos. 5,728, 396, 5,997,527, 6,217,906, 6,287,295, 6,395,292, 6,524,305, 6,635,268, 6,840,931, and 6,923,800).

The invention is not limited to any particular flow modulator as long as the flow modulator is able to deliver the active agent formulation in a desired manner. Preferably, the flow modulator (e.g., 120, FIG. 1) allows delivery of the active agent formulation (e.g., 112, FIG. 1) while controlling back-diffusion of external fluid into the lumen (e.g., 104, FIG. 1). The end (e.g., 122, FIG. 1) may be open and the flow modulator (e.g., 120, FIG. 1) may be provided in the form of a plug which is inserted in the open end. Alternately, the flow modulator (e.g., 120, FIG. 1) may be integrated with the end (e.g., 122, FIG. 1) of the reservoir (e.g., 102, FIG. 1).

The delivery orifice flow channel provided by the flow modulator may be, for example, spiral in shape or straight. Further, the orifice flow channel may be of a variety of shapes including, but not limited to, circular, triangular, square, D-shaped, oval, or elongated (e.g., slit-like). The flow modulator is preferably made of a non-reactive (or inert), biocompatible material. Exemplary materials include, but are not limited to, metals such as titanium, stainless steel, platinum and their alloys, and cobalt-chromium alloys. Other compatible materials include polymers such as polyethylene, polypropylene, polycarbonate, polymethylmethacrylate, and polyaryletherkeones, e.g., polyetheretherketone (PEEK). In one embodiment, the orifice flow channel is a D-shaped channel having a nominal "diameter" (i.e., measured across the widest opening) of 250 µm (0.25 mm).

The flow modulator may be assembled to the reservoir by using a number of methods, for example, a thread and screw method wherein the flow modulator or the interior surface of the lumen or both comprise ribs, for example, complementary continuous helical threads/grooves. Single, double, triple, or quadruple threads/grooves may be used.

Alternatively, the flow modulator may be assembled to the reservoir by a press-fit (i.e., interference fit) where the outside of the flow modulator is slightly larger than the inside diameter of the reservoir. Typically, this assembly method is faster and easier to automate than other assembly methods that may be used in the practice of the present invention such as thread and screw assemblies.

A variety of types of delivery orifices are known in the art and useful in the practice of the present invention. For example, a flexible flow moderator may have at least one slit orifice which is in fluid communication with the chamber comprising the active agent. The slit orifice may be, for example, closed when the pressure of the fluid in the active agent chamber is less than a predetermined pressure (see, e.g., U.S. Pat. No. 5,997,527). The slit orifice may open only to the minimum dimension required to allow the flow generated by the osmotic pumping rate (see, e.g., U.S. Pat. No. 6,217,906).

An osmotic delivery system flow modulator assembly may also include, for example, a body defining an open pathway (e.g., a hole or flow channel) through the body of the flow modulator that communicates between two opposing ends of the body (e.g., where the orifice defines the exit site of the active agent). The open pathway may be, for example, straight, spiral, or curved. The flow modulator may further comprise a stopper that serves to close the orifice to the external environment until the osmotic delivery system is ready for use (see, e.g., U.S. Pat. No. 6,524,305). Prior to use, for example, insertion of an implantable osmotic delivery system into a subject, such a stopper is removed.

In one embodiment, the flow moderator comprises two polyetheretherketone machined parts, an inner core and an outer sleeve, whereby a continuous spiral delivery channel is formed between the two parts when they are assembled. The two-piece moderator is assembled by press-fitting into the reservoir (wherein neither the reservoir nor the moderator comprises ribs). In other embodiments, ribbed components may be used.

The present invention also includes methods of manufacturing the osmotic delivery systems of the present invention, comprising assembly of the above-described components.

Furthermore, the osmotic delivery systems of the present invention may be individually packaged or packaged in groups. Such packaging may be, for example, foil pouches or vials. The packaging may include a desiccant or the osmotic delivery systems may be packaged under nitrogen or vacuum.

4.0.0 Uses of the Osmotic Delivery System

In one aspect, the present invention provides methods of treatment for a subject comprising administering to a subject in need of treatment an active agent using the osmotic delivery system described herein above. Typically, the osmotic delivery system is implanted in the subject such that the system is in contact with a fluid environment within the subject.

The osmotic delivery system of the present invention allows the delivery of an active agent to a subject in a controlled manner over a prolonged period without intervention. Sustained delivery of an active agent can improve the therapeutic effect of the active agent by reduction or elimination of peak plasma-level related effects (e.g., of multiple bolus injections), often associated with toxicities, as well as sub-therapeutic troughs, often associated with suboptimal therapeutic effects. This improved therapeutic effect may include, for example, potentially minimizing systemic side effects. Sustained delivery of an active agent without intervention can be provided by, for example, implanting in a subject one or more osmotic delivery system described herein.

Such implantable osmotic delivery systems can be designed to provide therapeutic doses of the drug over periods of weeks, months, or even a year or more. Implantable osmotic delivery systems once inserted in a subject are not easily tampered with by the subject. Accordingly, compliance to a required dosing regimen is generally assured.

A subject being treated with the suspension formulations of the present invention, for example, delivered to the subject from an implanted osmotic delivery system, may also benefit from co-treatment with other agents such as small molecules. In one embodiment, when the osmotic delivery system of the present invention is used to deliver an interferon, co-treatment may include treatment with an inosine monophosphate dehydrogenase inhibitor (e.g., ribavirin, a ribavirin analog, mycophenolic acid, mycophenolate mofetil, mycophenolic acid sodium, aminothiadiazole, thiophenfurin, tiazofurin, and/or viramidine).

In one embodiment, the invention relates to a method of treating an interferon-responsive disorder comprising administering to a subject a suspension formulation described above (e.g., comprising an interferon, for the treatment of HCV or multiple sclerosis; for example, omega interferon, beta interferon, alpha interferon or pegylated alpha interferon for the treatment of HCV; or beta interferon for the treatment of multiple sclerosis). This improved therapeutic effect may, for example potentially minimize known systemic side effects of interferon treatment such as fatigue and flu-like symptoms.

Certain interferons are used for treatment of certain viral infections (e.g., infection by HCV or HIV), multiple sclerosis, and certain cancers. Many disease states require long-term treatment with a particular interferon. Accordingly, the osmotic delivery system of the present invention coupled with the suspension formulations described herein above may provide a convenient and effective alternative to repeated dosing with, for example, injectable formulations of interferon. Treatment of interferon-responsive disorders using the osmotic delivery system of the present invention comprising a suspension formulation comprising an interferon may also include co-treatment with other beneficial active agents (e.g., ribavirin in the case of viral infections).

In one aspect, the present invention includes a method of treating viral infection, for example, infection with HCV, in a subject in need of such treatment, comprising administering a therapeutically effective amount of interferon to the subject over time, wherein the interferon is, for example, alpha, beta, or omega interferon and is administered using an implanted osmotic delivery system. In one embodiment, the osmotic delivery system is designed to provide a volumetric flow rate ($\mu$l/day) of about 1.3 to about 1.7 $\mu$l/day. This corresponds to a cumulative protein (e.g., of omega interferon) release of about 120 to about 230 micrograms during the time period of day 14 to 21 of operation of the osmotic delivery system after implantation in a subject. Typically, the time course for delivery is about 90 days, with an additional approximately 10 days of operation to provide some flexibility for the subject being treated.

In another aspect, the present invention includes a method of treating multiple sclerosis in a subject in need of such treatment, comprising administering a therapeutically effective amount of interferon to the subject over time, wherein the interferon is administered using an implanted osmotic delivery system. In one embodiment the interferon is beta or omega interferon.

In yet another aspect, the present invention includes a method of treating diabetes or diabetes-related disorders in a subject in need of such treatment, comprising administering a therapeutically effective amount of an insulinotropic peptide to the subject over time, wherein the insulinotropic peptide is administered using an implanted osmotic delivery system. In one embodiment the insulinotropic peptide is a GLP-1 peptide (including GLP-1 analogs or derivatives) or an exendin-4 peptide (including exendin-4 analogs or derivatives).

Aspects of the present invention are described herein below with reference to an osmotic delivery system comprising omega interferon as an active agent. These examples are not intended to be limiting.

Other objects may be apparent to one of ordinary skill upon reviewing the following specification and claims.

EXPERIMENTAL

The following examples are put forth so as to provide those of ordinary skill in the art with a complete disclosure and description of how to make and use the devices, methods, and formulae of the present invention, and are not intended to limit the scope of what the inventor regards as the invention. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

The compositions produced according to the present invention meet the specifications for content and purity required of pharmaceutical products.

Example 1

Osmotic Delivery System Assembly

An osmotic delivery system, as illustrated in FIG. 1, containing omega interferon for the treatment of, for example, HCV infection, was assembled from the following components: (i) reservoir made of implant grade titanium alloy and having undercuts at an end thereof, (ii) osmotic active formulation in the form of two cylindrical tablets, each tablet including primarily sodium chloride salt with cellulosic and povidone binders, (iii) piston assembly as described in FIG. 2A made of ultra-high molecular weight polyethylene, (iv) semipermeable membrane made of polyurethane and having four retaining ribs that mate with undercuts in reservoir, (v) flow modulator having a spiral orifice, and (vi) an active agent formulation comprising a suspension formulation, comprising a particle formulation (omega interferon, sucrose, methionine, citric acid monohydrate, and sodium citrate) in a suspension vehicle (benzyl benzoate and povidone).

Example 2

Cumulative Release Rate of Omega Interferon

Figure 3:
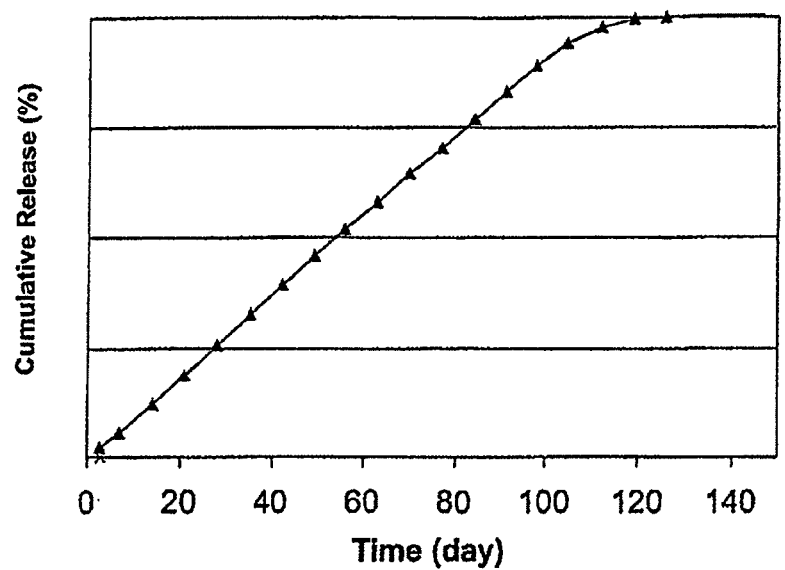
FIG. 3 depicts cumulative release of an active agent formulation over time using the piston assembly of FIG. 2A.

Reservoirs of several osmotic delivery systems, as described in EXAMPLE 1, were filled with 150-μL of the suspension formulation, as described in EXAMPLE 1. The semipermeable membrane ends of the osmotic delivery systems were placed into stoppered glass vials filled with 3 mL phosphate buffer solution (PBS), and the flow modulator ends of the osmotic delivery systems were placed into glass vials filled with 2.5 to 3 mL release rate medium (citrate buffer solution at pH 6.0 with 0.14 M NaCl and 0.2% sodium azide). The systems were placed into capped test tubes, with the flow modulator side down, and partially immersed in a 37° C. water bath. At specified time points, the glass vials at the flow modulator ends were replaced with new glass vials filled with 2.5 to 3 mL release rate medium (citrate buffer solution at pH 6.0 with 0.14 M NaCl and 0.2% sodium azide). Samples were collected from the flow modulator ends and analyzed using Reversed Phase High Performance Liquid Chromatography (RP-HPLC). FIG. 3 shows the cumulative release rate of omega interferon formulation as a function of time over 120 days. In FIG. 3, the vertical axis represents the percent cumulative release (Cumulative Release (%)) and the horizontal axis represents time in days (Time (day)).

The vertical axis in FIG. 3 represents the range zero to 100% of cumulative active agent delivered from the osmotic system. These data illustrate that osmotic delivery systems comprising the piston assemblies of the present invention provide pharmaceutically acceptable continuous, linear sustained release of an active agent for the intended duration of delivery. The osmotic systems of FIG. 3 were designed to deliver an active agent for a minimum of 100 days.

Example 3

Evaluation of Leachates Released to Solvent

Flow modulators made of polyetheretherketone (PEEK) were inserted at ends of reservoirs made of titanium alloy. Piston assemblies, essentially as shown and described in FIG. 2A, made of ultra-high molecular weight polyethylene were placed in the lumen of the reservoirs. 100% benzyl benzoate solvent was loaded into the lumens of the reservoirs in contact with the flow modulators and the piston assemblies. The systems were stored at 40° C. for 3 months and sampled at 0, 45, and 90 days. The samples were analyzed by chromatic techniques to determine if volatile or non-volatile leachates were present in the benzyl benzoate. The limit of quantification (LOQ) for volatile leachates was 1.4 μg/ml and for non-volatile leachates was 9.0 μg/ml. The results of the analyses are presented in Table 2 below.

TABLE 2

|  | t = 0 days | t = 45 days | t = 90 days |
|---|---|---|---|
| Volatile leachates, μg/ml (n = 3) | <1.4 | <1.4 | <1.4 |
| Non-volatile leachates, μg/ml (n = 3) | <9 | <9 | <9 |

These data illustrate that use of the piston assemblies of the present invention, for example, piston assembly as described in FIG. 2A made of ultra-high molecular weight polyethylene, when employed in osmotic delivery systems are resistant to leaching and result in levels of volatile and non-volatile leachates that are below quantifiable limits and below maximum allowable limits that are pharmaceutically acceptable.

Example 4

Comparison of Leachates Released to Solvent from Piston Assemblies Made of Fluorosilicone Flow modulators made of polyetheretherketone (PEEK) were inserted at ends of reservoirs made of titanium alloy. Conventional pistons made of fluorosilicone were placed in the lumen of the reservoirs. 100% benzyl benzoate solvent was loaded into the lumens of the reservoirs in contact with the flow modulators and the conventional pistons. The systems were stored at 40° C. for 3 months and sampled at 0, 45, and 90 days. The samples were analyzed by chromatic techniques to determine if volatile or non-volatile leachates were present in the benzyl benzoate. The limit of quantification (LOQ) for volatile leachates was 1.4 μg/ml and for non-volatile leachates was 9.0 μg/ml. The results of the analyses are presented in Table 3 below.

TABLE 3

|  | t = 0 days | t = 45 days | t = 90 days |
|---|---|---|---|
| Volatile leachates, μg/ml (n = 3) | <1.4 | 3.7 (avg) | <1.4 |
| Non-volatile leachates, μg/ml (n = 3) | 56 (avg) | 283 (avg) | 408 (avg) |

These data illustrate that use of the piston assemblies of the present invention, for example, piston assembly as described in FIG. 2A made of ultra-high molecular weight polyethylene, when employed in osmotic delivery systems provide superior performance in regard to resistance to leaching, resulting in lower levels of volatile and non-volatile leachates (e.g., see data in Table 2) relative to conventional pistons, for example, comprising fluorosilicone (e.g., compare data in Table 2 and Table 3).

As is apparent to one of skill in the art, various modification and variations of the above embodiments can be made without departing from the spirit and scope of this invention. Such modifications and variations are within the scope of this invention.

What is claimed is:

1. A method of treating diabetes in a subject in need of such treatment, comprising administering an osmotic delivery system loaded with a suspension formulation comprising an active agent to the subject, wherein the osmotic delivery system comprises:
- a reservoir comprising an interior wall defining a lumen that contains the suspension formulation and an osmotic agent formulation;
- a piston assembly positioned in the lumen to isolate the suspension formulation from the osmotic agent formulation, wherein the piston assembly comprises:
  - a columnar body that has a core made of a polymeric material comprising an ultra-high molecular weight polyethylene,
  - a rim at a distal end thereof for engaging and sealing against the interior wall of the reservoir, and
  - a spring retained at the distal end for biasing the rim against the wall of the reservoir;
- the suspension formulation comprises a suspension vehicle comprising one or more organic solvents selected from the group consisting of benzyl benzoate and benzyl alcohol;
- the suspension formulation comprises less than 9.0 μg/mL of non-volatile leachates produced by the piston assembly and resulting from an interaction between the suspension formulation and the piston assembly; and
- the active agent is exendin-4.

2. The method of claim 1, wherein the spring is retained in a cavity at the distal end of the columnar body.

3. The method of claim 1, wherein the spring is made of a non-reactive metal.

4. The method of claim 1, the osmotic delivery system further comprising a semipermeable membrane positioned at a first end of the reservoir adjacent the osmotic agent formulation.

5. The method of claim 4, the osmotic delivery system further comprising a flow modulator positioned at a second end of the reservoir adjacent the suspension formulation, said flow modulator having an orifice for delivering the suspension formulation to the fluid environment.

6. The method of claim 1, wherein the piston assembly is movable within the reservoir in response to pressure within the reservoir.

7. The method of claim 1, wherein the reservoir is made of an impermeable material.

8. The method of claim 1, wherein the suspension formulation comprises a particle formulation of the active agent.

9. The method of claim 1, wherein:
- the reservoir is made of a titanium alloy;
- the suspension formulation comprises
  - a particle formulation of the active agent, the particle formulation comprising exendin-4 and further comprising sucrose, methionine, citric acid monohydrate, and sodium citrate, and
  - the suspension vehicle comprising benzyl benzoate and further comprising polyvinylpyrrolidone;
- the osmotic agent formulation comprises two cylindrical tablets, each tablet comprising sodium chloride salt with cellulosic and povidone binders;
- the spring retained at the distal end for biasing the rim against the wall of the reservoir is a canted coil spring;
- the osmotic delivery system further comprising:
- a semipermeable membrane positioned at a first distal end of the reservoir adjacent the osmotic agent formulation, wherein the semipermeable membrane comprises polyurethane; and
- a flow modulator positioned at a second distal end of the reservoir adjacent the suspension formulation, wherein the flow modulator comprises polyetheretherketone.

10. The method of claim 1, wherein the suspension formulation comprises less than 1.4 μg/mL of volatile leachates produced by the piston assembly and resulting from an interaction between the suspension formulation and the piston assembly.

11. The method of claim 1, wherein the suspension vehicle comprises benzyl benzoate.

12. The method of claim 1, wherein the suspension vehicle comprises benzyl alcohol.

* * * * *